(12) United States Patent
Xu et al.

(10) Patent No.: US 6,262,245 B1
(45) Date of Patent: Jul. 17, 2001

(54) COMPOUNDS FOR IMMUNOTHERAPY OF PROSTATE CANCER AND METHODS FOR THEIR USE

(75) Inventors: Jiangchun Xu, Bellevue; Davin C. Dillon, Redmond, both of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/030,607

(22) Filed: Feb. 25, 1998

Related U.S. Application Data

(63) Continuation-in-part of application No. 09/020,956, filed on Feb. 9, 1998, which is a continuation-in-part of application No. 08/904,804, filed on Aug. 1, 1997, now abandoned, which is a continuation-in-part of application No. 08/806,099, filed on Feb. 25, 1997, now abandoned.

(51) Int. Cl.$^7$ .............................. C07H 1/00; C07H 5/04; C07H 5/06; C07H 19/00; C07H 21/00

(52) U.S. Cl. ..................... 536/23.5; 536/1; 536/1.11; 536/18.7; 536/22.1; 536/23.1; 435/320.1; 435/325; 435/363

(58) Field of Search ................... 424/185.1; 514/44, 514/2, 12; 536/23.1, 23.5, 1, 1.11, 18.7, 22.1; 435/320.1, 69.1, 325, 363

(56) References Cited

U.S. PATENT DOCUMENTS 5,786,148   7/1998   Bandman et al. ................. 435/6

FOREIGN PATENT DOCUMENTS

| | | |
|---|---|---|
| 19649207 | 2/1998 | (DE) . |
| 317 141 A2 | 5/1989 | (EP) . |
| 652 014 A1 | 5/1995 | (EP) . |
| 936 270 A2 | 8/1999 | (EP) . |
| WO 93/14755 | 8/1993 | (WO) . |
| WO 93/25224 | 12/1993 | (WO) . |
| WO 94/09820 | 5/1994 | (WO) . |
| WO 95/04548 | 2/1995 | (WO) . |
| WO 95/14772 | 6/1995 | (WO) . |
| WO 95/30758 | 11/1995 | (WO) . |
| WO 96/21671 | 7/1996 | (WO) . |
| WO 97/33909 | 9/1997 | (WO) . |
| WO 98/12302 | 3/1998 | (WO) . |
| WO 98/17687 | 4/1998 | (WO) . |
| WO 98/20117 | 5/1998 | (WO) . |
| WO 98/31799 | 7/1998 | (WO) . |
| WO 98/37093 | 8/1998 | (WO) . |
| WO 98/37418 | 8/1998 | (WO) . |
| WO 98/38310 | 9/1998 | (WO) . |
| WO 98/39446 | 9/1998 | (WO) . |
| WO 98/45435 | 10/1998 | (WO) . |
| WO 98/50567 | 11/1998 | (WO) . |
| WO 99/06548 | 2/1999 | (WO) . |
| WO 99/06550 | 2/1999 | (WO) . |
| WO 99/06552 | 2/1999 | (WO) . |
| WO 99/25825 | 5/1999 | (WO) . |
| WO 99/31236 | 6/1999 | (WO) . |

OTHER PUBLICATIONS

Derwent Geneseq Database, Accession No. V58522, Dec. 8,1998.
Derwent Geneseq Database, Accession No. V61287, Jan. 6, 1999.
Alexeyev et al., "Improved antibiotic–resistance gene cassettes and omega elements for *Escherichia coli* coli vector construction and in vitro deletion/insertion mutagenesis," *Gene* 160: 63–67, 1995.
Blok et al., "Isolation of cDNAs That Are Differentially Expressed Between Androgen–Dependent and Androgen-Independent Prostate Carcinoma Cells Using Differential Display PCR," *The Prostate* 213–224, 1995.
Database EMBL Accession No. AA453562, Jun. 11, 1997, Hillier et al., "Homo Sapiens cDNA Clone 788180."
El–Shirbiny, Prostatic Specific Antigen, *Advances In Clinical Chemistry* 31: 99–133, 1994.
Robson et al., "Identification of prostatic androgen regulated genes using the differential display technique," *Proceedings Of The American Association For Cancer Reseach Meeting 86* , 36 : p. 266, Abstract No. 1589, 1995.
Short et al., "λ ZAP: a bacteriophage λ expression vector with in vivo excision properties," *Nucleic Acids Research* 16(15): 7583–7600, 1988.
Harris et al. "Polycystic Kidney Disease 1: identification and analysis of the primary defect" J of the Am. Soc. of Nephrology. vol. 6, pp. 1125–1133, 1995.*
Ahn et al. "The structural and functional diversity of dystrophin" Nature Genetics vol. 3, pp. 283–291, Apr. 1993.*
Cawthon et al. "cDNA sequence and genomic structure of EV12B, a gene lying within an intron of the neurofibromatosis type 1 gene" Genomics vol. 9, pp. 446–460, 1991.*
Ezell. "Cancer vaccines: an idea whose time has come" The Journal of NIH Research vol. 7, pp. 46–49, Jan. 1995.*
Hudson et al. Genebank Accession No. G22461, May 31, 1996.*
Genbank Accession No. AA551759, Aug. 11, 1997.*
Genbank Accession No. AA631143, Oct. 1997.*
Hiller et al. Genbank Accession No. AA100799, Dec. 1997.*
Genbank Accession No. AA551449, Sep. 5, 1997.*
Genbank Accession No. AA653016, Nov. 1997.*
Hillier et al. Genbank Accession No. R20590, Apr. 18, 1995.*

\* cited by examiner

*Primary Examiner*—Sheela Huff
*Assistant Examiner*—Alana M. Harris
(74) *Attorney, Agent, or Firm*—Seed Intellectual Property Law Group PLLC

(57) ABSTRACT

Compounds and methods for treating prostate cancer are provided. The inventive compounds include polypeptides containing at least a portion of a prostate tumor protein. Vaccines and pharmaceutical compositions for immunotherapy of prostate cancer comprising such polypeptides, or DNA molecules encoding such polypeptides, are also provided, together with DNA molecules for preparing the inventive polypeptides.

13 Claims, No Drawings

SEQUENCE LISTING (1) GENERAL INFORMATION:

(iii) NUMBER OF SEQUENCES: 224

(2) INFORMATION FOR SEQ ID NO: 1:

(i) SEQUENCE CHARACTERISTICS:
      (A) LENGTH: 814 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

| | | | | | |
|---|---|---|---|---|---|
| TTTTTTTTTT | TTTTTCACAG | TATAACAGCT | CTTTATTTCT | GTGAGTTCTA | CTAGGAAATC | 60 |
| ATCAAATCTG | AGGGTTGTCT | GGAGGACTTC | AATACACCTC | CCCCCATAGT | GAATCAGCTT | 120 |
| CCAGGGGGTC | CAGTCCCTCT | CCTTACTTCA | TCCCCATCCC | ATGCCAAAGG | AAGACCCTCC | 180 |
| CTCCTTGGCT | CACAGCCTTC | TCTAGGCTTC | CCAGTGCCTC | CAGGACAGAG | TGGGTTATGT | 240 |
| TTTCAGCTCC | ATCCTTGCTG | TGAGTGTCTG | GTGCGTTGTG | CCTCCAGCTT | CTGCTCAGTG | 300 |
| CTTCATGGAC | AGTGTCCAGC | ACATGTCACT | CTCCACTCTC | TCAGTGTGGA | TCCACTAGTT | 360 |
| CTAGAGCGGC | CGCCACCGCG | GTGGAGCTCC | AGCTTTTGTT | CCCTTTAGTG | AGGGTTAATT | 420 |
| GCGCGCTTGG | CGTAATCATG | GTCATAACTG | TTTCCTGTGT | GAAATTGTTA | TCCGCTCACA | 480 |
| ATTCCACACA | ACATACGAGC | CGGAAGCATA | AAGTGTAAAG | CCTGGGGTGC | CTAATGAGTG | 540 |
| ANCTAACTCA | CATTAATTGC | GTTGCGCTCA | CTGNCCGCTT | TCCAGTCNGG | AAAACTGTCG | 600 |
| TGCCAGCTGC | ATTAATGAAT | CGGCCAACGC | NCGGGGAAAA | GCGGTTTGCG | TTTTGGGGGC | 660 |
| TCTTCCGCTT | CTCGCTCACT | NANTCCTGCG | CTCGGTCNTT | CGGCTGCGGG | GAACGGTATC | 720 |
| ACTCCTCAAA | GGNGGTATTA | CGGTTATCCN | NAAATCNGGG | GATACCCNGG | AAAAAANTTT | 780 |
| AACAAAAGGG | CANCAAAGGG | CNGAAACGTA | AAAA | | | 814 |

(2) INFORMATION FOR SEQ ID NO: 2:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

| | | | | | |
|---|---|---|---|---|---|
| ACAGAAATGT | TGGATGGTGG | AGCACCTTTC | TATACGACTT | ACAGGACAGC | AGATGGGGAA | 60 |
| TTCATGGCTG | TTGGAGCAAT | AGAACCCCAG | TTCTACGAGC | TGCTGATCAA | AGGACTTGGA | 120 |
| CTAAAGTCTG | ATGAACTTCC | CAATCAGATG | AGCATGGATG | ATTGGCCAGA | AATGAAGAAG | 180 |
| AAGTTTGCAG | ATGTATTTGC | AAAGAAGACG | AAGGCAGAGT | GGTGTCAAAT | CTTTGACGGC | 240 |
| ACAGATGCCT | GTGTGACTCC | GGTTCTGACT | TTTGAGGAGG | TTGTTCATCA | TGATCACAAC | 300 |
| AAGGAACGGG | GCTCGTTTAT | CACCAGTGAG | GAGCAGGACG | TGAGCCCCCG | CCCTGCACCT | 360 |
| CTGCTGTTAA | ACACCCCAGC | CATCCCTTCT | TTCAAAAGGG | ATCCACTAGT | TCTAGAAGCG | 420 |
| GCCGCCACCG | CGGTGGAGCT | CCAGCTTTTG | TTCCCTTTAG | TGAGGGTTAA | TTGCGCGCTT | 480 |
| GGCGTAATCA | TGGTCATAGC | TGTTTCCTGT | GTGAAATTGT | TATCCGCTCA | CAATTCCCCC | 540 |
| AACATACGAG | CCGGAACATA | AAGTGTTAAG | CCTGGGGTGC | CTAATGANTG | AGCTAACTCN | 600 |
| CATTAATTGC | GTTGCGCTCA | CTGCCCGCTT | TCCAGTCGGG | AAAACTGTCG | TGCCACTGCN | 660 |
| TTANTGAATC | NGCCACCCCC | CGGGAAAAGG | CGGTTGCNTT | TTGGGCCTCT | TCCGCTTTCC | 720 |
| TCGCTCATTG | ATCCTNGCNC | CCGGTCTTCG | GCTGCGGNGA | ACGGTTCACT | CCTCAAAGGC | 780 |
| GGTNTNCCGG | TTATCCCCAA | ACNGGGGATA | CCCNGA | | | 816 |

(2) INFORMATION FOR SEQ ID NO: 3:

(i) SEQUENCE CHARACTERISTICS:
        (A) LENGTH: 773 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

| | | | | | |
|---|---|---|---|---|---|
| CTTTTGAAAG | AAGGGATGGC | TGGGGTGTTT | AACAGCAGAG | GTGCAGGGCG | GGGGCTCACG | 60 |
| TCCTGCTCCT | CACTGGTGAT | AAACGAGCCC | CGTTCCTTGT | TGTGATCATG | ATGAACAACC | 120 |
| TCCTCAAAAG | TCAGAACCGG | AGTCACACAG | GCATCTGTGC | CGTCAAAGAT | TTGACACCAC | 180 |
| TCTGCCTTCG | TCTTCTTTGC | AAATACATCT | GCAAACTTCT | TCTTCATTTC | TGGCCAATCA | 240 |
| TCCATGCTCA | TCTGATTGGG | AAGTTCATCA | GACTTTAGTC | CANNTCCTTT | GATCAGCAGC | 300 |
| TCGTAGAACT | GGGGTTCTAT | TGCTCCAACA | GCCATGAATT | CCCCATCTGC | TGTCCTGTAA | 360 |
| GTCGTATAGA | AAGGTGCTCC | ACCATCCAAC | ATGTTCTGTC | CTCGAGGGGG | GGCCCGGTAC | 420 |
| CCAATTCGCC | CTATANTGAG | TCGTATTACG | CGCGCTCACT | GGCCGTCGTT | TTACAACGTC | 480 |
| GTGACTGGGA | AAACCCTGGG | CGTTACCAAC | TTAATCGCCT | TGCAGCACAT | CCCCCTTTCG | 540 |
| CCAGCTGGGC | GTAATANCGA | AAAGGCCCGC | ACCGATCGCC | CTTCCAACAG | TTGCGCACCT | 600 |
| GAATGGGNAA | ATGGGACCCC | CCTGTTACCG | CGCATTNAAC | CCCCGCNGGG | TTTNGTTGTT | 660 |
| ACCCCCACNT | NNACCGCTTA | CACTTTGCCA | GCGCCTTANC | GCCCGCTCCC | TTTCNCCTTT | 720 |
| CTTCCCTTCC | TTTCNCNCCN | CTTTCCCCCG | GGGTTTCCCC | CNTCAAACCC | CNA | 773 |

(2) INFORMATION FOR SEQ ID NO: 4:

(i) SEQUENCE CHARACTERISTICS:
        (A) LENGTH: 828 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

| | | | | | |
|---|---|---|---|---|---|
| CCTCCTGAGT | CCTACTGACC | TGTGCTTTCT | GGTGTGGAGT | CCAGGGCTGC | TAGGAAAAGG | 60 |
| AATGGGCAGA | CACAGGTGTA | TGCCAATGTT | TCTGAAATGG | GTATAATTTC | GTCCTCTCCT | 120 |
| TCGGAACACT | GGCTGTCTCT | GAAGACTTCT | CGCTCAGTTT | CAGTGAGGAC | ACACACAAAG | 180 |
| ACGTGGGTGA | CCATGTTGTT | TGTGGGGTGC | AGAGATGGGA | GGGGTGGGGC | CCACCCTGGA | 240 |
| AGAGTGGACA | GTGACACAAG | GTGGACACTC | TCTACAGATC | ACTGAGGATA | AGCTGGAGCC | 300 |
| ACAATGCATG | AGGCACACAC | ACAGCAAGGA | TGACNCTGTA | AACATAGCCC | ACGCTGTCCT | 360 |
| GNGGGCACTG | GGAAGCCTAN | ATNAGGCCGT | GAGCANAAAG | AAGGGGAGGA | TCCACTAGTT | 420 |
| CTANAGCGGC | CGCCACCGCG | GTGGANCTCC | ANCTTTTGTT | CCCTTTAGTG | AGGGTTAATT | 480 |
| GCGCGCTTGG | CNTAATCATG | GTCATANCTN | TTTCCTGTGT | GAAATTGTTA | TCCGCTCACA | 540 |
| ATTCCACACA | ACATACGANC | CGGAAACATA | AANTGTAAAC | CTGGGGTGCC | TAATGANTGA | 600 |
| CTAACTCACA | TTAATTGCGT | TGCGCTCACT | GCCCGCTTTC | CAATCNGGAA | ACCTGTCTTG | 660 |
| CCNCTTGCAT | TNATGAATCN | GCCAACCCCC | GGGGAAAAGC | GTTTGCGTTT | TGGGCGCTCT | 720 |
| TCCGCTTCCT | CNCTCANTTA | NTCCCTNCNC | TCGGTCATTC | CGGCTGCNGC | AAACCGGTTC | 780 |
| ACCNCCTCCA | AAGGGGGTAT | TCCGGTTTCC | CCNAATCCGG | GGANANCC | | 828 |

(2) INFORMATION FOR SEQ ID NO: 5:

(i) SEQUENCE CHARACTERISTICS:

(A) LENGTH: 834 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
TTTTTTTTTT TTTTTACTGA TAGATGGAAT TTATTAAGCT TTTCACATGT GATAGCACAT      60

AGTTTTAATT GCATCCAAAG TACTAACAAA AACTCTAGCA ATCAAGAATG GCAGCATGTT     120

ATTTTATAAC AATCAACACC TGTGGCTTTT AAAATTTGGT TTTCATAAGA TAATTTATAC     180

TGAAGTAAAT CTAGCCATGC TTTTAAAAAA TGCTTTAGGT CACTCCAAGC TTGGCAGTTA     240

ACATTTGGCA TAAACAATAA TAAAACAATC ACAATTTAAT AAATAACAAA TACAACATTG     300

TAGGCCATAA TCATATACAG TATAAGGAAA AGGTGGTAGT GTTGAGTAAG CAGTTATTAG     360

AATAGAATAC CTTGGCCTCT ATGCAAATAT GTCTAGACAC TTTGATTCAC TCAGCCCTGA     420

CATTCAGTTT TCAAAGTAGG AGACAGGTTC TACAGTATCA TTTTACAGTT CCAACACAT      480

TGAAAACAAG TAGAAAATGA TGAGTTGATT TTTATTAATG CATTACATCC TCAAGAGTTA     540

TCACCAACCC CTCAGTTATA AAAAATTTTC AAGTTATATT AGTCATATAA CTTGGTGTGC     600

TTATTTTAAA TTAGTGCTAA ATGGATTAAG TGAAGACAAC AATGGTCCCC TAATGTGATT     660

GATATTGGTC ATTTTTACCA GCTTCTAAAT CTNAACTTTC AGGCTTTTGA ACTGGAACAT     720

TGNATNACAG TGTTCCANAG TTNCAACCTA CTGGAACATT ACAGTGTGCT TGATTCAAAA     780

TGTTATTTTG TTAAAAATTA AATTTTAACC TGGTGGAAAA ATAATTTGAA ATNA           834
```

(2) INFORMATION FOR SEQ ID NO: 6:

(i) SEQUENCE CHARACTERISTICS:
        (A) LENGTH: 818 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
TTTTTTTTTT TTTTTTTTTT AAGACCCTCA TCAATAGATG GAGACATACA GAAATAGTCA      60

AACCACATCT ACAAAATGCC AGTATCAGGC GGCGGCTTCG AAGCCAAAGT GATGTTTGGA     120

TGTAAAGTGA AATATTAGTT GGCGGATGAA GCAGATAGTG AGGAAAGTTG AGCCAATAAT     180

GACGTGAAGT CCGTGGAAGC CTGTGGCTAC AAAAAATGTT GAGCCGTAGA TGCCGTCGGA     240

AATGGTGAAG GGAGACTCGA AGTACTCTGA GGCTTGTAGG AGGGTAAAAT AGAGACCCAG     300

TAAAATTGTA ATAAGCAGTG CTTGAATTAT TTGGTTTCGG TTGTTTTCTA TTAGACTATG     360

GTGAGCTCAG GTGATTGATA CTCCTGATGC GAGTAATACG GATGTGTTTA GGAGTGGGAC     420

TTCTAGGGGA TTTAGCGGGG TGATGCCTGT TGGGGCCAG TGCCCTCCTA GTTGGGGGGT      480

AGGGGCTAGG CTGGAGTGGT AAAAGGCTCA GAAAAATCCT GCGAAGAAAA AAACTTCTGA     540

GGTAATAAAT AGGATTATCC CGTATCGAAG GCCTTTTGG ACAGGTGGTG TGTGGTGGCC      600

TTGGTATGTG CTTTCTCGTG TTACATCGCG CCATCATTGG TATATGGTTA GTGTGTTGGG     660

TTANTANGGC CTANTATGAA GAACTTTTGG ANTGGAATTA AATCAATNGC TTGGCCGGAA     720

GTCATTANGA NGGCTNAAAA GGCCCTGTTA NGGGTCTGGG CTNGGTTTTA CCCNACCCAT     780

GGAATNCNCC CCCCGGACNA NTGNATCCCT ATTCTTAA                             818
```

(2) INFORMATION FOR SEQ ID NO: 7:

(i) SEQUENCE CHARACTERISTICS:
        (A) LENGTH: 817 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
TTTTTTTTTT TTTTTTTTTT TGGCTCTAGA GGGGGTAGAG GGGGTGCTAT AGGGTAAATA      60
CGGGCCCTAT TTCAAAGATT TTTAGGGGAA TTAATTCTAG GACGATGGGT ATGAAACTGT     120
GGTTTGCTCC ACAGATTTCA GAGCATTGAC CGTAGTATAC CCCCGGTCGT GTAGCGGTGA     180
AAGTGGTTTG GTTTAGACGT CCGGGAATTG CATCTGTTTT TAAGCCTAAT GTGGGACAG      240
CTCATGAGTG CAAGACGTCT TGTGATGTAA TTATTATACN AATGGGGGCT TCAATCGGGA     300
GTACTACTCG ATTGTCAACG TCAAGGAGTC GCAGGTCGCC TGGTTCTAGG AATAATGGGG     360
GAAGTATGTA GGAATTGAAG ATTAATCCGC CGTAGTCGGT GTTCTCCTAG GTTCAATACC     420
ATTGGTGGCC AATTGATTTG ATGGTAAGGG GAGGGATCGT TGAACTCGTC TGTTATGTAA     480
AGGATNCCTT NGGGATGGGA AGGCNATNAA GGACTANGGA TNAATGGCGG GCANGATATT     540
TCAAACNGTC TCTANTTCCT GAAACGTCTG AAATGTTAAT AANAATTAAN TTTNGTTATT     600
GAATNTTNNG GAAAAGGGCT TACAGGACTA GAAACCAAAT ANGAAAANTA ATNNTAANGG     660
CNTTATCNTN AAAGGTNATA ACCNCTCCTA TNATCCCACC CAATNGNATT CCCCACNCNN     720
ACNATTGGAT NCCCCANTTC CANAAANGGC CNCCCCCCGG TGNANNCCNC CTTTTGTTCC     780
CTTNANTGAN GGTTATTCNC CCCTNGCNTT ATCANCC                              817
```

(2) INFORMATION FOR SEQ ID NO: 8:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
CATTTCCGGG TTTACTTTCT AAGGAAAGCC GAGCGGAAGC TGCTAACGTG GGAATCGGTG      60
CATAAGGAGA ACTTTCTGCT GGCACGCGCT AGGGACAAGC GGGAGAGCGA CTCCGAGCGT     120
CTGAAGCGCA CGTCCCAGAA GGTGGACTTG GCACTGAAAC AGCTGGGACA CATCCGCGAG     180
TACGAACAGC GCCTGAAAGT GCTGGAGCGG GAGGTCCAGC AGTGTAGCCG CGTCCTGGGG     240
TGGGTGGCCG ANGCCTGANC CGCTCTGCCT TGCTGCCCCC ANGTGGGCCG CCACCCCCTG     300
ACCTGCCTGG GTCCAAACAC TGAGCCCTGC TGGCGGACTT CAAGGANAAC CCCCACANGG     360
GGATTTTGCT CCTANANTAA GGCTCATCTG GGCCTCGGCC CCCCCACCTG GTTGGCCTTG     420
TCTTTGANGT GAGCCCCATG TCCATCTGGG CCACTGTCNG GACCACCTTT NGGGAGTGTT     480
CTCCTTACAA CCACANNATG CCCGGCTCCT CCCGGAAACC ANTCCCANCC TGNGAAGGAT     540
CAAGNCCTGN ATCCACTNNT NCTANAACCG GCCNCCNCCG CNGTGGAACC CNCCTTNTGT     600
TCCTTTTCNT TNAGGGTTAA TNNCGCCTTG GCCTTNCCAN NGTCCTNCNC NTTTTCCNNT     660
GTTNAAATTG TTANGCNCCC NCCNNTCCCN CNNCNNCNAN CCCGACCCNN ANNTTNNANN     720
NCCTGGGGGT NCCNNCNGAT TGACCCNNCC NCCCTNTANT TGCNTTNGGG NNCNNTGCCC     780
```

```
CTTTCCCTCT NGGGANNCG                                                    799

(2) INFORMATION FOR SEQ ID NO: 9:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

ACGCCTTGAT CCTCCCAGGC TGGGACTGGT TCTGGGAGGA GCCGGGCATG CTGTGGTTTG         60

TAANGATGAC ACTCCCAAAG GTGGTCCTGA CAGTGGCCCA GATGGACATG GGGCTCACCT        120

CAAGGACAAG GCCACCAGGT GCGGGGCCG AAGCCCACAT GATCCTTACT CTATGAGCAA         180

AATCCCCTGT GGGGGCTTCT CCTTGAAGTC CGCCANCAGG GCTCAGTCTT TGGACCCANG        240

CAGGTCATGG GGTTGTNGNC CAACTGGGGG CCNCAACGCA AAANGGCNCA GGGCCTCNGN        300

CACCCATCCC ANGACGCGGC TACACTNCTG GACCTCCCNC TCCACCACTT TCATGCGCTG        360

TTCNTACCCG CGNATNTGTC CCANCTGTTT CNGTGCCNAC TCCANCTTCT NGGACGTGCG        420

CTACATACGC CCGGANTCNC NCTCCCGCTT TGTCCCTATC CACGTNCCAN CAACAAATTT        480

CNCCNTANTG CACCNATTCC CACNTTTNNC AGNTTTCCNC NNCGNGCTTC CTTNTAAAAG        540

GGTTGANCCC CGGAAAATNC CCCAAAGGGG GGGGCCNGG TACCCAACTN CCCCCTNATA        600

GCTGAANTCC CCATNACCNN GNCTCNATGG ANCCNTCCNT TTTAANNACN TTCTNAACTT        660

GGGAANANCC CTCGNCCNTN CCCCCNTTAA TCCCNCCTTG CNANGNNCNT CCCCCNNTCC        720

NCCCNNNTNG GCNTNTNANN CNAAAAAGGC CCNNNANCAA TCTCCTNNCN CCTCANTTCG        780

CCANCCCTCG AAATCGGCCN C                                                 801

(2) INFORMATION FOR SEQ ID NO: 10:

(i) SEQUENCE CHARACTERISTICS:
        (A) LENGTH: 789 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

CAGTCTATNT GGCCAGTGTG GCAGCTTTCC CTGTGGCTGC CGGTGCCACA TGCCTGTCCC         60

ACAGTGTGGC CGTGGTGACA GCTTCAGCCG CCCTCACCGG GTTCACCTTC TCAGCCCTGC        120

AGATCCTGCC CTACACACTG GCCTCCCTCT ACCACCGGGA GAAGCAGGTG TTCCTGCCCA        180

AATACCGAGG GGACACTGGA GGTGCTAGCA GTGAGGACAG CCTGATGACC AGCTTCCTGC        240

CAGGCCCTAA GCCTGGAGCT CCCTTCCCTA ATGGACACGT GGGTGCTGGA GGCAGTGGCC        300

TGCTCCCACC TCCACCCGCG CTCTGCGGGG CCTCTGCCTG TGATGTCTCC GTACGTGTGG        360

TGGTGGGTGA GCCCACCGAN GCCAGGGTGG TTCCGGGCCG GGGCATCTGC CTGGACCTCG        420

CCATCCTGGA TAGTGCTTCC TGCTGTCCCA NGTGGCCCCA TCCCTGTTTA TGGGCTCCAT        480

TGTCCAGCTC AGCCAGTCTG TCACTGCCTA TATGGTGTCT GCCGCAGGCC TGGGTCTGGT        540

CCCATTTACT TTGCTACACA GGTANTATTT GACAAGAACG ANTTGGCCAA ATACTCAGCG        600

TTAAAAAATT CCAGCAACAT TGGGGGTGGA AGGCCTGCCT CACTGGGTCC AACTCCCCGC        660

TCCTGTTAAC CCCATGGGGC TGCCGGCTTG GCCGCCAATT TCTGTTGCTG CCAAANTNAT        720
```

```
GTGGCTCTCT GCTGCCACCT GTTGCTGGCT GAAGTGCNTA CNGCNCANCT NGGGGGGTNG    780

GGNGTTCCC                                                            789
```

(2) INFORMATION FOR SEQ ID NO: 11:

(i) SEQUENCE CHARACTERISTICS:
        (A) LENGTH: 772 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
CCCACCCTAC CCAAATATTA GACACCAACA CAGAAAAGCT AGCAATGGAT TCCCTTCTAC     60

TTTGTTAAAT AAATAAGTTA AATATTTAAA TGCCTGTGTC TCTGTGATGG CAACAGAAGG    120

ACCAACAGGC CACATCCTGA TAAAAGGTAA GAGGGGGGTG GATCAGCAAA AGACAGTGC     180

TGTGGGCTGA GGGGACCTGG TTCTTGTGTG TTGCCCCTCA GGACTCTTCC CCTACAAATA    240

ACTTTCATAT GTTCAAATCC CATGGAGGAG TGTTTCATCC TAGAAACTCC CATGCAAGAG    300

CTACATTAAA CGAAGCTGCA GGTTAAGGGG CTTANAGATG GGAAACCAGG TGACTGAGTT    360

TATTCAGCTC CCAAAAACCC TTCTCTAGGT GTGTCTCAAC TAGGAGGCTA GCTGTTAACC    420

CTGAGCCTGG GTAATCCACC TGCAGAGTCC CCGCATTCCA GTGCATGGAA CCCTTCTGGC    480

CTCCCTGTAT AAGTCCAGAC TGAAACCCCC TTGGAAGGNC TCCAGTCAGG CAGCCCTANA    540

AACTGGGGAA AAAAGAAAAG GACGCCCCAN CCCCCAGCTG TGCANCTACG CACCTCAACA    600

GCACAGGGTG GCAGCAAAAA AACCACTTTA CTTTGGCACA AACAAAAACT NGGGGGGGCA    660

ACCCCGGCAC CCCNANGGGG GTTAACAGGA ANCNGGGNAA CNTGGAACCC AATTNAGGCA    720

GGCCCNCCAC CCCNAATNTT GCTGGGAAAT TTTTCCTCCC CTAAATTNTT TC            772
```

(2) INFORMATION FOR SEQ ID NO: 12:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
GCCCCAATTC CAGCTGCCAC ACCACCCACG GTGACTGCAT TAGTTCGGAT GTCATACAAA     60

AGCTGATTGA AGCAACCCTC TACTTTTTGG TCGTGAGCCT TTTGCTTGGT GCAGGTTTCA    120

TTGGCTGTGT TGGTGACGTT GTCATTGCAA CAGAATGGGG GAAAGGCACT GTTCTCTTTG    180

AAGTANGGTG AGTCCTCAAA ATCCGTATAG TTGGTGAAGC CACAGCACTT GAGCCCTTTC    240

ATGGTGGTGT TCCACACTTG AGTGAAGTCT TCCTGGGAAC CATAATCTTT CTTGATGGCA    300

GGCACTACCA GCAACGTCAG GGAAGTGCTC AGCCATTGTG GTGTACACCA AGGCGACCAC    360

AGCAGCTGCN ACCTCAGCAA TGAAGATGAN GAGGANGATG AAGAAGAACG TCNCGAGGGC    420

ACACTTGCTC TCAGTCTTAN CACCATANCA GCCCNTGAAA ACCAANANCA AAGACCACNA    480

CNCCGGCTGC GATGAAGAAA TNACCCCNCG TTGACAAACT TGCATGGCAC TGGGANCCAC    540

AGTGGCCCNA AAAATCTTCA AAAAGGATGC CCCATCNATT GACCCCCCAA ATGCCCACTG    600

CCAACAGGGG CTGCCCCACN CNCNNAACGA TGANCCNATT GNACAAGATC TNCNTGGTCT    660
```

```
TNATNAACNT GAACCCTGCN TNGTGGCTCC TGTTCAGGNC CNNGGCCTGA CTTCTNAANN     720

AANGAACTCN GAAGNCCCCA CNGGANANNC G                                    751

(2) INFORMATION FOR SEQ ID NO: 13:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GAGCCAGGCG TCCCTCTGCC TGCCCACTCA GTGGCAACAC CCGGGAGCTG TTTTGTCCTT     60

TGTGGANCCT CAGCAGTNCC CTCTTTCAGA ACTCANTGCC AAGANCCCTG AACAGGAGCC    120

ACCATGCAGT GCTTCAGCTT CATTAAGACC ATGATGATCC TCTTCAATTT GCTCATCTTT    180

CTGTGTGGTG CAGCCCTGTT GGCAGTGGGC ATCTGGGTGT CAATCGATGG GGCATCCTTT    240

CTGAAGATCT TCGGGCCACT GTCGTCCAGT GCCATGCAGT TTGTCAACGT GGGCTACTTC    300

CTCATCGCAG CCGGCGTTGT GGTCTTAGCT CTAGGTTTCC TGGGCTGCTA TGGTGCTAAG    360

ACTGAGAGCA AGTGTGCCCT CGTGACGTTC TTCTTCATCC TCCTCCTCAT CTTCATTGCT    420

GAGGTTGCAA TGCTGTGGTC GCCTTGGTGT ACACCACAAT GGCTGAGCAC TTCCTGACGT    480

TGCTGGTAAT GCCTGCCATC AANAAAAGAT TATGGGTTCC CAGGAANACT TCACTCAAGT    540

GTTGGAACAC CACCATGAAA GGGCTCAAGT GCTGTGGCTT CNNCCAACTA TACGGATTTT    600

GAAGANTCAC CTACTTCAAA GAAAANAGTG CCTTTCCCCC ATTTCTGTTG CAATTGACAA    660

ACGTCCCCAA CACAGCCAAT TGAAAACCTG CACCCAACCC AAANGGGTCC CCAACCANAA    720

ATTNAAGGG                                                            729

(2) INFORMATION FOR SEQ ID NO: 14:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

TGCTCTTCCT CAAAGTTGTT CTTGTTGCCA TAACAACCAC CATAGGTAAA GCGGGCGCAG     60

TGTTCGCTGA AGGGGTTGTA GTACCAGCGC GGGATGCTCT CCTTGCAGAG TCCTGTGTCT    120

GGCAGGTCCA CGCAGTGCCC TTTGTCACTG GGGAAATGGA TGCGCTGGAG CTCGTCAAAG    180

CCACTCGTGT ATTTTTCACA GGCAGCCTCG TCCGACGCGT CGGGGCAGTT GGGGGTGTCT    240

TCACACTCCA GGAAACTGTC NATGCAGCAG CCATTGCTGC AGCGGAACTG GGTGGGCTGA    300

CANGTGCCAG AGCACACTGG ATGGCGCCTT TCCATGNNAN GGGCCCTGNG GGAAAGTCCC    360

TGANCCCCAN ANCTGCCTCT CAAANGCCCC ACCTTGCACA CCCCGACAGG CTAGAATGGA    420

ATCTTCTTCC CGAAAGGTAG TTNTTCTTGT TGCCCAANCC ANCCCCNTAA ACAAACTCTT    480

GCANATCTGC TCCGNGGGGG TCNTANTACC ANCGTGGGAA AAGAACCCCA GGCNGCGAAC    540

CAANCTTGTT TGGATNCGAA GCNATAATCT NCTNTTCTGC TTGGTGGACA GCACCANTNA    600

CTGTNNANCT TTAGNCCNTG GTCCTCNTGG GTTGNNCTTG AACCTAATCN CCNNTCAACT    660

GGGACAAGGT AANTNGCCNT CCTTTNAATT CCCNANCNTN CCCCCTGGTT TGGGGTTTTN    720
```

```
CNCNCTCCTA CCCCAGAAAN NCCGTGTTCC CCCCCAACTA GGGGCCNAAA CCNNTTNTTC    780
CACAACCCTN CCCCACCCAC GGGTTCNGNT GGTTNG                              816
```

(2) INFORMATION FOR SEQ ID NO: 15:

(i) SEQUENCE CHARACTERISTICS:
        (A) LENGTH: 783 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

```
CCAAGGCCTG GGCAGGCATA NACTTGAAGG TACAACCCCA GGAACCCCTG GTGCTGAAGG     60
ATGTGGAAAA CACAGATTGG CGCCTACTGC GGGGTGACAC GGATGTCAGG GTAGAGAGGA   120
AAGACCCAAA CCAGGTGGAA CTGTGGGGAC TCAAGGAANG CACCTACCTG TTCCAGCTGA   180
CAGTGACTAG CTCAGACCAC CCAGAGGACA CGGCCAACGT CACAGTCACT GTGCTGTCCA   240
CCAAGCAGAC AGAAGACTAC TGCCTCGCAT CCAACAANGT GGGTCGCTGC CGGGGCTCTT   300
TCCCACGCTG GTACTATGAC CCCACGGAGC AGATCTGCAA GAGTTTCGTT TATGGAGGCT   360
GCTTGGGCAA CAAGAACAAC TACCTTCGGG AAGAAGAGTG CATTCTANCC TGTCNGGGTG   420
TGCAAGGTGG GCCTTTGANA NGCANCTCTG GGGCTCANGC GACTTTCCCC CAGGGCCCCT   480
CCATGGAAAG GCGCCATCCA NTGTTCTCTG GCACCTGTCA GCCCACCCAG TTCCGCTGCA   540
NCAATGGCTG CTGCATCNAC ANTTTCCTNG AATTGTGACA ACACCCCCCA NTGCCCCCAA   600
CCCTCCCAAC AAAGCTTCCC TGTTNAAAAA TACNCCANTT GGCTTTTNAC AAACNCCCGG   660
CNCCTCCNTT TTCCCCNNTN AACAAAGGGC NCTNGCNTTT GAACTGCCCN AACCCNGGAA   720
TCTNCCNNGG AAAAANTNCC CCCCTGGTT CCTNNAANCC CCTCCNCNAA ANCTNCCCCC   780
CCC                                                                  783
```

(2) INFORMATION FOR SEQ ID NO: 16:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

```
GCCCCAATTC CAGCTGCCAC ACCACCCACG GTGACTGCAT TAGTTCGGAT GTCATACAAA     60
AGCTGATTGA AGCAACCCTC TACTTTTTGG TCGTGAGCCT TTTGCTTGGT GCAGGTTTCA   120
TTGGCTGTGT TGGTGACGTT GTCATTGCAA CAGAATGGGG GAAAGGCACT GTTCTCTTTG   180
AAGTAGGGTG AGTCCTCAAA ATCCGTATAG TTGGTGAAGC CACAGCACTT GAGCCCTTTC   240
ATGGTGGTGT TCCACACTTG AGTGAAGTCT TCCTGGGAAC CATAATCTTT CTTGATGGCA   300
GGCACTACCA GCAACGTCAG GAAGTGCTCA GCCATTGTGG TGTACACCAA GGCGACCACA   360
GCAGCTGCAA CCTCAGCAAT GAAGATGAGG AGGAGGATGA AGAAGAACGT CNCGAGGGCA   420
CACTTGCTCT CCGTCTTAGC ACCATAGCAG CCCANGAAAC CAAGAGCAAA GACCACAACG   480
CCNGCTGCGA ATGAAAGAAA NTACCCACGT TGACAAACTG CATGGCCACT GGACGACAGT   540
TGGCCCGAAN ATCTTCAGAA AAGGGATGCC CCATCGATTG AACACCCANA TGCCCACTGC   600
```

```
CNACAGGGCT GCNCCNCNCN GAAAGAATGA GCCATTGAAG AAGGATCNTC NTGGTCTTAA      660

TGAACTGAAA CCNTGCATGG TGGCCCCTGT TCAGGGCTCT TGGCAGTGAA TTCTGANAAA      720

AAGGAACNGC NTNAGCCCCC CCAAANGANA AAACACCCCC GGGTGTTGCC CTGAATTGGC      780

GGCCAAGGAN CCCTGCCCCN G                                               801
```

(2) INFORMATION FOR SEQ ID NO: 17:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

```
GTGAGAGCCA GGCGTCCCTC TGCCTGCCCA CTCAGTGGCA ACACCCGGGA GCTGTTTTGT       60

CCTTTGTGGA GCCTCAGCAG TTCCCTCTTT CAGAACTCAC TGCCAAGAGC CCTGAACAGG      120

AGCCACCATG CAGTGCTTCA GCTTCATTAA GACCATGATG ATCCTCTTCA ATTTGCTCAT      180

CTTTCTGTGT GGTGCAGCCC TGTTGGCAGT GGGCATCTGG GTGTCAATCG ATGGGGCATC      240

CTTTCTGAAG ATCTTCGGGC CACTGTCGTC CAGTGCCATG CAGTTTGTCA ACGTGGGCTA      300

CTTCCTCATC GCAGCCGGCG TTGTGGTCTT TGCTCTTGGT TTCCTGGGCT GCTATGGTGC      360

TAAGACGGAG AGCAAGTGTG CCCTCGTGAC GTTCTTCTTC ATCCTCCTCC TCATCTTCAT      420

TGCTGAAGTT GCAGCTGCTG TGGTCGCCTT GGTGTACACC ACAATGGCTG AACCATTCCT      480

GACGTTGCTG GTANTGCCTG CCATCAANAA AGATTATGGG TTCCCAGGAA AAATTCACTC      540

AANTNTGGAA CACCNCCATG AAAAGGGCTC CAATTTCTGN TGGCTTCCCC AACTATACCG      600

GAATTTTGAA AGANTCNCCC TACTTCCAAA AAAAAANANT TGCCTTTNCC CCCNTTCTGT      660

TGCAATGAAA ACNTCCCAAN ACNGCCAATN AAAACCTGCC CNNNCAAAAA GGNTCNCAAA      720

CAAAAAAANT NNAAGGGTTN                                                 740
```

(2) INFORMATION FOR SEQ ID NO: 18:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

```
CCGCTGGTTG CGCTGGTCCA GNGNAGCCAC GAAGCACGTC AGCATACACA GCCTCAATCA       60

CAAGGTCTTC CAGCTGCCGC ACATTACGCA GGGCAAGAGC CTCCAGCAAC ACTGCATATG      120

GGATACACTT TACTTTAGCA GCCAGGGTGA CAACTGAGAG GTGTCGAAGC TTATTCTTCT      180

GAGCCTCTGT TAGTGGAGGA AGATTCCGGG CTTCAGCTAA GTAGTCAGCG TATGTCCCAT      240

AAGCAAACAC TGTGAGCAGC CGGAAGGTAG AGGCAAAGTC ACTCTCAGCC AGCTCTCTAA      300

CATTGGGCAT GTCCAGCAGT TCTCCAAACA CGTAGACACC AGNGGCCTCC AGCACCTGAT      360

GGATGAGTGT GGCCAGCGCT GCCCCCTTGG CCGACTTGGC TAGGAGCAGA AATTGCTCCT      420

GGTTCTGCCC TGTCACCTTC ACTTCCGCAC TCATCACTGC ACTGAGTGTG GGGGACTTGG      480

GCTCAGGATG TCCAGAGACG TGGTTCCGCC CCCTCNCTTA ATGACACCGN CCANNCAACC      540

GTCGGCTCCC GCCGANTGNG TTCGTCGTNC CTGGGTCAGG GTCTGCTGGC CNCTACTTGC      600
```

```
AANCTTCGTC NGGCCCATGG AATTCACCNC ACCGGAACTN GTANGATCCA CTNNTTCTAT      660

AACCGGNCGC CACCGCNNNT GGAACTCCAC TCTTNTTNCC TTTACTTGAG GGTTAAGGTC      720

ACCCTTNNCG TTACCTTGGT CCAAACCNTN CCNTGTGTCG ANATNGTNAA TCNGGNCCNA      780

TNCCANCCNC ATANGAAGCC NG
```

(2) INFORMATION FOR SEQ ID NO: 19:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

```
CNAAGCTTCC AGGTNACGGG CCGCNAANCC TGACCCNAGG TANCANAANG CAGNCNGCGG       60

GAGCCCACCG TCACGNGGNG GNGTCTTTAT NGGAGGGGGC GGAGCCACAT CNCTGGACNT      120

CNTGACCCCA ACTCCCCNCC NCNCANTGCA GTGATGAGTG CAGAACTGAA GGTNACGTGG      180

CAGGAACCAA GANCAAANNC TGCTCCNNTC CAAGTCGGCN NAGGGGCGG GGCTGGCCAC       240

GCNCATCCNT CNAGTGCTGN AAAGCCCCNN CCTGTCTACT TGTTTGGAGA ACNGCNNNGA      300

CATGCCCAGN GTTANATAAC NGGCNGAGAG TNANTTTGCC TCTCCCTTCC GGCTGCGCAN      360

CGNGTNTGCT TAGNGGACAT AACCTGACTA CTTAACTGAA CCCNNGAATC TNCCNCCCCT      420

CCACTAAGCT CAGAACAAAA AACTTCGACA CCACTCANTT GTCACCTGNC TGCTCAAGTA      480

AAGTGTACCC CATNCCCAAT GTNTGCTNGA NGCTCTGNCC TGCNTTANGT TCGGTCCTGG      540

GAAGACCTAT CAATTNAAGC TATGTTTCTG ACTGCCTCTT GCTCCCTGNA ACAANCNACC      600

CNNCNNTCCA AGGGGGGGNC GGCCCCCAAT CCCCCCAACC NTNAATTNAN TTTANCCCCN      660

CCCCCNGGCC CGGCCTTTTA CNANCNTCNN NNACNGGGNA AAACCNNNGC TTTNCCCAAC      720

NNAATCCNCC T                                                          731
```

(2) INFORMATION FOR SEQ ID NO: 20:

(i) SEQUENCE CHARACTERISTICS:
        (A) LENGTH: 754 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

```
TTTTTTTTTT TTTTTTTTTT TAAAAACCCC CTCCATTNAA TGNAAACTTC CGAAATTGTC       60

CAACCCCCTC NTCCAAATNN CCNTTTCCGG GNGGGGTTC CAAACCCAAN TTANNTTTGG      120

ANNTTAAATT AAATNTTNNT TGGNGGNNNA ANCCNAATGT NANGAAAGTT NAACCCANTA      180

TNANCTTNAA TNCCTGGAAA CCNGTNGNTT CCAAAAATNT TTAACCCTTA ANTCCCTCCG      240

AAATNGTTNA NGGAAAACCC AANTTCTCNT AAGGTTGTTT GAAGGNTNAA TNAAAANCCC      300

NNCCAATTGT TTTTNGCCAC GCCTGAATTA ATTGGNTTCC GNTGTTTTCC NTAAAAANAA      360

GGNNANCCCC GGTTANTNAA TCCCCCCNNC CCCAATTATA CCGANTTTTT TTNGAATTGG      420

GANCCCNCGG GAATTAACGG GGNNNNTCCC TNTTGGGGGG CNGGNNCCCC CCCCNTCGGG      480

GGTTNGGGNC AGGNCNNAAT TGTTTAAGGG TCCGAAAAAT CCCTCCNAGA AAAAAANCTC      540
```

```
CCAGGNTGAG NNTNGGGTTT NCCCCCCCCC CANGGCCCCT CTCGNANAGT TGGGGTTTGG       600

GGGGCCTGGG ATTTTNTTTC CCCTNTTNCC TCCCCCCCCC CCNGGGANAG AGGTTNGNGT       660

TTTGNTCNNC GGCCCCNCCN AAGANCTTTN CCGANTTNAN TTAAATCCNT GCCTNGGCGA       720

AGTCCNTTGN AGGGNTAAAN GGCCCCCTNN CGGG                                  754

(2) INFORMATION FOR SEQ ID NO: 21:

(i) SEQUENCE CHARACTERISTICS:
        (A) LENGTH: 755 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

ATCANCCCAT GACCCCNAAC NNGGGACCNC TCANCCGGNC NNNCNACCNC CGGCCNATCA        60

NNGTNAGNNC ACTNCNNTTN NATCACNCCC CNCCNACTAC GCCCNCNANC CNACGCNCTA       120

NNCANATNCC ACTGANNGCG CGANGTNGAN NGAGAAANCT NATACCANAG NCACCANACN       180

CCAGCTGTCC NANAANGCCT NNNATACNGG NNNATCCAAT NTGNANCCTC CNAAGTATTN       240

NNCNNCANAT GATTTTCCTN ANCCGATTAC CCNTNCCCCC TANCCCCTCC CCCCCAACNA       300

CGAAGGCNCT GGNCCNAAGG NNGCGNCNCC CCGCTAGNTC CCCNNCAAGT CNCNCNCCTA       360

AACTCANCCN NATTACNCGC TTCNTGAGTA TCACTCCCCG AATCTCACCC TACTCAACTC       420

AAAAANATCN GATACAAAAT AATNCAAGCC TGNTTATNAC ACTNTGACTG GGTCTCTATT       480

TTAGNGGTCC NTNAANCNTC CTAATACTTC CAGTCTNCCT TCNCCAATTT CCNAANGGCT       540

CTTTCNGACA GCATNTTTTG GTTCCCNNTT GGGTTCTTAN NGAATTGCCC TTCNTNGAAC       600

GGGCTCNTCT TTTCCTTCGG TTANCCTGGN TTCNNCCGGC CAGTTATTAT TTCCCNTTTT       660

AAATTCNTNC CNTTTANTTT TGGCNTTCNA AACCCCCGGC CTTGAAAACG GCCCCCTGGT       720

AAAAGGTTGT TTTGANAAAA TTTTTGTTTT GTTCC                                 755

(2) INFORMATION FOR SEQ ID NO: 22:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

TTTTTTTTTT TTTTTANGTG TNGTCGTGCA GGTAGAGGCT TACTACAANT GTGAANACGT        60

ACGCTNGGAN TAANGCGACC CGANTTCTAG GANNCNCCCT AAAATCANAC TGTGAAGATN       120

ATCCTGNNNA CGGAANGGTC ACCGGNNGAT NNTGCTAGGG TGNCCNCTCC CANNNCNTTN       180

CATAACTCNG NGGCCCTGCC CACCACCTTC GGCGGCCCNG NGNCCGGGCC CGGGTCATTN       240

GNNTTAACCN CACTNNGCNA NCGGTTTCCN NCCCCNNCNG ACCCNGGCGA TCCGGGGTNC       300

TCTGTCTTCC CCTGNAGNCN ANAAANTGGG CCNCGGNCCC CTTTACCCCT NNACAAGCCA       360

CNGCCNTCTA NCCNCNGCCC CCCCTCCANT NNGGGGGACT GCCNANNGCT CCGTTNCTNG       420

NNACCCCNNN GGGTNCCTCG GTTGTCGANT CNACCGNANG CCANGGATTC CNAAGGAAGG       480

TGCGTTNTTG GCCCCTACCC TTCGCTNCGG NNCACCCTTC CCGACNANGA NCCGCTCCCG       540

CNCNNCGNNG CCTCNCCTCG CAACACCCGC NCTCNTCNGT NCGGNNNCCC CCCCACCCGC       600
```

```
NCCCTCNCNC NGNCGNANCN CTCCNCCNCC GTCTCANNCA CCACCCCGCC CCGCCAGGCC      660

NTCANCCACN GGNNGACNNG NAGCNCNNTC GCNCCGCGCN GCGNCNCCCT CGCCNCNGAA      720

CTNCNTCNGG CCANTNNCGC TCAANCCNNA CNAAACGCCG CTGCGCGGCC CGNAGCGNCC      780

NCCTCCNCGA GTCCTCCCGN CTTCCNACCC ANGNNTTCCN CGAGGACACN NNACCCCGCC      840

NNCANGCGG                                                             849

(2) INFORMATION FOR SEQ ID NO: 23:

(i) SEQUENCE CHARACTERISTICS:
        (A) LENGTH: 872 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

GCGCAAACTA TACTTCGCTC GNACTCGTGC GCCTCGCTNC TCTTTTCCTC CGCAACCATG       60

TCTGACNANC CCGATTNGGC NGATATCNAN AAGNTCGANC AGTCCAAACT GANTAACACA      120

CACACNCNAN AGANAAATCC NCTGCCTTCC ANAGTANACN ATTGAACNNG AGAACCANGC      180

NGGCGAATCG TAATNAGGCG TGCGCCGCCA ATNTGTCNCC GTTTATTNTN CCAGCNTCNC      240

CTNCCNACCC TACNTCTTCN NAGCTGTCNN ACCCCTNGTN CGNACCCCCC NAGGTCGGGA      300

TCGGGTTTNN NNTGACCGNG CNNCCCCTCC CCCCNTCCAT NACGANCCNC CCGCACCACC      360

NANNGCNCGC NCCCCGNNCT CTTCGCCNCC CTGTCCTNTN CCCCTGTNGC CTGGCNCNGN      420

ACCGCATTGA CCCTCGCCNN CTNCNNGAAA NCGNANACGT CCGGGTTGNN ANNANCGCTG      480

TGGGNNNGCG TCTGCNCCGC GTTCCTTCCN NCNNCTTCCA CCATCTTCNT TACNGGGTCT      540

CCNCGCCNTC TCNNNCACNC CCTGGGACGC TNTCCTNTGC CCCCCTTNAC TCCCCCCCTT      600

CGNCGTGNCC CGNCCCCACC NTCATTTNCA NACGNTCTTC ACAANNNCCT GGNTNNCTCC      660

CNANCNGNCN GTCANCCNAG GGAAGGGNGG GGNNCCNNTG NTTGACGTTG NGGNGANGTC      720

CGAANANTCC TCNCCNTCAN CNCTACCCCT CGGGCGNNCT CTCNGTTNCC AACTTANCAA      780

NTCTCCCCCG NGNGCNCNTC TCAGCCTCNC CCNCCCCNCT CTCTGCANTG TNCTCTGCTC      840

TNACCNNTAC GANTNTTCGN CNCCCTCTTT CC                                   872

(2) INFORMATION FOR SEQ ID NO: 24:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GCATGCAAGC TTGAGTATTC TATAGNGTCA CCTAAATANC TTGGCNTAAT CATGGTCNTA       60

NCTGNCTTCC TGTGTCAAAT GTATACNAAN TANATATGAA TCTNATNTGA CAAGANNGTA      120

TCNTNCATTA GTAACAANTG TNNTGTCCAT CCTGTCNGAN CANATTCCCA TNNATTNCGN      180

CGCATTCNCN GCNCANTATN TAATNGGGAA NTCNNNTNNN NCACCNNCAT CTATCNTNCC      240

GCNCCCTGAC TGGNAGAGAT GGATNANTTC TNNTNTGACC NACATGTTCA TCTTGGATTN      300

AANANCCCCC CGCNGNCCAC CGGTTNGNNG CNAGCCNNTC CCAAGACCTC CTGTGGAGGT      360
```

```
AACCTGCGTC AGANNCATCA AACNTGGGAA ACCCGCNNCC ANGTNNAAGT NGNNNCANAN    420

GATCCCGTCC AGGNTTNACC ATCCCTTCNC AGCGCCCCCT TTNGTGCCTT ANAGNGNAGC    480

GTGTCCNANC CNCTAACAT GANACGCGCC AGNCCANCCG CAATTNGGCA CAATGTCGNC     540

GAACCCCCTA GGGGGANTNA TNCAAANCCC CAGGATTGTC CNCNCANGAA ATCCCNCANC    600

CCCNCCCTAC CCNNCTTTGG GACNGTGACC AANTCCCGGA GTNCCAGTCC GGCCNGNCTC    660

CCCCACCGGT NNCCNTGGGG GGGTGAANCT CNGNNTCANC CNGNCGAGGN NTCGNAAGGA    720

ACCGGNCCTN GGNCGAANNG ANCNNTCNGA AGNGCCNCNT CGTATAACCC CCCCTCNCCA    780

NCCNACNGNT AGNTCCCCCC CNGGGTNCGG AANGG                               815

(2) INFORMATION FOR SEQ ID NO: 25:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

CCGAGATGTC TCGCTCCGTG GCCTTAGCTG TGCTCGCGCT ACTCTCTCTT TCTGGCCTGG     60

AGGCTATCCA GCGTACTCCA AAGATTCAGG TTTACTCACG TCATCCAGCA GAGAATGGAA    120

AGTCAAATTT CCTGAATTGC TATGTGTCTG GGTTTCATCC ATCCGACATT GAANTTGACT    180

TACTGAAGAA TGGANAGAGA ATTGAAAAAG TGGAGCATTC AGACTTGTCT TTCAGCAAGG    240

ACTGGTCTTT CTATCTCNTG TACTACACTG AATTCACCCC CACTGAAAAA GATGAGTATG    300

CCTGCCGTGT GAACCATGTG ACTTTGTCAC AGCCCAAGAT AGTTAAGTGG GATCGAGACA    360

TGTAAGCAGN CNNCATGGAA GTTTGAAGAT GCCGCATTTG GATTGGATGA ATTCCAAATT    420

CTGCTTGCTT GCNTTTTAAT ANTGATATGC NTATACACCC TACCCTTTAT GNCCCCAAAT    480

TGTAGGGGTT ACATNANTGT TCNCNTNGGA CATGGATCTTC CTTTATAANT CCNCCNTTCG   540

AATTGCCCGT CNCCCNGTTN NGAATGTTTC CNNAACCACG GTTGGCTCCC CCAGGTCNCC    600

TCTTACGGAA GGGCCTGGGC CNCTTTNCAA GGTTGGGGGA ACCNAAAATT TCNCTTNTGC    660

CCNCCCNCCA CNNTCTTGNG NNCNCANTTT GGAACCCTTC CNATTCCCCT TGGCCTCNNA    720

NCCTTNNCTA ANAAAACTTN AAANCGTNGC NAAANNTTTN ACTTCCCCCC TTACC         775

(2) INFORMATION FOR SEQ ID NO: 26:

(i) SEQUENCE CHARACTERISTICS:
        (A) LENGTH: 820 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

ANATTANTAC AGTGTAATCT TTTCCCAGAG GTGTGTANAG GGAACGGGGC CTAGAGGCAT     60

CCCANAGATA NCTTATANCA ACAGTGCTTT GACCAAGAGC TGCTGGGCAC ATTTCCTGCA    120

GAAAAGGTGG CGGTCCCCAT CACTCCTCCT CTCCCATAGC CATCCCAGAG GGGTGAGTAG    180

CCATCANGCC TTCGGTGGGA GGGAGTCANG GAAACAACAN ACCACAGAGC ANACAGACCA    240

NTGATGACCA TGGGCGGGAG CGAGCCTCTT CCCTGNACCG GGGTGGCANA NGANAGCCTA    300

NCTGAGGGGT CACACTATAA ACGTTAACGA CCNAGATNAN CACCTGCTTC AAGTGCACCC    360
```

```
TTCCTACCTG ACNACCAGNG ACCNNNAACT GCNGCCTGGG GACAGCNCTG GGANCAGCTA    420

ACNNAGCACT CACCTGCCCC CCCATGGCCG TNCGCNTCCC TGGTCCTGNC AAGGGAAGCT    480

CCCTGTTGGA ATTNCGGGGA NACCAAGGGA NCCCCCTCCT CCANCTGTGA AGGAAAAANN    540

GATGGAATTT TNCCCTTCCG GCCNNTCCCC TCTTCCTTTA CACGCCCCCT NNTACTCNTC    600

TCCCTCTNTT NTCCTGNCNC ACTTTTNACC CCNNNATTTC CCTTNATTGA TCGGANNCTN    660

GANATTCCAC TNNCGCCTNC CNTCNATCNG NAANACNAAA NACTNTCTNA CCCNGGGGAT    720

GGGNNCCTCG NTCATCCTCT CTTTTTCNCT ACCNCCNNTT CTTTGCCTCT CCTTNGATCA    780

TCCAACCNTC GNTGGCCNTN CCCCCCCNNN TCCTTTNCCC                          820

(2) INFORMATION FOR SEQ ID NO: 27:

(i) SEQUENCE CHARACTERISTICS:
        (A) LENGTH: 818 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

TCTGGGTGAT GGCCTCTTCC TCCTCAGGGA CCTCTGACTG CTCTGGGCCA AAGAATCTCT     60

TGTTTCTTCT CCGAGCCCCA GGCAGCGGTG ATTCAGCCCT GCCCAACCTG ATTCTGATGA    120

CTGCGGATGC TGTGACGGAC CCAAGGGGCA AATAGGGTCC CAGGGTCCAG GGAGGGGCGC    180

CTGCTGAGCA CTTCCGCCCC TCACCCTGCC CAGCCCCTGC CATGAGCTCT GGGCTGGGTC    240

TCCGCCTCCA GGGTTCTGCT CTTCCANGCA NGCCANCAAG TGGCGCTGGG CCACACTGGC    300

TTCTTCCTGC CCCNTCCCTG GCTCTGANTC TCTGTCTTCC TGTCCTGTGC ANGCNCCTTG    360

GATCTCAGTT TCCCTCNCTC ANNGAACTCT GTTTCTGANN TCTTCANTTA ACTNTGANTT    420

TATNACCNAN TGGNCTGTNC TGTCNNACTT TAATGGGCCN GACCGGCTAA TCCCTCCCTC    480

NCTCCCTTCC ANTTCNNNNA ACCNGCTTNC CNTCNTCTCC CCNTANCCCG CCNGGGAANC    540

CTCCTTTGCC CTNACCANGG GCCNNNACCG CCCNTNNCTN GGGGGGCNNG GTNNCTNCNC    600

CTGNTNNCCC CNCTCNCNNT TNCCTCGTCC CNNCNNCGCN NNGCANNTTC NCNGTCCCNN    660

TNNCTCTTCN NGTNTCGNAA NGNTCNCNTN TNNNNNGNCN NGNTNNTNCN TCCCTCTCNC    720

CNNNTGNANG TNNTTNNNNC NCNGNNCCCC NNNNCNNNNN NGGNNNTNNN TCTNCNCNGC    780

CCCNNCCCCC NGNATTAAGG CCTCCNNTCT CCGGCCNC                            818

(2) INFORMATION FOR SEQ ID NO: 28:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

AGGAAGGGCG GAGGGATATT GTANGGGATT GAGGGATAGG AGNATAANGG GGGAGGTGTG     60

TCCCAACATG ANGGTGNNGT TCTCTTTTGA ANGAGGGTTG NGTTTTTANN CCNGGTGGGT    120

GATTNAACCC CATTGTATGG AGNNAAAGGN TTTNAGGGAT TTTTCGGCTC TTATCAGTAT    180

NTANATTCCT GTNAATCGGA AAATNATNTT TCNNCNGGAA AATNTTGCTC CCATCCGNAA    240
```

```
ATTNCTCCCG GGTAGTGCAT NTTNGGGGGN CNGCCANGTT TCCCAGGCTG CTANAATCGT      300

ACTAAAGNTT NAAGTGGGAN TNCAAATGAA AACCTNNCAC AGAGNATCCN TACCCGACTG      360

TNNNTTNCCT TCGCCCTNTG ACTCTGCNNG AGCCCAATAC CCNNGNGNAT GTCNCCCNGN      420

NNNGCGNCNC TGAAANNNNC TCGNGGCTNN GANCATCANG GGGTTTCGCA TCAAAAGCNN      480

CGTTTCNCAT NAAGGCACTT TNGCCTCATC CAACCNCTNG CCCTCNNCCA TTTNGCCGTC      540

NGGTTCNCCT ACGCTNNTNG CNCCTNNNTN GANATTTTNC CCGCCTNGGG NAANCCTCCT      600

GNAATGGGTA GGGNCTTNTC TTTTNACCNN GNGGTNTACT AATCNNCTNC ACGCNTNCTT      660

TCTCNACCCC CCCCCTTTTT CAATCCCANC GGCNAATGGG GTCTCCCCNN CGANGGGGGG      720

NNNCCCANNC C                                                          731

(2) INFORMATION FOR SEQ ID NO: 29:

(i) SEQUENCE CHARACTERISTICS:
        (A) LENGTH: 822 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

ACTAGTCCAG TGTGGTGGAA TTCCATTGTG TTGGGGNCNC TTCTATGANT ANTNTTAGAT       60

CGCTCANACC TCACANCCTC CCNACNANGC CTATAANGAA NANNAATAGA NCTGTCNNNT      120

ATNTNTACNC TCATANNCCT CNNNACCCAC TCCCTCTTAA CCCNTACTGT GCCTATNGCN      180

TNNCTANTCT NTGCCGCCTN CNANCCACCN GTGGGCCNAC CNCNNGNATT CTCNATCTCC      240

TCNCCATNTN GCCTANANTA NGTNCATACC CTATACCTAC NCCAATGCTA NNNCTAANCN      300

TCCATNANTT ANNNTAACTA CCACTGACNT NGACTTTCNC ATNANCTCCT AATTTGAATC      360

TACTCTGACT CCCACNGCCT ANNNATTAGC ANCNTCCCCC NACNATNTCT CAACCAAATC      420

NTCAACAACC TATCTANCTG TTCNCCAACC NTTNCCTCCG ATCCCCNNAC AACCCCCCTC      480

CCAAATACCC NCCACCTGAC NCCTAACCCN CACCATCCCG GCAAGCCNAN GGNCATTTAN      540

CCACTGGAAT CACNATNGGA NAAAAAAAAC CCNAACTCTC TANCNCNNAT CTCCCTAANA      600

AATNCTCCTN NAATTTACTN NCANTNCCAT CAANCCCACN TGAAACNNAA CCCCTGTTTT      660

TANATCCCTT CTTTCGAAAA CCNACCCTTT ANNNCCCAAC CTTTNGGGCC CCCCCNCTNC      720

CCNAATGAAG GNCNCCCAAT CNANGAAACG NCCNTGAAAA ANCNAGGCNA ANANNNTCCG      780

CANATCCTAT CCCTTANTTN GGGGNCCCTT NCCCNGGGCC CC                        822

(2) INFORMATION FOR SEQ ID NO: 30:

(i) SEQUENCE CHARACTERISTICS:
        (A) LENGTH: 787 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

CGGCCGCCTG CTCTGGCACA TGCCTCCTGA ATGGCATCAA AAGTGATGGA CTGCCCATTG       60

CTAGAGAAGA CCTTCTCTCC TACTGTCATT ATGGAGCCCT GCAGACTGAG GGCTCCCCTT      120

GTCTGCAGGA TTTGATGTCT GAAGTCGTGG AGTGTGGCTT GGAGCTCCTC ATCTACATNA      180

GCTGGAAGCC CTGGAGGGCC TCTCTCGCCA GCCTCCCCCT TCTCTCCACG CTCTCCANGG      240
```

```
ACACCAGGGG CTCCAGGCAG CCCATTATTC CCAGNANGAC ATGGTGTTTC TCCACGCGGA      300

CCCATGGGGC CTGNAAGGCC AGGGTCTCCT TTGACACCAT CTCTCCCGTC CTGCCTGGCA      360

GGCCGTGGGA TCCACTANTT CTANAACGGN CGCCACCNCG GTGGGAGCTC CAGCTTTTGT      420

TCCCNTTAAT GAAGGTTAAT TGCNCGCTTG GCGTAATCAT NGGTCANAAC TNTTTCCTGT      480

GTGAAATTGT TTNTCCCCTC NCNATTCCNC NCNACATACN AACCCGGAAN CATAAAGTGT      540

TAAAGCCTGG GGGTNGCCTN NNGAATNAAC TNAACTCAAT TAATTGCGTT GGCTCATGGC      600

CCGCTTTCCN TTCNGGAAAA CTGTCNTCCC CTGCNTTNNT GAATCGGCCA CCCCCCNGGG      660

AAAAGCGGTT TGCNTTTTNG GGGGNTCCTT CCNCTTCCCC CCTCNCTAAN CCCTNCGCCT      720

CGGTCGTTNC NGGTNGCGGG GAANGGGNAT NNNCTCCCNC NAAGGGGGNG AGNNNGNTAT      780

CCCCAAA                                                                787

(2) INFORMATION FOR SEQ ID NO: 31:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

TTTTTTTTTT TTTTTTGGC GATGCTACTG TTTAATTGCA GGAGGTGGGG GTGTGTGTAC        60

CATGTACCAG GGCTATTAGA AGCAAGAAGG AAGGAGGGAG GGCAGAGCGC CCTGCTGAGC      120

AACAAAGGAC TCCTGCAGCC TTCTCTGTCT GTCTCTTGGC GCAGGCACAT GGGGAGGCCT      180

CCCGCAGGGT GGGGGCCACC AGTCCAGGGG TGGGAGCACT ACANGGGGTG GGAGTGGGTG      240

GTGGCTGGTN CNAATGGCCT GNCACANATC CCTACGATTC TTGACACCTG GATTTCACCA      300

GGGGACCTTC TGTTCTCCCA NGGNAACTTC NTNNATCTCN AAAGAACACA ACTGTTTCTT      360

CNGCANTTCT GGCTGTTCAT GGAAAGCACA GGTGTCCNAT TTNGGCTGGG ACTTGGTACA      420

TATGGTTCCG GCCCACCTCT CCCNTCNAAN AAGTAATTCA CCCCCCCCN CCNTCTNTTG      480

CCTGGGCCCT TAANTACCCA CACCGGAACT CANTTANTTA TTCATCTTNG GNTGGGCTTG      540

NTNATCNCCN CCTGAANGCG CCAAGTTGAA AGGCCACGCC GTNCCNCTC CCCATAGNAN       600

NTTTTNNCNT CANCTAATGC CCCCCNGGC AACNATCCAA TCCCCCCCN TGGGGCCCC        660

AGCCCANGGC CCCCGNCTCG GGNNNCCNGN CNCGNANTCC CCAGGNTCTC CCANTCNGNC      720

CCNNNGCNCC CCCGCACGCA GAACANAAGG NTNGAGCCNC CGCANNNNNN NGGTNNCNAC      780

CTCGCCCCCC CCNNCGNNG                                                   799

(2) INFORMATION FOR SEQ ID NO: 32:

(i) SEQUENCE CHARACTERISTICS:
        (A) LENGTH: 789 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

TTTTTTTTTT TTTTTTTTTT TTTTTTTTTT TTTTTTTTTT TTTTTTTTTT TTTTTTTTT        60

TTTTNCCNAG GGCAGGTTTA TTGACAACCT CNCGGGACAC AANCAGGCTG GGGACAGGAC     120
```

-continued

```
GGCAACAGGC TCCGGCGGCG GCGGCGGCGG CCCTACCTGC GGTACCAAAT NTGCAGCCTC      180

CGCTCCCGCT TGATNTTCCT CTGCAGCTGC AGGATGCCNT AAAACAGGGC CTCGGCCNTN      240

GGTGGGCACC CTGGGATTTN AATTTCCACG GGCACAATGC GGTCGCANCC CCTCACCACC      300

NATTAGGAAT AGTGGTNTTA CCCNCCNCCG TTGGCNCACT CCCCNTGGAA ACCACTTNTC      360

GCGGCTCCGG CATCTGGTCT TAAACCTTGC AAACNCTGGG GCCCTCTTTT TGGTTANTNT      420

NCCNGCCACA ATCATNACTC AGACTGGCNC GGGCTGGCCC CAAAAAANCN CCCCAAAACC      480

GGNCCATGTC TTNNCGGGGT TGCTGCNATN TNCATCACCT CCCGGGCNCA NCAGGNCAAC      540

CCAAAAGTTC TTGNGGCCCN CAAAAAANCT CCGGGGGGNC CCAGTTTCAA CAAAGTCATC      600

CCCCTTGGCC CCCAAATCCT CCCCCCGNTT NCTGGGTTTG GGAACCCACG CCTCTNNCTT      660

TGGNNGGCAA GNTGGNTCCC CCTTCGGGCC CCCGGTGGGC CCNNCTCTAA NGAAAACNCC      720

NTCCTNNNCA CCATCCCCCC NNGNNACGNC TANCAANGNA TCCCTTTTTT TANAAACGGG      780

CCCCCCNCG                                                              789
```

(2) INFORMATION FOR SEQ ID NO: 33:

(i) SEQUENCE CHARACTERISTICS:
        (A) LENGTH: 793 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

```
GACAGAACAT GTTGGATGGT GGAGCACCTT TCTATACGAC TTACAGGACA GCAGATGGGG       60

AATTCATGGC TGTTGGAGCA ATANAACCCC AGTTCTACGA GCTGCTGATC AAAGGACTTG      120

GACTAAAGTC TGATGAACTT CCCAATCAGA TGAGCATGGA TGATTGGCCA GAAATGAANA      180

AGAAGTTTGC AGATGTATTT GCAAAGAAGA CGAAGGCAGA GTGGTGTCAA ATCTTTGACG      240

GCACAGATGC CTGTGTGACT CCGGTTCTGA CTTTTGAGGA GGTTGTTCAT CATGATCACA      300

ACAANGAACG GGGCTCGTTT ATCACCANTG AGGAGCAGGA CGTGAGCCCC CGCCCTGCAC      360

CTCTGCTGTT AAACACCCCA GCCATCCCTT CTTTCAAAAG GGATCCACTA CTTCTAGAGC      420

GGNCGCCACC GCGGTGGAGC TCCAGCTTTT GTTCCCTTTA GTGAGGGTTA ATTGCGCGCT      480

TGGCGTAATC ATGGTCATAN CTGTTTCCTG TGTGAAATTG TTATCCGCTC ACAATTCCAC      540

ACAACATACG ANCCGGAAGC ATNAAATTTT AAAGCCTGGN GGTNGCCTAA TGANTGAACT      600

NACTCACATT AATTGGCTTT GCGCTCACTG CCCGCTTTCC AGTCCGGAAA ACCTGTCCTT      660

GCCAGCTGCC NTTAATGAAT CNGGCCACCC CCCGGGGAAA AGGCNGTTTG CTTNTTGGGG      720

CGCNCTTCCC GCTTTCTCGC TTCCTGAANT CCTTCCCCCC GGTCTTTCGG CTTGCGGCNA      780

ACGGTATCNA CCT                                                         793
```

(2) INFORMATION FOR SEQ ID NO: 34:

(i) SEQUENCE CHARACTERISTICS:
        (A) LENGTH: 756 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

```
GCCGCGACCG GCATGTACGA GCAACTCAAG GGCGAGTGGA ACCGTAAAAG CCCCAATCTT       60
```

```
ANCAAGTGCG GGGAANAGCT GGGTCGACTC AAGCTAGTTC TTCTGGAGCT CAACTTCTTG      120

CCAACCACAG GGACCAAGCT GACCAAACAG CAGCTAATTC TGGCCCGTGA CATACTGGAG      180

ATCGGGGCCC AATGGAGCAT CCTACGCAAN GACATCCCCT CCTTCGAGCG CTACATGGCC      240

CAGCTCAAAT GCTACTACTT TGATTACAAN GAGCAGCTCC CCGAGTCAGC CTATATGCAC      300

CAGCTCTTGG GCCTCAACCT CCTCTTCCTG CTGTCCCAGA ACCGGGTGGC TGANTNCCAC      360

ACGGANTTGG ANCGGCTGCC TGCCCAANGA CATACANACC AATGTCTACA TCNACCACCA      420

GTGTCCTGGA GCAATACTGA TGGANGGCAG CTACCNCAAA GTNTTCCTGG CCNAGGGTAA      480

CATCCCCCGC CGAGAGCTAC ACCTTCTTCA TTGACATCCT GCTCGACACT ATCAGGGATG      540

AAAATCGCNG GGTTGCTCCA GAAAGGCTNC AANAANATCC TTTTCNCTGA AGGCCCCCGG      600

ATNCNCTAGT NCTAGAATCG GCCCGCCATC GCGGTGGANC CTCCAACCTT TCGTTNCCCT      660

TTACTGAGGG TTNATTGCCG CCCTTGGCGT TATCATGGTC ACNCCNGTTN CCTGTGTTGA      720

AATTNTTAAC CCCCCACAAT TCCACGCCNA CATTNG                               756
```

(2) INFORMATION FOR SEQ ID NO: 35:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

```
GGGGATCTCT ANATCNACCT GNATGCATGG TTGTCGGTGT GGTCGCTGTC GATGAANATG       60

AACAGGATCT TGCCCTTGAA GCTCTCGGCT GCTGTNTTTA AGTTGCTCAG TCTGCCGTCA      120

TAGTCAGACA CNCTCTTGGG CAAAAAACAN CAGGATNTGA GTCTTGATTT CACCTCCAAT      180

AATCTTCNGG GCTGTCTGCT CGGTGAACTC GATGACNANG GGCAGCTGGT TGTGTNTGAT      240

AAANTCCANC ANGTTCTCCT TGGTGACCTC CCCTTCAAAG TTGTTCCGGC CTTCATCAAA      300

CTTCTNNAAN ANGANNANCC CANCTTTGTC GAGCTGGNAT TTGGANAACA CGTCACTGTT      360

GGAAACTGAT CCCAAATGGT ATGTCATCCA TCGCCTCTGC TGCCTGCAAA AAACTTGCTT      420

GGCNCAAATC CGACTCCCCN TCCTTGAAAG AAGCCNATCA CACCCCCCTC CCTGGACTCC      480

NNCAANGACT CTNCCGCTNC CCCNTCCNNG CAGGGTTGGT GGCANNCCGG GCCCNTGCGC      540

TTCTTCAGCC AGTTCACNAT NTTCATCAGC CCCTCTGCCA GCTGTTNTAT TCCTTGGGGG      600

GGAANCCGTC TCTCCCTTCC TGAANNAACT TTGACCGTNG GAATAGCCGC GCNTCNCCNT      660

ACNTNCTGGG CCGGGTTCAA ANTCCCTCCN TTGNCNNTCN CCTCGGGCCA TTCTGGATTT      720

NCCNAACTTT TTCCTTCCCC CNCCCCNCGG NGTTTGGNTT TTTCATNGGG CCCCAACTCT      780

GCTNTTGGCC ANTCCCCTGG GGGCNTNTAN CNCCCCCTNT GGTCCCNTNG GGCC           834
```

(2) INFORMATION FOR SEQ ID NO: 36:

(i) SEQUENCE CHARACTERISTICS:
        (A) LENGTH: 814 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

```
CGGNCGCTTT CCNGCCGCGC CCCGTTTCCA TGACNAAGGC TCCCTTCANG TTAAATACNN      60

CCTAGNAAAC ATTAATGGGT TGCTCTACTA ATACATCATA CNAACCAGTA AGCCTGCCCA     120

NAACGCCAAC TCAGGCCATT CCTACCAAAG GAAGAAAGGC TGGTCTCTCC ACCCCCTGTA     180

GGAAAGGCCT GCCTTGTAAG ACACCACAAT NCGGCTGAAT CTNAAGTCTT GTGTTTTACT     240

AATGGAAAAA AAAATAAAC AANAGGTTTT GTTCTCATGG CTGCCCACCG CAGCCTGGCA      300

CTAAAACANC CCAGCGCTCA CTTCTGCTTG GANAAATATT CTTTGCTCTT TTGGACATCA     360

GGCTTGATGG TATCACTGCC ACNTTTCCAC CCAGCTGGGC NCCCTTCCCC CATNTTTGTC     420

ANTGANCTGG AAGGCCTGAA NCTTAGTCTC CAAAAGTCTC NGCCCACAAG ACCGGCCACC     480

AGGGGANGTC NTTTNCAGTG GATCTGCCAA ANANTACCCN TATCATCNNT GAATAAAAAG     540

GCCCCTGAAC GANATGCTTC CANCANCCTT TAAGACCCAT AATCCTNGAA CCATGGTGCC     600

CTTCCGGTCT GATCCNAAAG GAATGTTCCT GGGTCCCANT CCCTCCTTTG TTNCTTACGT     660

TGTNTTGGAC CCNTGCTNGN ATNACCCAAN TGANATCCCC NGAAGCACCC TNCCCCTGGC     720

ATTTGANTTT CNTAAATTCT CTGCCCTACN NCTGAAAGCA CNATTCCCTN GGCNCCNAAN    780

GGNGAACTCA AGAAGGTCTN NGAAAAACCA CNCN                                814

(2) INFORMATION FOR SEQ ID NO: 37:

(i) SEQUENCE CHARACTERISTICS:
        (A) LENGTH: 760 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

GCATGCTGCT CTTCCTCAAA GTTGTTCTTG TTGCCATAAC AACCACCATA GGTAAAGCGG      60

GCGCAGTGTT CGCTGAAGGG GTTGTAGTAC CAGCGCGGGA TGCTCTCCTT GCAGAGTCCT     120

GTGTCTGGCA GGTCCACGCA ATGCCCTTTG TCACTGGGGA AATGGATGCG CTGGAGCTCG     180

TCNAANCCAC TCGTGTATTT TTCACANGCA GCCTCCTCCG AAGCNTCCGG GCAGTTGGGG     240

GTGTCGTCAC ACTCCACTAA ACTGTCGATN CANCAGCCCA TTGCTGCAGC GGAACTGGGT     300

GGGCTGACAG GTGCCAGAAC ACACTGGATN GGCCTTTCCA TGGAAGGGCC TGGGGGAAAT     360

CNCCTNANCC CAAACTGCCT CTCAAAGGCC ACCTTGCACA CCCCGACAGG CTAGAAATGC     420

ACTCTTCTTC CCAAAGGTAG TTGTTCTTGT TGCCCAAGCA NCCTCCANCA AACCAAAANC     480

TTGCAAAATC TGCTCCGTGG GGGTCATNNN TACCANGGTT GGGGAAANAA ACCCGGCNGN     540

GANCCNCCTT GTTTGAATGC NAAGGNAATA ATCCTCCTGT CTTGCTTGGG TGGAANAGCA     600

CAATTGAACT GTTAACNTTG GGCCGNGTTC CNCTNGGGTG GTCTGAAACT AATCACCGTC     660

ACTGGAAAAA GGTANGTGCC TTCCTTGAAT TCCCAAANTT CCCCTNGNTT TGGGTNNTTT     720

CTCCTCTNCC CTAAAAATCG TNTTCCCCCC CCNTANGGCG                           760

(2) INFORMATION FOR SEQ ID NO: 38:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:
```

```
TTTTTTTTTT TTTTTTTTTT TTTTTTTTTT TTTTTAAAAA CCCCCTCCAT TGAATGAAAA    60

CTTCCNAAAT TGTCCAACCC CCTCNNCCAA ATNNCCATTT CCGGGGGGGG GTTCCAAACC   120

CAAATTAATT TTGGANTTTA AATTAAATNT TNATTNGGGG AANAANCCAA ATGTNAAGAA   180

AATTTAACCC ATTATNAACT TAAATNCCTN GAAACCCNTG GNTTCCAAAA ATTTTTAACC   240

CTTAAATCCC TCCGAAATTG NTAANGGAAA ACCAAATTCN CCTAAGGCTN TTTGAAGGTT   300

NGATTTAAAC CCCCTTNANT TNTTTTNACC CNNGNCTNAA NTATTTNGNT TCCGGTGTTT   360

TCCTNTTAAN CNTNGGTAAC TCCCGNTAAT GAANNNCCCT AANCCAATTA AACCGAATTT   420

TTTTTGAATT GGAAATTCCN NGGGAATTNA CCGGGGTTTT TCCCNTTTGG GGGCCATNCC   480

CCCNCTTTCG GGGTTTGGGN NTAGGTTGAA TTTTTNNANG NCCCAAAAAA NCCCCCAANA   540

AAAAAACTCC CAAGNNTTAA TTNGAATNTC CCCCTTCCCA GGCCTTTTGG GAAAGGNGGG   600

TTTNTGGGGG CCNGGGANTT CNTTCCCCCN TTNCCNCCCC CCCCCCNGGT AAANGGTTAT   660

NGNNTTTGGT TTTTGGGCCC CTTNANGGAC CTTCCGGATN GAAATTAAAT CCCCGGGNCG   720

GCCG                                                                724

(2) INFORMATION FOR SEQ ID NO: 39:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

TTTTTTTTTT TTTTTCTTTG CTCACATTTA ATTTTTATTT TGATTTTTTT TAATGCTGCA    60

CAACACAATA TTTATTTCAT TTGTTTCTTT TATTTCATTT TATTTGTTTG CTGCTGCTGT   120

TTTATTTATT TTTACTGAAA GTGAGAGGGA ACTTTTGTGG CCTTTTTTCC TTTTTCTGTA   180

GGCCGCCTTA AGCTTTCTAA ATTTGGAACA TCTAAGCAAG CTGAANGGAA AAGGGGGTTT   240

CGCAAAATCA CTCGGGGGAA NGGAAAGGTT GCTTTGTTAA TCATGCCCTA TGGTGGGTGA   300

TTAACTGCTT GTACAATTAC NTTTCACTTT TAATTAATTG TGCTNAANGC TTTAATTANA   360

CTTGGGGGTT CCCTCCCCAN ACCAACCCCN CTGACAAAAA GTGCCNGCCC TCAAATNATG   420

TCCCGGCNNT CNTTGAAACA CACNGCNGAA NGTTCTCATT NTCCCNCNC CAGGTNAAAA   480

TGAAGGGTTA CCATNTTTAA CNCCACCTCC ACNTGGCNNN GCCTGAATCC TCNAAAANCN   540

CCCTCAANCN AATTNCTNNG CCCCGGTCNC GCNTNNGTCC CNCCCGGGCT CCGGGAANTN   600

CACCCCCNGA ANNCNNTNNC NAACNAAATT CCGAAAATAT TCCCNNTCNC TCAATTCCCC   660

CNNAGACTNT CCTCNNCNAN CNCAATTTTC TTTTNNTCAC GAACNCGNNC CNNAAAATGN   720

NNNNCNCCTC CNCTNGTCCN NAATCNCCAN C                                  751

(2) INFORMATION FOR SEQ ID NO: 40:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:
```

```
GTGGTATTTT CTGTAAGATC AGGTGTTCCT CCCTCGTAGG TTTAGAGGAA ACACCCTCAT      60

AGATGAAAAC CCCCCCGAGA CAGCAGCACT GCAACTGCCA AGCAGCCGGG GTAGGAGGGG     120

CGCCCTATGC ACAGCTGGGC CCTTGAGACA GCAGGGCTTC GATGTCAGGC TCGATGTCAA     180

TGGTCTGGAA GCGGCGGCTG TACCTGCGTA GGGGCACACC GTCAGGGCCC ACCAGGAACT     240

TCTCAAAGTT CCAGGCAACN TCGTTGCGAC ACACCGGAGA CCAGGTGATN AGCTTGGGGT     300

CGGTCATAAN CGCGGTGGCG TCGTCGCTGG GAGCTGGCAG GGCCTCCCGC AGGAAGGCNA     360

ATAAAAGGTG CGCCCCCGCA CCGTTCANCT CGCACTTCTC NAANACCATG ANGTTGGGCT     420

CNAACCCACC ACCANNCCGG ACTTCCTTGA NGGAATTCCC AAATCTCTTC GNTCTTGGGC     480

TTCTNCTGAT GCCCTANCTG GTTGCCCNGN ATGCCAANCA NCCCCAANCC CCGGGGTCCT     540

AAANCACCCN CCTCCTCNTT TCATCTGGGT TNTTNTCCCC GGACCNTGGT TCCTCTCAAG     600

GGANCCCATA TCTCNACCAN TACTCACCNT NCCCCCCCNT GNNACCCANC CTTCTANNGN     660

TTCCCNCCCG NCCTCTGGCC CNTCAAANAN GCTTNCACNA CCTGGGTCTG CCTTCCCCCC     720

TNCCCTATCT GNACCCCNCN TTTGTCTCAN TNT                                 753

(2) INFORMATION FOR SEQ ID NO: 41:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 41:

ACTATATCCA TCACAACAGA CATGCTTCAT CCCATAGACT TCTTGACATA GCTTCAAATG      60

AGTGAACCCA TCCTTGATTT ATATACATAT ATGTTCTCAG TATTTTGGGA GCCTTTCCAC     120

TTCTTTAAAC CTTGTTCATT ATGAACACTG AAAATAGGAA TTTGTGAAGA GTTAAAAAGT     180

TATAGCTTGT TTACGTAGTA AGTTTTTGAA GTCTACATTC AATCCAGACA CTTAGTTGAG     240

TGTTAAACTG TGATTTTTAA AAAATATCAT TTGAGAATAT TCTTTCAGAG GTATTTTCAT     300

TTTTACTTTT TGATTAATTG TGTTTTATAT ATTAGGGTAG T                        341

(2) INFORMATION FOR SEQ ID NO: 42:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 42:

ACTTACTGAA TTTAGTTCTG TGCTCTTCCT TATTTAGTGT TGTATCATAA ATACTTTGAT      60

GTTTCAAACA TTCTAAATAA ATAATTTTCA GTGGCTTCAT A                        101

(2) INFORMATION FOR SEQ ID NO: 43:

(i) SEQUENCE CHARACTERISTICS:
        (A) LENGTH: 305 base pairs
```

(B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo spiens (xi) SEQUENCE DESCRIPTION: SEQ ID NO: 43:

```
ACATCTTTGT TACAGTCTAA GATGTGTTCT TAAATCACCA TTCCTTCCTG GTCCTCACCC      60

TCCAGGGTGG TCTCACACTG TAATTAGAGC TATTGAGGAG TCTTTACAGC AAATTAAGAT     120

TCAGATGCCT TGCTAAGTCT AGAGTTCTAG AGTTATGTTT CAGAAAGTCT AAGAAACCCA     180

CCTCTTGAGA GGTCAGTAAA GAGGACTTAA TATTTCATAT CTACAAAATG ACCACAGGAT     240

TGGATACAGA ACGAGAGTTA TCCTGGATAA CTCAGAGCTG AGTACCTGCC CGGGGGCCGC     300

TCGAA                                                                305
```

(2) INFORMATION FOR SEQ ID NO: 44:

(i) SEQUENCE CHARACTERISTICS:
        (A) LENGTH: 852 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 44:

```
ACATAAATAT CAGAGAAAAG TAGTCTTTGA AATATTTACG TCCAGGAGTT CTTTGTTTCT      60

GATTATTTGG TGTGTGTTTT GGTTTGTGTC CAAAGTATTG GCAGCTTCAG TTTTCATTTT     120

CTCTCCATCC TCGGGCATTC TTCCCAAATT TATATACCAG TCTTCGTCCA TCCACACGCT     180

CCAGAATTTC TCTTTTGTAG TAATATCTCA TAGCTCGGCT GAGCTTTTCA TAGGTCATGC     240

TGCTGTTGTT CTTCTTTTTA CCCCATAGCT GAGCCACTGC CTCTGATTTC AAGAACCTGA     300

AGACGCCCTC AGATCGGTCT TCCCATTTTA TTAATCCTGG GTTCTTGTCT GGGTTCAAGA     360

GGATGTCGCG GATGAATTCC CATAAGTGAG TCCCTCTCGG GTTGTGCTTT TTGGTGTGGC     420

ACTTGGCAGG GGGGTCTTGC TCCTTTTTCA TATCAGGTGA CTCTGCAACA GGAAGGTGAC     480

TGGTGGTTGT CATGGAGATC TGAGCCCGGC AGAAAGTTTT GCTGTCCAAC AAATCTACTG     540

TGCTACCATA GTTGGTGTCA TATAAATAGT TCTNGTCTTT CCAGGTGTTC ATGATGGAAG     600

GCTCAGTTTG TTCAGTCTTG ACAATGACAT TGTGTGTGGA CTGGAACAGG TCACTACTGC     660

ACTGGCCGTT CCACTTCAGA TGCTGCAAGT TGCTGTAGAG GAGNTGCCCC GCCGTCCCTG     720

CCGCCCGGGT GAACTCCTGC AAACTCATGC TGCAAAGGTG CTCGCCGTTG ATGTCGAACT     780

CNTGGAAAGG GATACAATTG GCATCCAGCT GGTTGGTGTC CAGGAGGTGA TGGAGCCACT     840

CCCACACCTG GT                                                        852
```

(2) INFORMATION FOR SEQ ID NO: 45:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 45:

```
ACAACAGACC CTTGCTCGCT AACGACCTCA TGCTCATCAA GTTGGACGAA TCCGTGTCCG      60

AGTCTGACAC CATCCGGAGC ATCAGCATTG CTTCGCAGTG CCCTACCGCG GGGAACTCTT     120

GCCTCGTTTC TGGCTGGGGT CTGCTGGCGA ACGGCAGAAT GCCTACCGTG CTGCAGTGCG     180

TGAACGTGTC GGTGGTGTCT GAGGAGGTCT GCAGTAAGCT CTATGACCCG CTGT           234
```

(2) INFORMATION FOR SEQ ID NO: 46:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 46:

```
ACTTTTTATT TAAATGTTTA TAAGGCAGAT CTATGAGAAT GATAGAAAAC ATGGTGTGTA      60

ATTTGATAGC AATATTTTGG AGATTACAGA GTTTTAGTAA TTACCAATTA CACAGTTAAA     120

AAGAAGATAA TATATTCCAA GCANATACAA AATATCTAAT GAAAGATCAA GGCAGGAAAA     180

TGANTATAAC TAATTGACAA TGGAAAATCA ATTTTAATGT GAATTGCACA TTATCCTTTA     240

AAAGCTTTCA AAANAAANAA TTATTGCAGT CTANTTAATT CAAACAGTGT TAAATGGTAT     300

CAGGATAAAN AACTGAAGGG CANAAAGAAT TAATTTTCAC TTCATGTAAC NCACCCANAT     360

TTACAATGGC TTAAATGCAN GGAAAAAGCA GTGGAAGTAG GGAAGTANTC AAGGTCTTTC     420

TGGTCTCTAA TCTGCCTTAC TCTTTGGGTG TGGCTTTGAT CCTCTGGAGA CAGCTGCCAG     480

GGCTCCTGTT ATATCCACAA TCCCAGCAGC AAGATGAAGG GATGAAAAAG GACACATGCT     540

GCCTTCCTTT GAGGAGACTT CATCTCACTG GCCAACACTC AGTCACATGT                590
```

(2) INFORMATION FOR SEQ ID NO: 47:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 47:

```
ACAAGGGGC ATAATGAAGG AGTGGGANA GATTTTAAAG AAGGAAAAAA AACGAGGCCC        60

TGAACAGAAT TTTCCTGNAC AACGGGGCTT CAAAATAATT TTCTTGGGGA GGTTCAAGAC     120

GCTTCACTGC TTGAAACTTA AATGGATGTG GGACANAATT TTCTGTAATG ACCCTGAGGG     180

CATTACAGAC GGGACTCTGG GAGGAAGGAT AAACAGAAAG GGGACAAAGG CTAATCCCAA     240

AACATCAAAG AAAGGAAGGT GGCGTCATAC CTCCCAGCCT ACACAGTTCT CCAGGGCTCT     300

CCTCATCCCT GGAGGACGAC AGTGGAGGAA CAACTGACCA TGTCCCCAGG CTCCTGTGTG     360

CTGGCTCCTG GTCTTCAGCC CCCAGCTCTG GAAGCCCACC CTCTGCTGAT CCTGCGTGGC     420
```

```
CCACACTCCT TGAACACACA TCCCCAGGTT ATATTCCTGG ACATGGCTGA ACCTCCTATT      480

CCTACTTCCG AGATGCCTTG CTCCCTGCAG CCTGTCAAAA TCCCACTCAC CCTCCAAACC      540

ACGGCATGGG AAGCCTTTCT GACTTGCCTG ATTACTCCAG CATCTTGGAA CAATCCCTGA      600

TTCCCCACTC CTTAGAGGCA AGATAGGGTG GTTAAGAGTA GGGCTGGACC ACTTGGAGCC      660

AGGCTGCTGG CTTCAAATTN TGGCTCATTT ACGAGCTATG GGACCTTGGG CAAGTNATCT      720

TCACTTCTAT GGGCNTCATT TTGTTCTACC TGCAAAATGG GGGATAATAA TAGT            774

(2) INFORMATION FOR SEQ ID NO: 48:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 48:

CANAAATTGA AATTTTATAA AAAGGCATTT TTCTCTTTATA TCCATAAAAT GATATAATTT      60

TTGCAANTAT ANAAATGTGT CATAAATTAT AATGTTCCTT AATTACAGCT CAACGCAACT     120

TGGT                                                                  124

(2) INFORMATION FOR SEQ ID NO: 49:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 49:

GCCGATGCTA CTATTTTATT GCAGGAGGTG GGGGTGTTTT TATTATTCTC TCAACAGCTT      60

TGTGGCTACA GGTGGTGTCT GACTGCATNA AAAANTTTTT TACGGGTGAT TGCAAAAATT    120

TTAGGGCACC CATATCCCAA GCANTGT                                         147

(2) INFORMATION FOR SEQ ID NO: 50:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 50:

ACATTAAATT AATAAAAGGA CTGTTGGGGT TCTGCTAAAA CACATGGCTT GATATATTGC      60

ATGGTTTGAG GTTAGGAGGA GTTAGGCATA TGTTTTGGGA GAGGGGT                   107

(2) INFORMATION FOR SEQ ID NO: 51:
```

(i) SEQUENCE CHARACTERISTICS:
            (A) LENGTH: 204 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 51:

GTCCTAGGAA GTCTAGGGGA CACACGACTC TGGGGTCACG GGGCCGACAC ACTTGCACGG      60

CGGGAAGGAA AGGCAGAGAA GTGACACCGT CAGGGGGAAA TGACAGAAAG GAAAATCAAG     120

GCCTTGCAAG GTCAGAAAGG GGACTCAGGG CTTCCACCAC AGCCCTGCCC CACTTGGCCA     180

CCTCCCTTTT GGGACCAGCA ATGT                                            204

(2) INFORMATION FOR SEQ ID NO: 52:

(i) SEQUENCE CHARACTERISTICS:
            (A) LENGTH: 491 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 52:

ACAAAGATAA CATTTATCTT ATAACAAAAA TTTGATAGTT TTAAAGGTTA GTATTGTGTA      60

GGGTATTTTC CAAAAGACTA AAGAGATAAC TCAGGTAAAA AGTTAGAAAT GTATAAAACA     120

CCATCAGACA GGTTTTTAAA AAACAACATA TTACAAAATT AGACAATCAT CCTTAAAAAA     180

AAAACTTCTT GTATCAATTT CTTTTGTTCA AAATGACTGA CTTAANTATT TTTAAATATT     240

TCANAAACAC TTCCTCAAAA ATTTTCAANA TGGTAGCTTT CANATGTNCC CTCAGTCCCA     300

ATGTTGCTCA GATAAATAAA TCTCGTGAGA ACTTACCACC CACCACAAGC TTTCTGGGGC     360

ATGCAACAGT GTCTTTTCTT TNCTTTTTCT TTTTTTTTTT TTACAGGCAC AGAAACTCAT     420

CAATTTTATT TGGATAACAA AGGGTCTCCA AATTATATTG AAAAATAAAT CCAAGTTAAT     480

ATCACTCTTG T                                                          491

(2) INFORMATION FOR SEQ ID NO: 53:

(i) SEQUENCE CHARACTERISTICS:
            (A) LENGTH: 484 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 53:

ACATAATTTA GCAGGGCTAA TTACCATAAG ATGCTATTTA TTAANAGGTN TATGATCTGA      60

GTATTAACAG TTGCTGAAGT TTGGTATTTT TATGCAGCAT TTTCTTTTTG CTTTGATAAC     120

ACTACAGAAC CCTTAAGGAC ACTGAAAATT AGTAAGTAAA GTTCAGAAAC ATTAGCTGCT     180

CAATCAAATC TCTACATAAC ACTATAGTAA TTAAAACGTT AAAAAAAGT GTTGAAATCT     240

-continued

```
GCACTAGTAT ANACCGCTCC TGTCAGGATA ANACTGCTTT GGAACAGAAA GGGAAAAANC      300

AGCTTTGANT TTCTTTGTGC TGATANGAGG AAAGGCTGAA TTACCTTGTT GCCTCTCCCT      360

AATGATTGGC AGGTCNGGTA AATNCCAAAA CATATTCCAA CTCAACACTT CTTTTCCNCG      420

TANCTTGANT CTGTGTATTC CAGGANCAGG CGGATGGAAT GGGCCAGCCC NCGGATGTTC      480

CANT                                                                  484
```

(2) INFORMATION FOR SEQ ID NO: 54:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 54:

```
ACTAAACCTC GTGCTTGTGA ACTCCATACA GAAAACGGTG CCATCCCTGA ACACGGCTGG       60

CCACTGGGTA TACTGCTGAC AACCGCAACA ACAAAAACAC AAATCCTTGG CACTGGCTAG      120

TCTATGTCCT CTCAAGTGCC TTTTTGTTTG T                                    151
```

(2) INFORMATION FOR SEQ ID NO: 55:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 55:

```
ACCTGGCTTG TCTCCGGGTG GTTCCCGGCG CCCCCCACGG TCCCCAGAAC GGACACTTTC       60

GCCCTCCAGT GGATACTCGA GCCAAAGTGG T                                     91
```

(2) INFORMATION FOR SEQ ID NO: 56:

(i) SEQUENCE CHARACTERISTICS:
        (A) LENGTH: 133 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 56:

```
GGCGGATGTG CGTTGGTTAT ATACAAATAT GTCATTTTAT GTAAGGGACT TGAGTATACT       60

TGGATTTTTG GTATCTGTGG GTTGGGGGGA CGGTCCAGGA ACCAATACCC CATGGATACC      120

AAGGGACAAC TGT                                                        133
```

(2) INFORMATION FOR SEQ ID NO: 57:

(i) SEQUENCE CHARACTERISTICS:

(A) LENGTH: 147 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 57:

ACTCTGGAGA ACCTGAGCCG CTGCTCCGCC TCTGGGATGA GGTGATGCAN GCNGTGGCGC      60

GACTGGGAGC TGAGCCCTTC CCTTTGCGCC TGCCTCAGAG GATTGTTGCC GACNTGCANA     120

TCTCANTGGG CTGGATNCAT GCAGGGT                                        147

(2) INFORMATION FOR SEQ ID NO: 58:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 58:

ACAGGGATAT AGGTTTNAAG TTATTGTNAT TGTAAAATAC ATTGAATTTT CTGTATACTC      60

TGATTACATA CATTTATCCT TTAAAAAAGA TGTAAATCTT AATTTTTATG CCATCTATTA     120

ATTTACCAAT GAGTTACCTT GTAAATGAGA AGTCATGATA GCACTGAATT TTAACTAGTT     180

TTGACTTCTA AGTTTGGT                                                  198

(2) INFORMATION FOR SEQ ID NO: 59:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 59:

ACAACAAATG GGTTGTGAGG AAGTCTTATC AGCAAAACTG GTGATGGCTA CTGAAAAGAT      60

CCATTGAAAA TTATCATTAA TGATTTTAAA TGACAAGTTA TCAAAAACTC ACTCAATTTT     120

CACCTGTGCT AGCTTGCTAA AATGGGAGTT AACTCTAGAG CAAATATAGT ATCTTCTGAA     180

TACAGTCAAT AAATGACAAA GCCAGGGCCT ACAGGTGGTT TCCAGACTTT CCAGACCCAG     240

CAGAAGGAAT CTATTTTATC ACATGGATCT CCGTCTGTGC TCAAAATACC TAATGATATT     300

TTTCGTCTTT ATTGGACTTC TTTGAAGAGT                                     330

(2) INFORMATION FOR SEQ ID NO: 60:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 60:

| | |
|---|---|
| ACCGTGGGTG CCTTCTACAT TCCTGACGGC TCCTTCACCA ACATCTGGTT CTACTTCGGC | 60 |
| GTCGTGGGCT CCTTCCTCTT CATCCTCATC CAGCTGGTGC TGCTCATCGA CTTTGCGCAC | 120 |
| TCCTGGAACC AGCGGTGGCT GGGCAAGGCC GAGGAGTGCG ATTCCCGTGC CTGGT | 175 |

(2) INFORMATION FOR SEQ ID NO: 61:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 61:

| | |
|---|---|
| ACCCCACTTT TCCTCCTGTG AGCAGTCTGG ACTTCTCACT GCTACATGAT GAGGGTGAGT | 60 |
| GGTTGTTGCT CTTCAACAGT ATCCTCCCCT TTCCGGATCT GCTGAGCCGG ACAGCAGTGC | 120 |
| TGGACTGCAC AGCCCCGGGG CTCCACATTG CTGT | 154 |

(2) INFORMATION FOR SEQ ID NO: 62:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 62:

| | |
|---|---|
| CGCTCGAGCC CTATAGTGAG TCGTATTAGA | 30 |

(2) INFORMATION FOR SEQ ID NO: 63:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 63:

| | |
|---|---|
| ACAAGTCATT TCAGCACCCT TTGCTCTTCA AAACTGACCA TCTTTTATAT TTAATGCTTC | 60 |
| CTGTATGAAT AAAAATGGTT ATGTCAAGT | 89 |

(2) INFORMATION FOR SEQ ID NO: 64:

(i) SEQUENCE CHARACTERISTICS:
        (A) LENGTH: 97 base pairs
        (B) TYPE: nucleic acid

```
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 64:

ACCGGAGTAA CTGAGTCGGG ACGCTGAATC TGAATCCACC AATAAATAAA GGTTCTGCAG      60

AATCAGTGCA TCCAGGATTG GTCCTTGGAT CTGGGGT                              97

(2) INFORMATION FOR SEQ ID NO: 65:

(i) SEQUENCE CHARACTERISTICS:
        (A) LENGTH: 377 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 65:

ACAACAANAA NTCCCTTCTT TAGGCCACTG ATGGAAACCT GGAACCCCCT TTTGATGGCA      60

GCATGGCGTC CTAGGCCTTG ACACAGCGGC TGGGGTTTGG GCTNTCCCAA ACCGCACACC    120

CCAACCCTGG TCTACCCACA NTTCTGGCTA TGGGCTGTCT CTGCCACTGA ACATCAGGGT    180

TCGGTCATAA NATGAAATCC CAANGGGGAC AGAGGTCAGT AGAGGAAGCT CAATGAGAAA    240

GGTGCTGTTT GCTCAGCCAG AAAACAGCTG CCTGGCATTC GCCGCTGAAC TATGAACCCG    300

TGGGGGTGAA CTACCCCCAN GAGGAATCAT GCCTGGGCGA TGCAANGGTG CCAACAGGAG    360

GGGCGGGAGG AGCATGT                                                  377

(2) INFORMATION FOR SEQ ID NO: 66:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 66:

ACGCCTTTCC CTCAGAATTC AGGGAAGAGA CTGTCGCCTG CCTTCCTCCG TTGTTGCGTG      60

AGAACCCGTG TGCCCCTTCC CACCATATCC ACCCTCGCTC CATCTTTGAA CTCAAACACG    120

AGGAACTAAC TGCACCCTGG TCCTCTCCCC AGTCCCCAGT TCACCCTCCA TCCCTCACCT    180

TCCTCCACTC TAAGGGATAT CAACACTGCC CAGCACAGGG GCCCTGAATT TATGTGGTTT    240

TTATATATTT TTTAATAAGA TGCACTTTAT GTCATTTTTT AATAAAGTCT GAAGAATTAC    300

TGTTT                                                               305

(2) INFORMATION FOR SEQ ID NO: 67:

(i) SEQUENCE CHARACTERISTICS:
        (A) LENGTH: 385 base pairs
        (B) TYPE: nucleic acid
        (C) STRANDEDNESS: single
```

(D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 67:

```
ACTACACACA CTCCACTTGC CCTTGTGAGA CACTTTGTCC CAGCACTTTA GGAATGCTGA      60

GGTCGGACCA GCCACATCTC ATGTGCAAGA TTGCCCAGCA GACATCAGGT CTGAGAGTTC     120

CCCTTTTAAA AAAGGGGACT TGCTTAAAAA AGAAGTCTAG CCACGATTGT GTAGAGCAGC     180

TGTGCTGTGC TGGAGATTCA CTTTTGAGAG AGTTCTCCTC TGAGACCTGA TCTTTAGAGG     240

CTGGGCAGTC TTGCACATGA GATGGGGCTG GTCTGATCTC AGCACTCCTT AGTCTGCTTG     300

CCTCTCCCAG GGCCCCAGCC TGGCCACACC TGCTTACAGG GCACTCTCAG ATGCCCATAC     360

CATAGTTTCT GTGCTAGTGG ACCGT                                          385
```

(2) INFORMATION FOR SEQ ID NO: 68:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 68:

```
ACTTAACCAG ATATATTTTT ACCCCAGATG GGGATATTCT TTGTAAAAAA TGAAAATAAA      60

GTTTTTTTAA TGG                                                        73
```

(2) INFORMATION FOR SEQ ID NO: 69:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 69:

```
ACTAGTCCAG TGTGGTGGAA TTCCATTGTG TTGGGGGCTC TCACCCTCCT CTCCTGCAGC      60

TCCAGCTTTG TGCTCTGCCT CTGAGGAGAC CATGGCCCAG CATCTGAGTA CCCTGCTGCT     120

CCTGCTGGCC ACCCTAGCTG TGGCCCTGGC CTGGAGCCCC AAGGAGGAGG ATAGGATAAT     180

CCCGGGTGGC ATCTATAACG CAGACCTCAA TGATGAGTGG GTACAGCGTG CCCTTCACTT     240

CGCCATCAGC GAGTATAACA AGGCCACCAA AGATGACTAC TACAGACGTC CGCTGCGGGT     300

ACTAAGAGCC AGGCAACAGA CCGTTGGGGG GGTGAATTAC TTCTTCGACG TAGAGGTGGG     360

CCGAACCATA TGTACCAAGT CCCAGCCCAA CTTGGACACC TGTGCCTTCC ATGAACAGCC     420

AGAACTGCAG AAGAAACAGT TGTGCTCTTT CGAGATCTAC GAAGTTCCCT GGGGAGAACA     480

GAANGTCCCT GGGTGAAATC CAGGTGTCAA GAAATCCTAN GGATCTGTTG CCAGGC        536
```

(2) INFORMATION FOR SEQ ID NO: 70:

(i) SEQUENCE CHARACTERISTICS:
    (A) LENGTH: 477 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 70:

```
ATGACCCCTA ACAGGGGCCC TCTCAGCCCT CCTAATGACC TCCGGCCTAG CCATGTGATT    60

TCACTTCCAC TCCATAACGC TCCTCATACT AGGCCTACTA ACCAACACAC TAACCATATA   120

CCAATGATGG CGCGATGTAA CACGAGAAAG CACATACCAA GGCCACCACA CACCACCTGT   180

CCAAAAAGGC CTTCGATACG GGATAATCCT ATTTATTACC TCAGAAGTTT TTTTCTTCGC   240

AGGGATTTTT CTGAGCCTTT TACCACTCCA GCCTAGCCCC TACCCCCCAA CTAGGAGGGC   300

ACTGGCCCCC AACAGGCATC ACCCCGCTAA ATCCCCTAGA AGTCCACTC CTAAACACAT   360

CCGTATTACT CGCATCAGGA GTATCAATCA CCTGAGCTCA CCATAGTCTA ATAGAAAACA   420

ACCGAAACCA AATTATTCAA AGCACTGCTT ATTACAATTT TACTGGGTCT CTATTTT    477
```

(2) INFORMATION FOR SEQ ID NO: 71:

(i) SEQUENCE CHARACTERISTICS:
        (A) LENGTH: 533 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 71:

```
AGAGCTATAG GTACAGTGTG ATCTCAGCTT TGCAAACACA TTTTCTACAT AGATAGTACT    60

AGGTATTAAT AGATATGTAA AGAAAGAAAT CACACCATTA ATAATGGTAA GATTGGTTTA   120

TGTGATTTTA GTGGTATTTT TGGCACCCTT ATATATGTTT TCCAAACTTT CAGCAGTGAT   180

ATTATTTCCA TAACTTAAAA AGTGAGTTTG AAAAAGAAAA TCTCCAGCAA GCATCTCATT   240

TAAATAAAGG TTTGTCATCT TTAAAAATAC AGCAATATGT GACTTTTTAA AAAAGCTGTC   300

AAATAGGTGT GACCCTACTA ATAATTATTA GAAATACATT TAAAAACATC GAGTACCTCA   360

AGTCAGTTTG CCTTGAAAAA TATCAAATAT AACTCTTAGA GAAATGTACA TAAAAGAATG   420

CTTCGTAATT TTGGAGTANG AGGTTCCCTC CTCAATTTTG TATTTTTAAA AAGTACATGG   480

TAAAAAAAAA AATTCACAAC AGTATATAAG GCTGTAAAAT GAAGAATTCT GCC          533
```

(2) INFORMATION FOR SEQ ID NO: 72:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 72:

```
TATTACGGAA AAACACACCA CATAATTCAA CTANCAAAGA ANACTGCTTC AGGGCGTGTA        60

AAATGAAAGG CTTCCAGGCA GTTATCTGAT TAAAGAACAC TAAAAGAGGG ACAAGGCTAA       120

AAGCCGCAGG ATGTCTACAC TATANCAGGC GCTATTTGGG TTGGCTGGAG GAGCTGTGGA       180

AAACATGGAN AGATTGGTGC TGGANATCGC CGTGGCTATT CCTCATTGTT ATTACANAGT       240

GAGGTTCTCT GTGTGCCCAC TGGTTTGAAA ACCGTTCTNC AATAATGATA GAATAGTACA       300

CACATGAGAA CTGAAATGGC CCAAACCCAG AAAGAAAGCC CAACTAGATC CTCAGAANAC       360

GCTTCTAGGG ACAATAACCG ATGAAGAAAA GATGGCCTCC TTGTGCCCCC GTCTGTTATG       420

ATTTCTCTCC ATTGCAGCNA NAAACCCGTT CTTCTAAGCA AACNCAGGTG ATGATGGCNA       480

AAATACACCC CCTCTTGAAG NACCNGGAGG A                                     511

(2) INFORMATION FOR SEQ ID NO: 73:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 73:

CAGTGCCAGC ACTGGTGCCA GTACCAGTAC CAATAACAGT GCCAGTGCCA GTGCCAGCAC        60

CAGTGGTGGC TTCAGTGCTG GTGCCAGCCT GACCGCCACT CTCACATTTG GGCTCTTCGC       120

TGGCCTTGGT GGAGCTGGTG CCAGCACCAG TGGCAGCTCT GGTGCCTGTG GTTTCTCCTA       180

CAAGTGAGAT TTTAGATATT GTTAATCCTG CCAGTCTTTC TCTTCAAGCC AGGGTGCATC       240

CTCAGAAACC TACTCAACAC AGCACTCTAG GCAGCCACTA TCAATCAATT GAAGTTGACA       300

CTCTGCATTA AATCTATTTG CCATTTCTGA AAAAAAAAAA AAAAAAAGGG CGGCCGCTCG       360

ANTCTAGAGG GCCCGTTTAA ACCCGCTGAT CAGCCTCGAC TGTGCCTTCT ANTTGCCAGC       420

CATCTGTTGT TTGCCCCTCC CCCGNTGCCT TCCTTGACCC TGGAAAGTGC CACTCCCACT       480

GTCCTTTCCT AANTAAAAT                                                   499

(2) INFORMATION FOR SEQ ID NO: 74:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 74:

TTTCATAGGA GAACACACTG AGGAGATACT TGAAGAATTT GGATTCAGCC GCGAAGAGAT        60

TTATCAGCTT AACTCAGATA AAATCATTGA AAGTAATAAG GTAAAAGCTA GTCTCTAACT       120

TCCAGGCCCA CGGCTCAAGT GAATTTGAAT ACTGCATTTA CAGTGTAGAG TAACACATAA       180

CATTGTATGC ATGGAAACAT GGAGGAACAG TATTACAGTG TCCTACCACT CTAATCAAGA       240

AAAGAATTAC AGACTCTGAT TCTACAGTGA TGATTGAATT CTAAAAATGG TAATCATTAG       300
```

```
GGCTTTTGAT TTATAANACT TTGGGTACTT ATACTAAATT ATGGTAGTTA TACTGCCTTC      360

CAGTTTGCTT GATATATTTG TTGATATTAA GATTCTTGAC TTATATTTTG AATGGGTTCT      420

ACTGAAAAAN GAATGATATA TTCTTGAAGA CATCGATATA CATTTATTTA CACTCTTGAT      480

TCTACAATGT AGAAAATGAA GGAAATGCCC CAAATTGTAT GGTGATAAAA GTCCCGT         537
```

(2) INFORMATION FOR SEQ ID NO: 75:

(i) SEQUENCE CHARACTERISTICS:
        (A) LENGTH: 467 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 75:

```
CAAANACAAT TGTTCAAAAG ATGCAAATGA TACACTACTG CTGCAGCTCA CAAACACCTC       60

TGCATATTAC ACGTACCTCC TCCTGCTCCT CAAGTAGTGT GGTCTATTTT GCCATCATCA      120

CCTGCTGTCT GCTTAGAAGA ACGGCTTTCT GCTGCAANGG AGAGAAATCA TAACAGACGG      180

TGGCACAAGG AGGCCATCTT TTCCTCATCG GTTATTGTCC CTAGAAGCGT CTTCTGAGGA      240

TCTAGTTGGG CTTTCTTTCT GGGTTTGGGC CATTTCANTT CTCATGTGTG TACTATTCTA      300

TCATTATTGT ATAACGGTTT TCAAACCNGT GGGCACNCAG AGAACCTCAC TCTGTAATAA      360

CAATGAGGAA TAGCCACGGT GATCTCCAGC ACCAAATCTC TCCATGTTNT TCCAGAGCTC      420

CTCCAGCCAA CCCAAATAGC CGCTGCTATN GTGTAGAACA TCCCTGN                    467
```

(2) INFORMATION FOR SEQ ID NO: 76:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 76:

```
AAGCTGACAG CATTCGGGCC GAGATGTCTC GCTCCGTGGC CTTAGCTGTG CTCGCGCTAC       60

TCTCTCTTTC TGGCCTGGAG GCTATCCAGC GTACTCCAAA GATTCAGGTT TACTCACGTC      120

ATCCAGCAGA GAATGGAAAG TCAAATTTCC TGAATTGCTA TGTGTCTGGG TTTCATCCAT      180

CCGACATTGA AGTTGACTTA CTGAAGAATG GAGAGAGAAT TGAAAAAGTG GAGCATTCAG      240

ACTTGTCTTT CAGCAAGGAC TGGTCTTTCT ATCTCTTGTA CTACACTGAA TTCACCCCCA      300

CTGAAAAAGA TGAGTATGCC TGCCGTGTGA ACCATGTGAC TTTGTCACAG CCCAAGATNG      360

TTNAGTGGGA TCGANACATG TAAGCAGCAN CATGGGAGGT                            400
```

(2) INFORMATION FOR SEQ ID NO: 77:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo Sapiens (xi) SEQUENCE DESCRIPTION: SEQ ID NO: 77:

| | | | | | |
|---|---|---|---|---|---|
| CTGGAGTGCC | TTGGTGTTTC | AAGCCCCTGC | AGGAAGCAGA | ATGCACCTTC | TGAGGCACCT | 60 |
| CCAGCTGCCC | CGGCGGGGGA | TGCGAGGCTC | GGAGCACCCT | TGCCCGGCTG | TGATTGCTGC | 120 |
| CAGGCACTGT | TCATCTCAGC | TTTTCTGTCC | CTTTGCTCCC | GGCAAGCGCT | TCTGCTGAAA | 180 |
| GTTCATATCT | GGAGCCTGAT | GTCTTAACGA | ATAAAGGTCC | CATGCTCCAC | CCGAAAAAAA | 240 |
| AAAAAAAA | | | | | | 248 |

(2) INFORMATION FOR SEQ ID NO: 78:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 78:

| | | | | | |
|---|---|---|---|---|---|
| ACTAGTCCAG | TGTGGTGGAA | TTCCATTGTG | TTGGGCCCAA | CACAATGGCT | ACCTTTAACA | 60 |
| TCACCCAGAC | CCCGCCCTGC | CCGTGCCCCA | CGCTGCTGCT | AACGACAGTA | TGATGCTTAC | 120 |
| TCTGCTACTC | GGAAACTATT | TTTATGTAAT | TAATGTATGC | TTTCTTGTTT | ATAAATGCCT | 180 |
| GATTTAAAAA | AAAAAAAAA | A | | | | 201 |

(2) INFORMATION FOR SEQ ID NO: 79:

(i) SEQUENCE CHARACTERISTICS:
        (A) LENGTH: 552 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 79:

| | | | | | |
|---|---|---|---|---|---|
| TCCTTTTGTT | AGGTTTTTGA | GACAACCCTA | GACCTAAACT | GTGTCACAGA | CTTCTGAATG | 60 |
| TTTAGGCAGT | GCTAGTAATT | TCCTCGTAAT | GATTCTGTTA | TTACTTTCCT | ATTCTTTATT | 120 |
| CCTCTTTCTT | CTGAAGATTA | ATGAAGTTGA | AAATTGAGGT | GGATAAATAC | AAAAAGGTAG | 180 |
| TGTGATAGTA | TAAGTATCTA | AGTGCAGATG | AAAGTGTGTT | ATATATATCC | ATTCAAAATT | 240 |
| ATGCAAGTTA | GTAATTACTC | AGGGTTAACT | AAATTACTTT | AATATGCTGT | TGAACCTACT | 300 |
| CTGTTCCTTG | GCTAGAAAAA | ATTATAAACA | GGACTTTGTT | AGTTTGGGAA | GCCAAATTGA | 360 |
| TAATATTCTA | TGTTCTAAAA | GTTGGGCTAT | ACATAAANTA | TNAAGAAATA | TGGAATTTTA | 420 |
| TTCCCAGGAA | TATGGGGTTC | ATTTATGAAT | ANTACCCGGG | ANAGAAGTTT | TGANTNAAAC | 480 |
| CNGTTTTGGT | TAATACGTTA | ATATGTCCTN | AATNAACAAG | GCNTGACTTA | TTTCCAAAAA | 540 |
| AAAAAAAAA | AA | | | | | 552 |

(2) INFORMATION FOR SEQ ID NO: 80:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 80:

```
ACAGGGATTT GAGATGCTAA GGCCCCAGAG ATCGTTTGAT CCAACCCTCT TATTTTCAGA      60

GGGGAAAATG GGGCCTAGAA GTTACAGAGC ATCTAGCTGG TGCGCTGGCA CCCCTGGCCT     120

CACACAGACT CCCGAGTAGC TGGGACTACA GGCACACAGT CACTGAAGCA GGCCCTGTTT     180

GCAATTCACG TTGCCACCTC CAACTTAAAC ATTCTTCATA TGTGATGTCC TTAGTCACTA     240

AGGTTAAACT TTCCCACCCA GAAAAGGCAA CTTAGATAAA ATCTTAGAGT ACTTTCATAC     300

TCTTCTAAGT CCTCTTCCAG CCTCACTTTG AGTCCTCCTT GGGGGTTGAT AGGAANTNTC     360

TCTTGGCTTT CTCAATAAAA TCTCTATCCA TCTCATGTTT AATTTGGTAC GCNTAAAAAT     420

GCTGAAAAAA TTAAAATGTT CTGGTTTCNC TTTAAAAAAA AAAAAAAAAA AAAAAA        476
```

(2) INFORMATION FOR SEQ ID NO: 81:

(i) SEQUENCE CHARACTERISTICS:
        (A) LENGTH: 232 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 81:

```
TTTTTTTTTG TATGCCNTCN CTGTGGNGTT ATTGTTGCTG CCACCCTGGA GGAGCCCAGT      60

TTCTTCTGTA TCTTTCTTTT CTGGGGATC TTCCTGGCTC TGCCCCTCCA TTCCCAGCCT     120

CTCATCCCCA TCTTGCACTT TTGCTAGGGT TGGAGGCGCT TTCCTGGTAG CCCCTCAGAG     180

ACTCAGTCAG CGGGAATAAG TCCTAGGGGT GGGGGGTGTG GCAAGCCGGC CT            232
```

(2) INFORMATION FOR SEQ ID NO: 82:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 82:

```
AGGCGGGAGC AGAAGCTAAA GCCAAAGCCC AAGAAGAGTG GCAGTGCCAG CACTGGTGCC      60

AGTACCAGTA CCAATAACAT GCCAGTGCCA GTGCCAGCAC CAGTGGTGGC TTCAGTGCTG     120

GTGCCAGCCT GACCGCCACT CTCACATTTG GGCTCTTCGC TGGCCTTGGT GGAGCTGGTG     180

CCAGCACCAG TGGCAGCTCT GGTGCCTGTG GTTTCTCCTA CAAGTGAGAT TTTAGATATT     240

GTTAATCCTG CCAGTCTTTC TCTTCAAGCC AGGGTGCATC CTCAGAAACC TACTCAACAC     300
```

AGCACTCTNG GCAGCCACTA TCAATCAATT GAAGTTGACA CTCTGCATTA AATCTATTTG        360

CCATTTCAAA AAAAAAAAAA AAA                                               383

(2) INFORMATION FOR SEQ ID NO: 83:

(i) SEQUENCE CHARACTERISTICS:
        (A) LENGTH: 494 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 83:

ACCGAATTGG GACCGCTGGC TTATAAGCGA TCATGTCCTC CAGTATTACC TCAACGAGCA        60

GGGAGATCGA GTCTATACGC TGAAGAAATT TGACCCGATG GGACAACAGA CCTGCTCAGC       120

CCATCCTGCT CGGTTCTCCC CAGATGACAA ATACTCTCGA CACCGAATCA CCATCAAGAA       180

ACGCTTCAAG GTGCTCATGA CCCAGCAACC GCGCCCTGTC CTCTGAGGGT CCTTAAACTG       240

ATGTCTTTTC TGCCACCTGT TACCCCTCGG AGACTCCGTA ACCAAACTCT TCGGACTGTG       300

AGCCCTGATG CCTTTTTGCC AGCCATACTC TTTGGCNTCC AGTCTCTCGT GGCGATTGAT       360

TATGCTTGTG TGAGGCAATC ATGGTGGCAT CACCCATNAA GGGAACACAT TTGANTTTTT       420

TTTCNCATAT TTTAAATTAC NACCAGAATA NTTCAGAATA AATGAATTGA AAAACTCTTA       480

AAAAAAAAAA AAAA                                                         494

(2) INFORMATION FOR SEQ ID NO: 84:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 84:

GCTGGTAGCC TATGCGTGG CCACGGANGG GCTCCTGAGG CACGGGACAG TGACTTCCCA         60

AGTATCCTGC GCCGCGTCTT CTACCGTCCC TACCTGCAGA TCTTCGGGCA GATTCCCCAG       120

GAGGACATGG ACGTGGCCCT CATGGAGCAC AGCAACTGCT CGTCGGAGCC CGGCTTCTGG       180

GCACACCCTC CTGGGGCCCA GGCGGGCACC TGCGTCTCCC AGTATGCCAA CTGGCTGGTG       240

GTGCTGCTCC TCGTCATCTT CCTGCTCGTG GCCAACATCC TGCTGGTCAC TTGCTCATTG       300

CCATGTTCAG TTACACATTC GGCAAAGTAC AGGGCAACAG CNATCTCTAC TGGGAAGGCC       360

AGCGTTNCCG CCTCATCCGG                                                   380

(2) INFORMATION FOR SEQ ID NO: 85:

(i) SEQUENCE CHARACTERISTICS:
        (A) LENGTH: 481 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 85:

```
GAGTTAGCTC CTCCACAACC TTGATGAGGT CGTCTGCAGT GGCCTCTCGC TTCATACCGC      60
TNCCATCGTC ATACTGTAGG TTTGCCACCA CCTCCTGCAT CTTGGGGCGG CTAATATCCA     120
GGAAACTCTC AATCAAGTCA CCGTCNATNA AACCTGTGGC TGGTTCTGTC TTCCGCTCGG     180
TGTGAAAGGA TCTCCAGAAG GAGTGCTCGA TCTTCCCCAC ACTTTTGATG ACTTTATTGA     240
GTCGATTCTG CATGTCCAGC AGGAGGTTGT ACCAGCTCTC TGACAGTGAG GTCACCAGCC     300
CTATCATGCC NTTGAACGTG CCGAAGAACA CCGAGCCTTG TGTGGGGGT GNAGTCTCAC      360
CCAGATTCTG CATTACCAGA NAGCCGTGGC AAAAGANATT GACAACTCGC CCAGGNNGAA     420
AAAGAACACC TCCTGGAAGT GCTNGCCGCT CCTCGTCCNT TGGTGGNNGC GCNTNCCTTT     480
T                                                                    481
```

(2) INFORMATION FOR SEQ ID NO: 86:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 86:

```
AACATCTTCC TGTATAATGC TGTGTAATAT CGATCCGATN TTGTCTGCTG AGAATTCATT      60
ACTTGGAAAA GCAACTTNAA GCCTGGACAC TGGTATTAAA ATTCACAATA TGCAACACTT     120
TAAACAGTGT GTCAATCTGC TCCCTTACTT TGTCATCACC AGTCTGGGAA TAAGGGTATG     180
CCCTATTCAC ACCTGTTAAA AGGGCGCTAA GCATTTTTGA TTCAACATCT TTTTTTTTGA     240
CACAAGTCCG AAAAAAGCAA AAGTAAACAG TTNTTAATTT GTTAGCCAAT TCACTTTCTT     300
CATGGGACAG AGCCATTTGA TTTAAAAAGC AAATTGCATA ATATTGAGCT TTGGGAGCTG     360
ATATNTGAGC GGAAGANTAG CCTTTCTACT TCACCAGACA CAACTCCTTT CATATTGGGA     420
TGTTNACNAA AGTTATGTCT CTTACAGATG GGATGCTTTT GTGGCAATTC TG            472
```

(2) INFORMATION FOR SEQ ID NO: 87:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 87:

```
AGAAACCAGT ATCTCTNAAA ACAACCTCTC ATACCTTGTG GACCTAATTT TGTGTGCGTG      60
TGTGTGTGCG CGCATATTAT ATAGACAGGC ACATCTTTTT TACTTTTGTA AAAGCTTATG     120
CCTCTTTGGT ATCTATATCT GTGAAAGTTT TAATGATCTG CCATAATGTC TTGGGGACCT     180
TTGTCTTCTG TGTAAATGGT ACTAGAGAAA ACACCTATNT TATGAGTCAA TCTAGTTNGT     240
```

TTTATTCGAC ATGAAGGAAA TTTCCAGATN ACAACACTNA CAAACTCTCC CTTGACTAGG        300

GGGGACAAAG AAAAGCANAA CTGAACATNA GAAACAATTN CCTGGTGAGA AATTNCATAA        360

ACAGAAATTG GGTNGTATAT TGAAANANNG CATCATTNAA ACGTTTTTTT TTT              413

(2) INFORMATION FOR SEQ ID NO: 88:

(i) SEQUENCE CHARACTERISTICS:
        (A) LENGTH: 448 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 88:

CGCAGCGGGT CCTCTCTATC TAGCTCCAGC CTCTCGCCTG CCCCACTCCC CGCGTCCCGC         60

GTCCTAGCCN ACCATGGCCG GGCCCCTGCG CGCCCCGCTG CTCCTGCTGG CCATCCTGGC        120

CGTGGCCCTG GCCGTGAGCC CCGCGGCCGG CTCCAGTCCC GGCAAGCCGC CGCGCCTGGT        180

GGGAGGCCCA TGGACCCCGC GTGGAAGAAG AAGGTGTGCG GCGTGCACTG GACTTTGCCG        240

TCGGCNANTA CAACAAACCC GCAACNACTT TTACCNAGCN CGCGCTGCAG GTTGTGCCGC        300

CCCAANCAAA TTGTTACTNG GGGTAANTAA TTCTTGGAAG TTGAACCTGG GCCAAACNNG        360

TTTACCAGAA CCNAGCCAAT TNGAACAATT NCCCCTCCAT AACAGCCCCT TTTAAAAAGG        420

GAANCANTCC TGNTCTTTTC CAAATTTT                                          448

(2) INFORMATION FOR SEQ ID NO: 89:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 89:

GAATTTTGTG CACTGGCCAC TGTGATGGAA CCATTGGGCC AGGATGCTTT GAGTTTATCA         60

GTAGTGATTC TGCCAAAGTT GGTGTTGTAA CATGAGTATG TAAAATGTCA AAAAATTAGC        120

AGAGGTCTAG GTCTGCATAT CAGCAGACAG TTTGTCCGTG TATTTTGTAG CCTTGAAGTT        180

CTCAGTGACA AGTTNNTTCT GATGCGAAGT TCTNATTCCA GTGTTTTAGT CCTTTGCATC        240

TTTNATGTTN AGACTTGCCT CTNTNAAATT GCTTTTGTNT TCTGCAGGTA CTATCTGTGG        300

TTTAACAAAA TAGAANNACT TCTCTGCTTN GAANATTTGA ATATCTTACA TCTNAAAATN        360

AATTCTCTCC CCATANNAAA ACCCANGCCC TTGGGANAAT TTGAAAAANG GNTCCTTCNN        420

AATTCNNANA ANTTCAGNTN TCATACAACA NAACNGGANC CCC                         463

(2) INFORMATION FOR SEQ ID NO: 90:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 90:

AGGGATTGAA GGTCTNTTNT ACTGTCGGAC TGTTCANCCA CCAACTCTAC AAGTTGCTGT      60

CTTCCACTCA CTGTCTGTAA GCNTNTTAAC CCAGACTGTA TCTTCATAAA TAGAACAAAT     120

TCTTCACCAG TCACATCTTC TAGGACCTTT TTGGATTCAG TTAGTATAAG CTCTTCCACT     180

TCCTTTGTTA AGACTTCATC TGGTAAAGTC TTAAGTTTTG TAGAAAGGAA TTTAATTGCT     240

CGTTCTCTAA CAATGTCCTC TCCTTGAAGT ATTTGGCTGA ACAACCCACC TNAAGTCCCT     300

TTGTGCATCC ATTTTAAATA TACTTAATAG GGCATTGGTN CACTAGGTTA AATTCTGCAA     360

GAGTCATCTG TCTGCAAAAG TTGCGTTAGT ATATCTGCCA                            400

(2) INFORMATION FOR SEQ ID NO: 91:

(i) SEQUENCE CHARACTERISTICS:
             (A) LENGTH: 480 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 91:

GAGCTCGGAT CCAATAATCT TTGTCTGAGG GCAGCACACA TATNCAGTGC CATGGNAACT      60

GGTCTACCCC ACATGGGAGC AGCATGCCGT AGNTATATAA GGTCATTCCC TGAGTCAGAC     120

ATGCCTCTTT GACTACCGTG TGCCAGTGCT GGTGATTCTC ACACACCTCC NNCCGCTCTT     180

TGTGGAAAAA CTGGCACTTG NCTGGAACTA GCAAGACATC ACTTACAAAT TCACCCACGA     240

GACACTTGAA AGGTGTAACA AAGCGACTCT TGCATTGCTT TTTGTCCCTC CGGCACCAGT     300

TGTCAATACT AACCCGCTGG TTTGCCTCCA TCACATTTGT GATCTGTAGC TCTGGATACA     360

TCTCCTGACA GTACTGAAGA ACTTCTTCTT TTGTTTCAAA AGCAACTCTT GGTGCCTGTT     420

NGATCAGGTT CCCATTTCCC AGTCCGAATG TTCACATGGC ATATNTTACT TCCCACAAAA     480

(2) INFORMATION FOR SEQ ID NO: 92:

(i) SEQUENCE CHARACTERISTICS:
             (A) LENGTH: 477 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 92:

ATACAGCCCA NATCCCACCA CGAAGATGCG CTTGTTGACT GAGAACCTGA TGCGGTCACT      60

GGTCCCGCTG TAGCCCCAGC GACTCTCCAC CTGCTGGAAG CGGTTGATGC TGCACTCCTT     120

CCCACGCAGG CAGCAGCGGG GCCGGTCAAT GAACTCCACT CGTGGCTTGG GGTTGACGGT     180

TAANTGCAGG AAGAGGCTGA CCACCTCGCG GTCCACCAGG ATGCCCGACT GTGCGGGACC     240

TGCAGCGAAA CTCCTCGATG GTCATGAGCG GGAAGCGAAT GANGCCCAGG GCCTTGCCCA     300

```
GAACCTTCCG CCTGTTCTCT GGCGTCACCT GCAGCTGCTG CCGCTNACAC TCGGCCTCGG       360

ACCAGCGGAC AAACGGCGTT GAACAGCCGC ACCTCACGGA TGCCCANTGT GTCGCGCTCC       420

AGGAACGGCN CCAGCGTGTC CAGGTCAATG TCGGTGAANC CTCCGCGGGT AATGGCG         477
```

(2) INFORMATION FOR SEQ ID NO: 93:

(i) SEQUENCE CHARACTERISTICS:
        (A) LENGTH: 377 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 93:

```
GAACGGCTGG ACCTTGCCTC GCATTGTGCT GCTGGCAGGA ATACCTTGGC AAGCAGCTCC        60

AGTCCGAGCA GCCCCAGACC GCTGCCGCCC GAAGCTAAGC CTGCCTCTGG CCTTCCCCTC       120

CGCCTCAATG CAGAACCANT AGTGGGAGCA CTGTGTTTAG AGTTAAGAGT GAACACTGTN       180

TGATTTTACT TGGGAATTTC CTCTGTTATA TAGCTTTTCC CAATGCTAAT TTCCAAACAA       240

CAACAACAAA ATAACATGTT TGCCTGTTNA GTTGTATAAA AGTANGTGAT TCTGTATNTA       300

AAGAAAATAT TACTGTTACA TATACTGCTT GCAANTTCTG TATTTATTGG TNCTCTGGAA       360

ATAAATATAT TATTAAA                                                      377
```

(2) INFORMATION FOR SEQ ID NO: 94:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 94:

```
CCCTTTGAGG GGTTAGGGTC CAGTTCCCAG TGGAAGAAAC AGGCCAGGAG AANTGCGTGC        60

CGAGCTGANG CAGATTTCCC ACAGTGACCC CAGAGCCCTG GGCTATAGTC TCTGACCCCT       120

CCAAGGAAAG ACCACCTTCT GGGGACATGG GCTGGAGGGC AGGACCTAGA GGCACCAAGG       180

GAAGGCCCCA TTCGGGGCT GTTCCCCGAG GAGGAAGGGA AGGGGCTCTG TGTGCCCCCC        240

ACGAGGAANA GGCCCTGANT CCTGGGATCA NACACCCCTT CACGTGTATC CCCACACAAA       300

TGCAAGCTCA CCAAGGTCCC CTCTCAGTCC CTTCCCTACA CCCTGAACGG NCACTGGCCC       360

ACACCCACCC AGANCANCCA CCCGCCATGG GGAATGTNCT CAAGGAATCG CNGGGCAACG       420

TGGACTCTNG TCCCNNAAGG GGGCAGAATC TCCAATAGAN GGANNGAACC CTTGCTNANA       480

AAAAAAANA AAAAA                                                         495
```

(2) INFORMATION FOR SEQ ID NO: 95:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 95:

| | | | | | |
|---|---|---|---|---|---|
| GGTTACTTGG | TTTCATTGCC | ACCACTTAGT | GGATGTCATT | TAGAACCATT | TTGTCTGCTC | 60 |
| CCTCTGGAAG | CCTTGCGCAG | AGCGGACTTT | GTAATTGTTG | GAGAATAACT | GCTGAATTTT | 120 |
| TAGCTGTTTT | GAGTTGATTC | GCACCACTGC | ACCACAACTC | AATATGAAAA | CTATTTNACT | 180 |
| TATTTATTAT | CTTGTGAAAA | GTATACAATG | AAAATTTTGT | TCATACTGTA | TTTATCAAGT | 240 |
| ATGATGAAAA | GCAATAGATA | TATATTCTTT | TATTATGTTN | AATTATGATT | GCCATTATTA | 300 |
| ATCGGCAAAA | TGTGGAGTGT | ATGTTCTTTT | CACAGTAATA | TATGCCTTTT | GTAACTTCAC | 360 |
| TTGGTTATTT | TATTGTAAAT | GAATTACAAA | ATTCTTAATT | TAAGAAAATG | GTANGTTATA | 420 |
| TTTANTTCAN | TAATTTCTTT | CCTTGTTTAC | GTTAATTTTG | AAAAGAATGC | AT | 472 |

(2) INFORMATION FOR SEQ ID NO: 96:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 96:

| | | | | | |
|---|---|---|---|---|---|
| CTGAAGCATT | TCTTCAAACT | TNTCTACTTT | TGTCATTGAT | ACCTGTAGTA | AGTTGACAAT | 60 |
| GTGGTGAAAT | TTCAAAATTA | TATGTAACTT | CTACTAGTTT | TACTTTCTCC | CCCAAGTCTT | 120 |
| TTTTAACTCA | TGATTTTTAC | ACACACAATC | CAGAACTTAT | TATATAGCCT | CTAAGTCTTT | 180 |
| ATTCTTCACA | GTAGATGATG | AAAGAGTCCT | CCAGTGTCTT | GNGCANAATG | TTCTAGNTAT | 240 |
| AGCTGGATAC | ATACNGTGGG | AGTTCTATAA | ACTCATACCT | CAGTGGGACT | NAACCAAAAT | 300 |
| TGTGTTAGTC | TCAATTCCTA | CCACACTGAG | GGAGCCTCCC | AAATCACTAT | ATTCTTATCT | 360 |
| GCAGGTACTC | CTCCAGAAAA | ACNGACAGGG | CAGGCTTGCA | TGAAAAAGTN | ACATCTGCGT | 420 |
| TACAAAGTCT | ATCTTCCTCA | NANGTCTGTN | AAGGAACAAT | TTAATCTTCT | AGCTTT | 476 |

(2) INFORMATION FOR SEQ ID NO: 97:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 97:

| | | | | | |
|---|---|---|---|---|---|
| ACTCTTTCTA | ATGCTGATAT | GATCTTGAGT | ATAAGAATGC | ATATGTCACT | AGAATGGATA | 60 |
| AAATAATGCT | GCAAACTTAA | TGTTCTTATG | CAAAATGGAA | CGCTAATGAA | ACACAGCTTA | 120 |
| CAATCGCAAA | TCAAAACTCA | CAAGTGCTCA | TCTGTTGTAG | ATTTAGTGTA | ATAAGACTTA | 180 |
| GATTGTGCTC | CTTCGGATAT | GATTGTTTCT | CANATCTTGG | GCAATNTTCC | TTAGTCAAAT | 240 |

```
CAGGCTACTA GAATTCTGTT ATTGGATATN TGAGAGCATG AAATTTTTAA NAATACACTT      300

GTGATTATNA AATTAATCAC AAATTTCACT TATACCTGCT ATCAGCAGCT AGAAAAACAT      360

NTNNTTTTTA NATCAAAGTA TTTTGTGTTT GGAANTGTNN AAATGAAATC TGAATGTGGG      420

TTCNATCTTA TTTTTTCCCN GACNACTANT TNCTTTTTTA GGGNCTATTC TGANCCATC      479

(2) INFORMATION FOR SEQ ID NO: 98:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 98:

AGTGACTTGT CCTCCAACAA AACCCCTTGA TCAAGTTTGT GGCACTGACA ATCAGACCTA       60

TGCTAGTTCC TGTCATCTAT TCGCTACTAA ATGCAGACTG GAGGGACCA AAAAGGGGCA      120

TCAACTCCAG CTGGATTATT TTGGAGCCTG CAAATCTATT CCTACTTGTA CGGACTTTGA     180

AGTGATTCAG TTTCCTCTAC GGATGAGAGA CTGGCTCAAG AATATCCTCA TGCAGCTTTA     240

TGAAGCCACT CTGAACACGC TGGTTATCTA GATGAGAACA GAGAAATAAA GTCAGAAAAT     300

TTACCTGGAG AAAAGAGGCT TTGGCTGGGG ACCATCCCAT TGAACCTTCT CTTAAGGACT     360

TTAAGAAAAA CTACCACATG TTGTGTATCC TGGTGCCGGC CGTTTATGAA CTGACCACCC     420

TTTGGAATAA TCTTGACGCT CCTGAACTTG CTCCTCTGCG A                        461

(2) INFORMATION FOR SEQ ID NO: 99:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 99:

GTGGCCGCGC GCAGGTGTTT CCTCGTACCG CAGGGCCCCC TCCCTTCCCC AGGCGTCCCT       60

CGGCGCCTCT GCGGGCCCGA GGAGGAGCGG CTGGCGGGTG GGGGGAGTGT GACCCACCCT     120

CGGTGAGAAA AGCCTTCTCT AGCGATCTGA GAGGCGTGCC TTGGGGGTAC C              171

(2) INFORMATION FOR SEQ ID NO: 100:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 100:
```

```
CGGCCGCAAG TGCAACTCCA GCTGGGGCCG TGCGGACGAA GATTCTGCCA GCAGTTGGTC      60

CGACTGCGAC GACGGCGGCG GCGACAGTCG CAGGTGCAGC GCGGGCGCCT GGGGTCTTGC     120

AAGGCTGAGC TGACGCCGCA GAGGTCGTGT CACGTCCCAC GACCTTGACG CCGTCGGGGA     180

CAGCCGGAAC AGAGCCCGGT GAAGCGGGAG GCCTCGGGGA GCCCCTCGGG AAGGGCGGCC     240

CGAGAGATAC GCAGGTGCAG GTGGCCGCC                                      269
```

(2) INFORMATION FOR SEQ ID NO: 101:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 101:

```
TTTTTTTTTT TTTTGGAATC TACTGCGAGC ACAGCAGGTC AGCAACAAGT TTATTTTGCA      60

GCTAGCAAGG TAACAGGGTA GGGCATGGTT ACATGTTCAG GTCAACTTCC TTTGTCGTGG     120

TTGATTGGTT TGTCTTTATG GGGGCGGGGT GGGGTAGGGG AAACGAAGCA AATAACATGG     180

AGTGGGTGCA CCCTCCCTGT AGAACCTGGT TACAAAGCTT GGGGCAGTTC ACCTGGTCTG     240

TGACCGTCAT TTTCTTGACA TCAATGTTAT TAGAAGTCAG GATATCTTTT AGAGAGTCCA     300

CTGTTCTGGA GGGAGATTAG GGTTTCTTGC CAAATCCAAC AAAATCCACT GAAAAAGTTG     360

GATGATCAGT ACGAATACCG AGGCATATTC TCATATCGGT GGCCA                    405
```

(2) INFORMATION FOR SEQ ID NO: 102:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 102:

```
TTTTTTTTTT TTTTTTTTTT TTTTTTTTTT TTTTTTTTTT TTTTTTTTTT TTTTTTTTTT      60

GGCACTTAAT CCATTTTTAT TTCAAAATGT CTACAAATTT AATCCCATTA TACGTATTT      120

TCAAAATCTA AATTATTCAA ATTAGCCAAA TCCTTACCAA ATAATACCCA AAAATCAAAA     180

ATATACTTCT TTCAGCAAAC TTGTTACATA AATTAAAAAA ATATATACGG CTGGTGTTTT     240

CAAAGTACAA TTATCTTAAC ACTGCAAACA TTTTAAGGAA CTAAAATAAA AAAAACACT      300

CCGCAAAGGT TAAAGGGAAC AACAAATTCT TTTACAACAC CATTATAAAA ATCATATCTC     360

AAATCTTAGG GGAATATATA CTTCACACGG GATCTTAACT TTTACTCACT TGTTTTATTT     420

TTTTAAACCA TTGTTTGGGC CCAACACAAT GGAATCCCCC CTGGACTAGT                470
```

(2) INFORMATION FOR SEQ ID NO: 103:

(i) SEQUENCE CHARACTERISTICS:
        (A) LENGTH: 581 base pairs
        (B) TYPE: nucleic acid
        (C) STRANDEDNESS: single (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 103:

TTTTTTTTTT TTTTTTTTGA CCCCCCTCTT ATAAAAAACA AGTTACCATT TTATTTTACT      60

TACACATATT TATTTTATAA TTGGTATTAG ATATTCAAAA GGCAGCTTTT AAAATCAAAC     120

TAAATGGAAA CTGCCTTAGA TACATAATTC TTAGGAATTA GCTTAAAATC TGCCTAAAGT     180

GAAAATCTTC TCTAGCTCTT TTGACTGTAA ATTTTTGACT CTTGTAAAAC ATCCAAATTC     240

ATTTTTCTTG TCTTTAAAAT TATCTAATCT TTCCATTTTT TCCCTATTCC AAGTCAATTT     300

GCTTCTCTAG CCTCATTTCC TAGCTCTTAT CTACTATTAG TAAGTGGCTT TTTTCCTAAA     360

AGGGAAAACA GGAAGAGAAA TGGCACACAA AACAAACATT TTATATTCAT ATTTCTACCT     420

ACGTTAATAA AATAGCATTT TGTGAAGCCA GCTCAAAAGA AGGCTTAGAT CCTTTTATGT     480

CCATTTTAGT CACTAAACGA TATCAAAGTG CCAGAATGCA AAAGGTTTGT GAACATTTAT     540

TCAAAAGCTA ATATAAGATA TTTCACATAC TCATCTTTCT G                        581

(2) INFORMATION FOR SEQ ID NO: 104:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 104:

TTTTTTTTTT TTTTTTTTTT TTTTTCTCTT CTTTTTTTTT GAAATGAGGA TCGAGTTTTT      60

CACTCTCTAG ATAGGGCATG AAGAAAACTC ATCTTTCCAG CTTTAAAATA ACAATCAAAT     120

CTCTTATGCT ATATCATATT TTAAGTTAAA CTAATGAGTC ACTGGCTTAT CTTCTCCTGA     180

AGGAAATCTG TTCATTCTTC TCATTCATAT AGTTATATCA AGTACTACCT TGCATATTGA     240

GAGGTTTTTC TTCTCTATTT ACACATATAT TTCCATGTGA ATTTGTATCA AACCTTTATT     300

TTCATGCAAA CTAGAAAATA ATGTTTCTTT TGCATAAGAG AAGAGAACAA TATAGCATTA     360

CAAAACTGCT CAAATTGTTT GTTAAGTTAT CCATTATAAT TAGTTGGCAG GAGCTAATAC     420

AAATCACATT TACGACAGCA ATAATAAAAC TGAAGTACCA GTTAAATATC CAAAATAATT     480

AAAGGAACAT TTTTAGCCTG GGTATAATTA GCTAATTCAC TTTACAAGCA TTTATTAGAA     540

TGAATTCACA TGTTATTATT CCTAGCCCAA CACAATGG                            578

(2) INFORMATION FOR SEQ ID NO: 105:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 105:

| | | | | | |
|---|---|---|---|---|---|
| TTTTTTTTTT | TTTTTCAGTA | ATAATCAGAA | CAATATTTAT | TTTTATATTT | AAAATTCATA | 60 |
| GAAAAGTGCC | TTACATTTAA | TAAAAGTTTG | TTTCTCAAAG | TGATCAGAGG | AATTAGATAT | 120 |
| GTCTTGAACA | CCAATATTAA | TTTGAGGAAA | ATACACCAAA | ATACATTAAG | TAAATTATTT | 180 |
| AAGATCATAG | AGCTTGTAAG | TGAAAAGATA | AAATTTGACC | TCAGAAACTC | TGAGCATTAA | 240 |
| AAATCCACTA | TTAGCAAATA | AATTACTATG | GACTTCTTGC | TTTAATTTTG | TGATGAATAT | 300 |
| GGGGTGTCAC | TGGTAAACCA | ACACATTCTG | AAGGATACAT | TACTTAGTGA | TAGATTCTTA | 360 |
| TGTACTTTGC | TAATACGTGG | ATATGAGTTG | ACAAGTTTCT | CTTTCTTCAA | TCTTTTAAGG | 420 |
| GGCGAGAAAT | GAGGAAGAAA | AGAAAAGGAT | TACGCATACT | GTTCTTTCTA | TGGAAGGATT | 480 |
| AGATATGTTT | CCTTTGCCAA | TATTAAAAAA | ATAATAATGT | TTACTACTAG | TGAAACCC | 538 |

(2) INFORMATION FOR SEQ ID NO: 106:

(i) SEQUENCE CHARACTERISTICS:
        (A) LENGTH: 473 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 106:

| | | | | | |
|---|---|---|---|---|---|
| TTTTTTTTTT | TTTTTAGTC | AAGTTTCTAT | TTTTATTATA | ATTAAAGTCT | TGGTCATTTC | 60 |
| ATTTATTAGC | TCTGCAACTT | ACATATTTAA | ATTAAAGAAA | CGTTTTAGAC | AACTGTACAA | 120 |
| TTTATAAATG | TAAGGTGCCA | TTATTGAGTA | ATATATTCCT | CCAAGAGTGG | ATGTGTCCCT | 180 |
| TCTCCCACCA | ACTAATGAAC | AGCAACATTA | GTTTAATTTT | ATTAGTAGAT | ATACACTGCT | 240 |
| GCAAACGCTA | ATTCTCTTCT | CCATCCCCAT | GTGATATTGT | GTATATGTGT | GAGTTGGTAG | 300 |
| AATGCATCAC | AATCTACAAT | CAACAGCAAG | ATGAAGCTAG | GCTGGGCTTT | CGGTGAAAAT | 360 |
| AGACTGTGTC | TGTCTGAATC | AAATGATCTG | ACCTATCCTC | GGTGGCAAGA | ACTCTTCGAA | 420 |
| CCGCTTCCTC | AAAGGCGCTG | CCACATTTGT | GGCTCTTTGC | ACTTGTTTCA | AAA | 473 |

(2) INFORMATION FOR SEQ ID NO: 107:

(i) SEQUENCE CHARACTERISTICS:
        (A) LENGTH: 1621 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 107:

| | | | | | |
|---|---|---|---|---|---|
| CGCCATGGCA | CTGCAGGGCA | TCTCGGTCAT | GGAGCTGTCC | GGCCTGGCCC | CGGGCCCGTT | 60 |
| CTGTGCTATG | GTCCTGGCTG | ACTTCGGGGC | GCGTGTGGTA | CGCGTGGACC | GGCCCGGCTC | 120 |
| CCGCTACGAC | GTGAGCCGCT | GGGCCGGGG | CAAGCGCTCG | CTAGTGCTGG | ACCTGAAGCA | 180 |
| GCCGCGGGGA | GCCGCCGTGC | TGCGGCGTCT | GTGCAAGCGG | TCGGATGTGC | TGCTGGAGCC | 240 |
| CTTCCGCCGC | GGTGTCATGG | AGAAACTCCA | GCTGGGCCCA | GAGATTCTGC | AGCGGGAAAA | 300 |
| TCCAAGGCTT | ATTTATGCCA | GGCTGAGTGG | ATTTGGCCAG | TCAGGAAGCT | TCTGCCGGTT | 360 |

```
AGCTGGCCAC GATATCAACT ATTTGGCTTT GTCAGGTGTT CTCTCAAAAA TTGGCAGAAG      420

TGGTGAGAAT CCGTATGCCC CGCTGAATCT CCTGGCTGAC TTTGCTGGTG GTGGCCTTAT      480

GTGTGCACTG GGCATTATAA TGGCTCTTTT TGACCGCACA CGCACTGACA AGGGTCAGGT      540

CATTGATGCA AATATGGTGG AAGGAACAGC ATATTTAAGT TCTTTTCTGT GGAAAACTCA      600

GAAATCGAGT CTGTGGGAAG CACCTCGAGG ACAGAACATG TTGGATGGTG GAGCACCTTT      660

CTATACGACT TACAGGACAG CAGATGGGGA ATTCATGGCT GTTGGAGCAA TAGAACCCCA      720

GTTCTACGAG CTGCTGATCA AAGGACTTGG ACTAAAGTCT GATGAACTTC CCAATCAGAT      780

GAGCATGGAT GATTGGCCAG AAATGAAGAA GAAGTTTGCA GATGTATTTG CAAAGAAGAC      840

GAAGGCAGAG TGGTGTCAAA TCTTTGACGG CACAGATGCC TGTGTGACTC CGGTTCTGAC      900

TTTTGAGGAG GTTGTTCATC ATGATCACAA CAAGGAACGG GGCTCGTTTA TCACCAGTGA      960

GGAGCAGGAC GTGAGCCCCC GCCCTGCACC TCTGCTGTTA AACACCCCAG CCATCCCTTC     1020

TTTCAAAAGG GATCCTTTCA TAGGAGAACA CACTGAGGAG ATACTTGAAG AATTTGGATT     1080

CAGCCGCGAA GAGATTTATC AGCTTAACTC AGATAAAATC ATTGAAAGTA ATAAGGTAAA     1140

AGCTAGTCTC TAACTTCCAG GCCCACGGCT CAAGTGAATT TGAATACTGC ATTTACAGTG     1200

TAGAGTAACA CATAACATTG TATGCATGGA ACATGGAGG AACAGTATTA CAGTGTCCTA     1260

CCACTCTAAT CAAGAAAAGA ATTACAGACT CTGATTCTAC AGTGATGATT GAATTCTAAA     1320

AATGGTTATC ATTAGGGCTT TTGATTTATA AACTTTGGG TACTTATACT AAATTATGGT     1380

AGTTATTCTG CCTTCCAGTT TGCTTGATAT ATTTGTTGAT ATTAAGATTC TTGACTTATA     1440

TTTTGAATGG GTTCTAGTGA AAAGGAATG ATATATTCTT GAAGACATCG ATATACATTT     1500

ATTTACACTC TTGATTCTAC AATGTAGAAA ATGAGGAAAT GCCACAAATT GTATGGTGAT     1560

AAAAGTCACG TGAAACAAAA AAAAAAAAAA AAAAAAAAAA AAAAAAAAAA AAAAAAAAA     1620

A                                                                  1621
```

(2) INFORMATION FOR SEQ ID NO: 108:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 108:

```
Met Ala Leu Gln Gly Ile Ser Val Met Glu Leu Ser Gly Leu Ala Pro
1               5                   10                  15

Gly Pro Phe Cys Ala Met Val Leu Ala Asp Phe Gly Ala Arg Val Val
            20                  25                  30

Arg Val Asp Arg Pro Gly Ser Arg Tyr Asp Val Ser Arg Leu Gly Arg
        35                  40                  45

Gly Lys Arg Ser Leu Val Leu Asp Leu Lys Gln Pro Arg Gly Ala Ala
    50                  55                  60

Val Leu Arg Arg Leu Cys Lys Arg Ser Asp Val Leu Leu Glu Pro Phe
65                  70                  75                  80

Arg Arg Gly Val Met Glu Lys Leu Gln Leu Gly Pro Glu Ile Leu Gln
            85                  90                  95
```

-continued

```
Arg Glu Asn Pro Arg Leu Ile Tyr Ala Arg Leu Ser Gly Phe Gly Gln
            100                 105                 110
Ser Gly Ser Phe Cys Arg Leu Ala Gly His Asp Ile Asn Tyr Leu Ala
        115                 120                 125
Leu Ser Gly Val Leu Ser Lys Ile Gly Arg Ser Gly Glu Asn Pro Tyr
    130                 135                 140
Ala Pro Leu Asn Leu Leu Ala Asp Phe Ala Gly Gly Leu Met Cys
145                 150                 155                 160
Ala Leu Gly Ile Ile Met Ala Leu Phe Asp Arg Thr Arg Thr Asp Lys
                165                 170                 175
Gly Gln Val Ile Asp Ala Asn Met Val Glu Gly Thr Ala Tyr Leu Ser
            180                 185                 190
Ser Phe Leu Trp Lys Thr Gln Lys Ser Ser Leu Trp Glu Ala Pro Arg
        195                 200                 205
Gly Gln Asn Met Leu Asp Gly Gly Ala Pro Phe Tyr Thr Thr Tyr Arg
    210                 215                 220
Thr Ala Asp Gly Glu Phe Met Ala Val Gly Ala Ile Glu Pro Gln Phe
225                 230                 235                 240
Tyr Glu Leu Leu Ile Lys Gly Leu Gly Leu Lys Ser Asp Glu Leu Pro
                245                 250                 255
Asn Gln Met Ser Met Asp Asp Trp Pro Glu Met Lys Lys Lys Phe Ala
            260                 265                 270
Asp Val Phe Ala Lys Lys Thr Lys Ala Glu Trp Cys Gln Ile Phe Asp
        275                 280                 285
Gly Thr Asp Ala Cys Val Thr Pro Val Leu Thr Phe Glu Glu Val Val
    290                 295                 300
His His Asp His Asn Lys Glu Arg Gly Ser Phe Ile Thr Ser Glu Glu
305                 310                 315                 320
Gln Asp Val Ser Pro Arg Pro Ala Pro Leu Leu Leu Asn Thr Pro Ala
                325                 330                 335
Ile Pro Ser Phe Lys Arg Asp Pro Phe Ile Gly Glu His Thr Glu Glu
            340                 345                 350
Ile Leu Glu Glu Phe Gly Phe Ser Arg Glu Glu Ile Tyr Gln Leu Asn
        355                 360                 365
Ser Asp Lys Ile Ile Glu Ser Asn Lys Val Lys Ala Ser Leu
    370                 375                 380
```

(2) INFORMATION FOR SEQ ID NO: 109:

(i) SEQUENCE CHARACTERISTICS:
        (A) LENGTH: 1524 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 109:

```
GGCACGAGGC TGCGCCAGGG CCTGAGCGGA GGCGGGGGCA GCCTCGCCAG CGGGGGCCCC      60

GGGCCTGGCC ATGCCTCACT GAGCCAGCGC CTGCGCCTCT ACCTCGCCGA CAGCTGGAAC     120

CAGTGCGACC TAGTGGCTCT CACCTGCTTC CTCCTGGGCG TGGGCTGCCG GCTGACCCCG     180

GGTTTGTACC ACCTGGGCCG CACTGTCCTC TGCATCGACT TCATGGTTTT CACGGTGCGG     240

CTGCTTCACA TCTTCACGGT CAACAAACAG CTGGGGCCCA AGATCGTCAT CGTGAGCAAG     300
```

```
ATGATGAAGG ACGTGTTCTT CTTCCTCTTC TTCCTCGGCG TGTGGCTGGT AGCCTATGGC      360

GTGGCCACGG AGGGGCTCCT GAGGCCACGG GACAGTGACT TCCCAAGTAT CCTGCGCCGC      420

GTCTTCTACC GTCCCTACCT GCAGATCTTC GGGCAGATTC CCCAGGAGGA CATGGACGTG      480

GCCCTCATGG AGCACAGCAA CTGCTCGTCG GAGCCCGGCT TCTGGGCACA CCCTCCTGGG      540

GCCCAGGCGG GCACCTGCGT CTCCCAGTAT GCCAACTGGC TGGTGGTGCT GCTCCTCGTC      600

ATCTTCCTGC TCGTGGCCAA CATCCTGCTG GTCAACTTGC TCATTGCCAT GTTCAGTTAC      660

ACATTCGGCA AAGTACAGGG CAACAGCGAT CTCTACTGGA AGGCGCAGCG TTACCGCCTC      720

ATCCGGGAAT TCCACTCTCG GCCCGCGCTG GCCCCGCCCT TTATCGTCAT CTCCCACTTG      780

CGCCTCCTGC TCAGGCAATT GTGCAGGCGA CCCCGGAGCC CCCAGCCGTC CTCCCCGGCC      840

CTCGAGCATT TCCGGGTTTA CCTTTCTAAG GAAGCCGAGC GGAAGCTGCT AACGTGGGAA      900

TCGGTGCATA AGGAGAACTT TCTGCTGGCA CGCGCTAGGG ACAAGCGGGA GAGCGACTCC      960

GAGCGTCTGA AGCGCACGTC CCAGAAGGTG GACTTGGCAC TGAAACAGCT GGGACACATC     1020

CGCGAGTACG AACAGCGCCT GAAAGTGCTG GAGCGGGAGG TCCAGCAGTG TAGCCGCGTC     1080

CTGGGGTGGG TGGCCGAGGC CCTGAGCCGC TCTGCCTTGC TGCCCCCAGG TGGGCCGCCA     1140

CCCCCTGACC TGCCTGGGTC CAAAGACTGA GCCCTGCTGG CGGACTTCAA GGAGAAGCCC     1200

CCACAGGGGA TTTTGCTCCT AGAGTAAGGC TCATCTGGGC CTCGGCCCCC GCACCTGGTG     1260

GCCTTGTCCT TGAGGTGAGC CCCATGTCCA TCTGGGCCAC TGTCAGGACC ACCTTTGGGA     1320

GTGTCATCCT TACAAACCAC AGCATGCCCG GCTCCTCCCA GAACCAGTCC CAGCCTGGGA     1380

GGATCAAGGC CTGGATCCCG GGCCGTTATC CATCTGGAGG CTGCAGGGTC CTTGGGGTAA     1440

CAGGGACCAC AGACCCCTCA CCACTCACAG ATTCCTCACA CTGGGGAAAT AAAGCCATTT     1500

CAGAGGAAAA AAAAAAAAA AAAA                                            1524

(2) INFORMATION FOR SEQ ID NO: 110:

(i) SEQUENCE CHARACTERISTICS:
         (A) LENGTH: 3410 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO: 110:

GGGAACCAGC CTGCACGCGC TGGCTCCGGG TGACAGCCGC GCGCCTCGGC CAGGATCTGA       60

GTGATGAGAC GTGTCCCCAC TGAGGTGCCC CACAGCAGCA GGTGTTGAGC ATGGGCTGAG      120

AAGCTGGACC GGCACCAAAG GGCTGGCAGA AATGGGCGCC TGGCTGATTC CTAGGCAGTT      180

GGCGGCAGCA AGGAGGAGAG GCCGCAGCTT CTGGAGCAGA GCCGAGACGA AGCAGTTCTG      240

GAGTGCCTGA ACGCCCCCT GAGCCCTACC CGCCTGGCCC ACTATGGTCC AGAGGCTGTG      300

GGTGAGCCGC CTGCTGCGGC ACCGGAAAGC CCAGCTCTTG CTGGTCAACC TGCTAACCTT      360

TGGCCTGGAG GTGTGTTTGG CCGCAGGCAT CACCTATGTG CCGCCTCTGC TGCTGGAAGT      420

GGGGGTAGAG GAGAAGTTCA TGACCATGGT GCTGGGCATT GGTCCAGTGC TGGGCCTGGT      480

CTGTGTCCCG CTCCTAGGCT CAGCCAGTGA CCACTGGCGT GGACGCTATG GCCGCCGCCG      540

GCCCTTCATC TGGGCACTGT CCTTGGGCAT CCTGCTGAGC CTCTTTCTCA TCCCAAGGGC      600
```

-continued

```
CGGCTGGCTA GCAGGGCTGC TGTGCCCGGA TCCCAGGCCC CTGGAGCTGG CACTGCTCAT    660
CCTGGGCGTG GGGCTGCTGG ACTTCTGTGG CCAGGTGTGC TTCACTCCAC TGGAGGCCCT    720
GCTCTCTGAC CTCTTCCGGG ACCCGGACCA CTGTCGCCAG GCCTACTCTG TCTATGCCTT    780
CATGATCAGT CTTGGGGGCT GCCTGGGCTA CCTCCTGCCT GCCATTGACT GGGACACCAG    840
TGCCCTGGCC CCCTACCTGG GCACCCAGGA GGAGTGCCTC TTTGGCCTGC TCACCCTCAT    900
CTTCCTCACC TGCGTAGCAG CCACACTGCT GGTGGCTGAG GAGGCAGCGC TGGGCCCCAC    960
CGAGCCAGCA GAAGGGCTGT CGGCCCCCTC CTTGTCGCCC CACTGCTGTC CATGCCGGGC   1020
CCGCTTGGCT TTCCGGAACC TGGGCGCCCT GCTTCCCCGG CTGCACCAGC TGTGCTGCCG   1080
CATGCCCCGC ACCCTGCGCC GGCTCTTCGT GGCTGAGCTG TGCAGCTGGA TGGCACTCAT   1140
GACCTTCACG CTGTTTTACA CGGATTTCGT GGGCGAGGGG CTGTACCAGG GCGTGCCCAG   1200
AGCTGAGCCG GGCACCGAGG CCCGGAGACA CTATGATGAA GGCGTTCGGA TGGGCAGCCT   1260
GGGGCTGTTC CTGCAGTGCG CCATCTCCCT GGTCTTCTCT CTGGTCATGG ACCGGCTGGT   1320
GCAGCGATTC GGCACTCGAG CAGTCTATTT GGCCAGTGTG GCAGCTTTCC CTGTGGCTGC   1380
CGGTGCCACA TGCCTGTCCC ACAGTGTGGC CGTGGTGACA GCTTCAGCCG CCCTCACCGG   1440
GTTCACCTTC TCAGCCCTGC AGATCCTGCC CTACACACTG GCCTCCCTCT ACCACCGGGA   1500
GAAGCAGGTG TTCCTGCCCA ATACCGAGG GGACACTGGA GGTGCTAGCA GTGAGGACAG   1560
CCTGATGACC AGCTTCCTGC CAGGCCCTAA GCCTGGAGCT CCCTTCCCTA ATGGACACGT   1620
GGGTGCTGGA GGCAGTGGCC TGCTCCCACC TCCACCCGCG CTCTGCGGGG CCTCTGCCTG   1680
TGATGTCTCC GTACGTGTGG TGGTGGGTGA GCCCACCGAG GCCAGGGTGG TTCCGGGCCG   1740
GGGCATCTGC CTGGACCTCG CCATCCTGGA TAGTGCCTTC CTGCTGTCCC AGGTGGCCCC   1800
ATCCCTGTTT ATGGGCTCCA TTGTCCAGCT CAGCCAGTCT GTCACTGCCT ATATGGTGTC   1860
TGCCGCAGGC CTGGGTCTGG TCGCCATTTA CTTTGCTACA CAGGTAGTAT TTGACAAGAG   1920
CGACTTGGCC AAATACTCAG CGTAGAAAAC TTCCAGCACA TTGGGGTGGA GGGCCTGCCT   1980
CACTGGGTCC CAGCTCCCCG CTCCTGTTAG CCCCATGGGG CTGCCGGGCT GGCCGCCAGT   2040
TTCTGTTGCT GCCAAAGTAA TGTGGCTCTC TGCTGCCACC CTGTGCTGCT GAGGTGCGTA   2100
GCTGCACAGC TGGGGCTGG GGCGTCCCTC TCCTCTCTCC CCAGTCTCTA GGGCTGCCTG   2160
ACTGGAGGCC TTCCAAGGGG GTTTCAGTCT GGACTTATAC AGGGAGGCCA GAAGGGCTCC   2220
ATGCACTGGA ATGCGGGGAC TCTGCAGGTG GATTACCCAG GCTCAGGGTT AACAGCTAGC   2280
CTCCTAGTTG AGACACACCT AGAGAAGGGT TTTTGGGAGC TGAATAAACT CAGTCACCTG   2340
GTTTCCCATC TCTAAGCCCC TTAACCTGCA GCTTCGTTTA ATGTAGCTCT TGCATGGGAG   2400
TTTCTAGGAT GAAACACTCC TCCATGGGAT TTGAACATAT GACTTATTTG TAGGGGAAGA   2460
GTCCTGAGGG GCAACACACA AGAACCAGGT CCCCTCAGCC CACAGCACTG TCTTTTTGCT   2520
GATCCACCCC CCTCTTACCT TTTATCAGGA TGTGGCCTGT TGGTCCTTCT GTTGCCATCA   2580
CAGAGACACA GGCATTTAAA TATTTAACTT ATTTATTTAA CAAAGTAGAA GGGAATCCAT   2640
TGCTAGCTTT TCTGTGTTGG TGTCTAATAT TTGGGTAGGG TGGGGGATCC CCAACAATCA   2700
GGTCCCCTGA GATAGCTGGT CATTGGGCTG ATCATTGCCA GAATCTTCTT CTCCTGGGGT   2760
CTGGCCCCCC AAAATGCCTA ACCCAGGACC TTGGAAATTC TACTCATCCC AAATGATAAT   2820
TCCAAATGCT GTTACCCAAG GTTAGGGTGT TGAAGGAAGG TAGAGGGTGG GGCTTCAGGT   2880
CTCAACGGCT TCCCTAACCA CCCCTCTTCT CTTGGCCCAG CCTGGTTCCC CCCACTTCCA   2940
CTCCCCTCTA CTCTCTCTAG GACTGGGCTG ATGAAGGCAC TGCCCAAAAT TTCCCCTACC   3000
```

```
CCCAACTTTC CCCTACCCCC AACTTTCCCC ACCAGCTCCA CAACCCTGTT TGGAGCTACT      3060

GCAGGACCAG AAGCACAAAG TGCGGTTTCC CAAGCCTTTG TCCATCTCAG CCCCCAGAGT      3120

ATATCTGTGC TTGGGGAATC TCACACAGAA ACTCAGGAGC ACCCCCTGCC TGAGCTAAGG      3180

GAGGTCTTAT CTCTCAGGGG GGGTTTAAGT GCCGTTTGCA ATAATGTCGT CTTATTTATT      3240

TAGCGGGGTG AATATTTTAT ACTGTAAGTG AGCAATCAGA GTATAATGTT TATGGTGACA      3300

AAATTAAAGG CTTTCTTATA TGTTTAAAAA AAAAAAAAAA AAAAAAAAAA AAAAAAAAAA      3360

AAAAAAAARA AAAAAAAAAA AAAAAAAAAA AAAAAATAA AAAAAAAAA                  3410

(2) INFORMATION FOR SEQ ID NO: 111:

(i) SEQUENCE CHARACTERISTICS:
        (A) LENGTH: 1289 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 111:

AGCCAGGCGT CCCTCTGCCT GCCCACTCAG TGGCAACACC CGGGAGCTGT TTTGTCCTTT        60

GTGGAGCCTC AGCAGTTCCC TCTTTCAGAA CTCACTGCCA AGAGCCCTGA ACAGGAGCCA       120

CCATGCAGTG CTTCAGCTTC ATTAAGACCA TGATGATCCT CTTCAATTTG CTCATCTTTC       180

TGTGTGGTGC AGCCCTGTTG GCAGTGGGCA TCTGGGTGTC AATCGATGGG GCATCCTTTC       240

TGAAGATCTT CGGGCCACTG TCGTCCAGTG CCATGCAGTT TGTCAACGTG GGCTACTTCC       300

TCATCGCAGC CGGCGTTGTG GTCTTTGCTC TTGGTTTCCT GGGCTGCTAT GGTGCTAAGA       360

CTGAGAGCAA GTGTGCCCTC GTGACGTTCT TCTTCATCCT CCTCCTCATC TTCATTGCTG       420

AGGTTGCAGC TGCTGTGGTC GCCTTGGTGT ACACCACAAT GGCTGAGCAC TTCCTGACGT       480

TGCTGGTAGT GCCTGCCATC AAGAAAGATT ATGGTTCCCA GGAAGACTTC ACTCAAGTGT       540

GGAACACCAC CATGAAAGGG CTCAAGTGCT GTGGCTTCAC CAACTATACG GATTTTGAGG       600

ACTCACCCTA CTTCAAAGAG AACAGTGCCT TTCCCCCATT CTGTTGCAAT GACAACGTCA       660

CCAACACAGC CAATGAAACC TGCACCAAGC AAAAGGCTCA CGACCAAAAA GTAGAGGGTT       720

GCTTCAATCA GCTTTTGTAT GACATCCGAA CTAATGCAGT CACCGTGGGT GGTGTGGCAG       780

CTGGAATTGG GGGCCTCGAG CTGGCTGCCA TGATTGTGTC CATGTATCTG TACTGCAATC       840

TACAATAAGT CCACTTCTGC CTCTGCCACT ACTGCTGCCA CATGGGAACT GTGAAGAGGC       900

ACCCTGGCAA GCAGCAGTGA TTGGGGGAGG GGACAGGATC TAACAATGTC ACTTGGGCCA       960

GAATGGACCT GCCCTTTCTG CTCCAGACTT GGGGCTAGAT AGGGACCACT CCTTTTAGCG      1020

ATGCCTGACT TTCCTTCCAT TGGTGGGTGG ATGGGTGGGG GGCATTCCAG AGCCTCTAAG      1080

GTAGCCAGTT CTGTTGCCCA TTCCCCCAGT CTATTAAACC CTTGATATGC CCCCTAGGCC      1140

TAGTGGTGAT CCCAGTGCTC TACTGGGGGA TGAGAGAAAG GCATTTTATA GCCTGGGCAT      1200

AAGTGAAATC AGCAGAGCCT CTGGGTGGAT GTGTAGAAGG CACTTCAAAA TGCATAAACC      1260

TGTTACAATG TTAAAAAAAA AAAAAAAA                                        1289

(2) INFORMATION FOR SEQ ID NO: 112:

(i) SEQUENCE CHARACTERISTICS:
```

(A) LENGTH: 315 amino acids
          (B) TYPE: amino acid
          (C) STRANDEDNESS: single
          (D) TOPOLOGY: linear (ii) MOLECULE TYPE: protein (vi) ORIGINAL SOURCE:
          (A) ORGANISM: Homo sapiens (xi) SEQUENCE DESCRIPTION: SEQ ID NO: 112:

Met Val Phe Thr Val Arg Leu Leu His Ile Phe Thr Val Asn Lys Gln
1               5                   10                  15

Leu Gly Pro Lys Ile Val Ile Val Ser Lys Met Met Lys Asp Val Phe
                20                  25                  30

Phe Phe Leu Phe Phe Leu Gly Val Trp Leu Val Ala Tyr Gly Val Ala
            35                  40                  45

Thr Glu Gly Leu Leu Arg Pro Arg Asp Ser Asp Phe Pro Ser Ile Leu
        50                  55                  60

Arg Arg Val Phe Tyr Arg Pro Tyr Leu Gln Ile Phe Gly Gln Ile Pro
65                  70                  75                  80

Gln Glu Asp Met Asp Val Ala Leu Met Glu His Ser Asn Cys Ser Ser
                85                  90                  95

Glu Pro Gly Phe Trp Ala His Pro Pro Gly Ala Gln Ala Gly Thr Cys
            100                 105                 110

Val Ser Gln Tyr Ala Asn Trp Leu Val Val Leu Leu Val Ile Phe
            115                 120                 125

Leu Leu Val Ala Asn Ile Leu Leu Val Asn Leu Leu Ile Ala Met Phe
        130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Leu Arg Gln
            180                 185                 190

Leu Cys Arg Arg Pro Arg Ser Pro Gln Pro Ser Ser Pro Ala Leu Glu
        195                 200                 205

His Phe Arg Val Tyr Leu Ser Lys Glu Ala Glu Arg Lys Leu Leu Thr
210                 215                 220

Trp Glu Ser Val His Lys Glu Asn Phe Leu Leu Ala Arg Ala Arg Asp
225                 230                 235                 240

Lys Arg Glu Ser Asp Ser Glu Arg Leu Lys Arg Thr Ser Gln Lys Val
                245                 250                 255

Asp Leu Ala Leu Lys Gln Leu Gly His Ile Arg Glu Tyr Glu Gln Arg
            260                 265                 270

Leu Lys Val Leu Glu Arg Glu Val Gln Gln Cys Ser Arg Val Leu Gly
        275                 280                 285

Trp Val Ala Glu Ala Leu Ser Arg Ser Ala Leu Leu Pro Pro Gly Gly
        290                 295                 300

Pro Pro Pro Asp Leu Pro Gly Ser Lys Asp
305                 310                 315

(2) INFORMATION FOR SEQ ID NO: 113:

(i) SEQUENCE CHARACTERISTICS:
          (A) LENGTH: 553 amino acids
          (B) TYPE: amino acid
          (C) STRANDEDNESS: single (D) TOPOLOGY: linear (ii) MOLECULE TYPE: protein (vi) ORIGINAL SOURCE:
          (A) ORGANISM: Homo sapiens (xi) SEQUENCE DESCRIPTION: SEQ ID NO: 113:

Met Val Gln Arg Leu Trp Val Ser Arg Leu Leu Arg His Arg Lys Ala
1               5                   10                  15

Gln Leu Leu Val Asn Leu Leu Thr Phe Gly Leu Glu Val Cys Leu
            20                  25                  30

Ala Ala Gly Ile Thr Tyr Val Pro Pro Leu Leu Glu Val Gly Val
            35                  40                  45

Glu Glu Lys Phe Met Thr Met Val Leu Gly Ile Gly Pro Val Leu Gly
50                      55                  60

Leu Val Cys Val Pro Leu Leu Gly Ser Ala Ser Asp His Trp Arg Gly
65                  70                  75                  80

Arg Tyr Gly Arg Arg Arg Pro Phe Ile Trp Ala Leu Ser Leu Gly Ile
                85                  90                  95

Leu Leu Ser Leu Phe Leu Ile Pro Arg Ala Gly Trp Leu Ala Gly Leu
            100                 105                 110

Leu Cys Pro Asp Pro Arg Pro Leu Glu Leu Ala Leu Leu Ile Leu Gly
            115                 120                 125

Val Gly Leu Leu Asp Phe Cys Gly Gln Val Cys Phe Thr Pro Leu Glu
130                     135                 140

Ala Leu Leu Ser Asp Leu Phe Arg Asp Pro Asp His Cys Arg Gln Ala
145                 150                 155                 160

Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
            180                 185                 190

Gly Thr Gln Glu Glu Cys Leu Phe Gly Leu Leu Thr Leu Ile Phe Leu
            195                 200                 205

Thr Cys Val Ala Ala Thr Leu Leu Val Ala Glu Glu Ala Ala Leu Gly
210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
                245                 250                 255

Leu Pro Arg Leu His Gln Leu Cys Cys Arg Met Pro Arg Thr Leu Arg
            260                 265                 270

Arg Leu Phe Val Ala Glu Leu Cys Ser Trp Met Ala Leu Met Thr Phe
            275                 280                 285

Thr Leu Phe Tyr Thr Asp Phe Val Gly Glu Gly Leu Tyr Gln Gly Val
            290                 295                 300

Pro Arg Ala Glu Pro Gly Thr Glu Ala Arg Arg His Tyr Asp Glu Gly
305                 310                 315                 320

Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg
            340                 345                 350

Ala Val Tyr Leu Ala Ser Val Ala Ala Phe Pro Val Ala Ala Gly Ala
            355                 360                 365

Thr Cys Leu Ser His Ser Val Ala Val Val Thr Ala Ser Ala Ala Leu

```
            370                 375                 380
Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
                405                 410                 415

Asp Thr Gly Gly Ala Ser Ser Glu Asp Ser Leu Met Thr Ser Phe Leu
            420                 425                 430

Pro Gly Pro Lys Pro Gly Ala Pro Phe Pro Asn Gly His Val Gly Ala
            435                 440                 445

Gly Gly Ser Gly Leu Leu Pro Pro Pro Ala Leu Cys Gly Ala Ser
        450                 455                 460

Ala Cys Asp Val Ser Val Arg Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
            500                 505                 510

Ile Val Gln Leu Ser Gln Ser Val Thr Ala Tyr Met Val Ser Ala Ala
            515                 520                 525

Gly Leu Gly Leu Val Ala Ile Tyr Phe Ala Thr Gln Val Val Phe Asp
            530                 535                 540

Lys Ser Asp Leu Ala Lys Tyr Ser Ala
545                 550
```

(2) INFORMATION FOR SEQ ID NO: 114:

(i) SEQUENCE CHARACTERISTICS:
        (A) LENGTH: 241 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 114:

```
Met Gln Cys Phe Ser Phe Ile Lys Thr Met Met Ile Leu Phe Asn Leu
1               5                   10                  15

Leu Ile Phe Leu Cys Gly Ala Ala Leu Leu Ala Val Gly Ile Trp Val
            20                  25                  30

Ser Ile Asp Gly Ala Ser Phe Leu Lys Ile Phe Gly Pro Leu Ser Ser
            35                  40                  45

Ser Ala Met Gln Phe Val Asn Val Gly Tyr Phe Leu Ile Ala Ala Gly
    50                  55                  60

Val Val Val Phe Ala Leu Gly Phe Leu Gly Cys Tyr Gly Ala Lys Thr
65                  70                  75                  80

Glu Ser Lys Cys Ala Leu Val Thr Phe Phe Ile Leu Leu Leu Ile
            85                  90                  95

Phe Ile Ala Glu Val Ala Ala Ala Val Val Ala Leu Val Tyr Thr Thr
                100                 105                 110

Met Ala Glu His Phe Leu Thr Leu Val Val Pro Ala Ile Lys Lys
            115                 120                 125

Asp Tyr Gly Ser Gln Glu Asp Phe Thr Gln Val Trp Asn Thr Thr Met
            130                 135                 140

Lys Gly Leu Lys Cys Cys Gly Phe Thr Asn Tyr Thr Asp Phe Glu Asp
```

```
145                 150                 155                 160
Ser Pro Tyr Phe Lys Glu Asn Ser Ala Phe Pro Pro Phe Cys Cys Asn
                165                 170                 175
Asp Asn Val Thr Asn Thr Ala Asn Glu Thr Cys Thr Lys Gln Lys Ala
            180                 185                 190
His Asp Gln Lys Val Glu Gly Cys Phe Asn Gln Leu Leu Tyr Asp Ile
        195                 200                 205
Arg Thr Asn Ala Val Thr Val Gly Gly Val Ala Ala Gly Ile Gly Gly
    210                 215                 220
Leu Glu Leu Ala Ala Met Ile Val Ser Met Tyr Leu Tyr Cys Asn Leu
225                 230                 235                 240
Gln
```

(2) INFORMATION FOR SEQ ID NO: 115:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo Sapiens (xi) SEQUENCE DESCRIPTION: SEQ ID NO: 115:

```
GCTCTTTCTC TCCCCTCCTC TGAATTTAAT TCTTTCAACT TGCAATTTGC AAGGATTACA    60

CATTTCACTG TGATGTATAT TGTGTTGCAA AAAAAAAAAA GTGTCTTTGT TTAAAATTAC   120

TTGGTTTGTG AATCCATCTT GCTTTTTCCC CATTGGAACT AGTCATTAAC CCATCTCTGA   180

ACTGGTAGAA AAACATCTGA AGAGCTAGTC TATCAGCATC TGACAGGTGA ATTGGATGGT   240

TCTCAGAACC ATTTCACCCA GACAGCCTGT TTCTATCCTG TTTAATAAAT TAGTTTGGGT   300

TCTCTACATG CATAACAAAC CCTGCTCCAA TCTGTCACAT AAAAGTCTGT GACTTGAAGT   360

TTAGTC                                                             366
```

(2) INFORMATION FOR SEQ ID NO: 116:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 116:

```
ACAAAGATGA ACCATTTCCT ATATTATAGC AAAATTAAAA TCTACCCGTA TTCTAATATT    60

GAGAAATGAG ATNAAACACA ATNTTATAAA GTCTACTTAG AGAAGATCAA GTGACCTCAA   120

AGACTTTACT ATTTTCATAT TTAAGACAC ATGATTTATC CTATTTTAGT AACCTGGTTC    180

ATACGTTAAA CAAGGATAA TGTGAACAGC AGAGAGGATT TGTTGGCAGA AAATCTATGT    240

TCAATCTNGA ACTATCTANA TCACAGACAT TTCTATTCCT TT                      282
```

(2) INFORMATION FOR SEQ ID NO: 117:

(i) SEQUENCE CHARACTERISTICS:

(A) LENGTH: 305 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 117:

ACACATGTCG CTTCACTGCC TTCTTAGATG CTTCTGGTCA ACATANAGGA ACAGGGACCA      60

TATTTATCCT CCCTCCTGAA ACAATTGCAA AATAANACAA AATATATGAA ACAATTGCAA     120

AATAAGGCAA AATATATGAA ACAACAGGTC TCGAGATATT GGAAATCAGT CAATGAAGGA     180

TACTGATCCC TGATCACTGT CCTAATGCAG GATGTGGGAA ACAGATGAGG TCACCTCTGT     240

GACTGCCCCA GCTTACTGCC TGTAGAGAGT TTCTANGCTG CAGTTCAGAC AGGGAGAAAT     300

TGGGT                                                                305

(2) INFORMATION FOR SEQ ID NO: 118:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 118:

ACCAAGGTGT NTGAATCTCT GACGTGGGGA TCTCTGATTC CCGCACAATC TGAGTGGAAA      60

AANTCCTGGG T                                                          71

(2) INFORMATION FOR SEQ ID NO: 119:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 119:

ACTCCGGTTG GTGTCAGCAG CACGTGGCAT TGAACATNGC AATGTGGAGC CCAAACCACA      60

GAAAATGGGG TGAAATTGGC CAACTTTCTA TNAACTTATG TTGGCAANTT TGCCACCAAC     120

AGTAAGCTGG CCCTTCTAAT AAAAGAAAAT TGAAAGGTTT CTCACTAANC GGAATTAANT     180

AATGGANTCA AGANACTCCC AGGCCTCAGC GT                                   212

(2) INFORMATION FOR SEQ ID NO: 120:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 120:

ACTCGTTGCA NATCAGGGGC CCCCCAGAGT CACCGTTGCA GGAGTCCTTC TGGTCTTGCC      60

CTCCGCCGGC GCAGAACATG CTGGGGTGGT      90

(2) INFORMATION FOR SEQ ID NO: 121:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 121:

TGTANCGTGA ANACGACAGA NAGGGTTGTC AAAAATGGAG AANCCTTGAA GTCATTTTGA      60

GAATAAGATT TGCTAAAAGA TTTGGGGCTA AAACATGGTT ATTGGGAGAC ATTTCTGAAG     120

ATATNCANGT AAATTANGGA ATGAATTCAT GGTTCTTTTG GGAATTCCTT TACGATNGCC     180

AGCATANACT TCATGTGGGG ATANCAGCTA CCCTTGTA      218

(2) INFORMATION FOR SEQ ID NO: 122:

(i) SEQUENCE CHARACTERISTICS:
        (A) LENGTH: 171 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 122:

TAGGGGTGTA TGCAACTGTA AGGACAAAAA TTGAGACTCA ACTGGCTTAA CCAATAAAGG      60

CATTTGTTAG CTCATGGAAC AGGAAGTCGG ATGGTGGGGC ATCTTCAGTG CTGCATGAGT     120

CACCACCCCG GCGGGGTCAT CTGTGCCACA GGTCCCTGTT GACAGTGCGG T     171

(2) INFORMATION FOR SEQ ID NO: 123:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 123:

TGTAGCGTGA AGACNACAGA ATGGTGTGTG CTGTGCTATC CAGGAACACA TTTATTATCA      60

TTATCAANTA TTGTGT      76

(2) INFORMATION FOR SEQ ID NO: 124:

(i) SEQUENCE CHARACTERISTICS:

(A) LENGTH: 131 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 124:

ACCTTTCCCC AAGGCCAATG TCCTGTGTGC TAACTGGCCG GCTGCAGGAC AGCTGCAATT      60

CAATGTGCTG GGTCATATGG AGGGGAGGAG ACTCTAAAAT AGCCAATTTT ATTCTCTTGG     120

TTAAGATTTG T                                                         131

(2) INFORMATION FOR SEQ ID NO: 125:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 125:

ACTTTATCTA CTGGCTATGA AATAGATGGT GGAAAATTGC GTTACCAACT ATACCACTGG      60

CTTGAAAAAG AGGTGATAGC TCTTCAGAGG ACTTGTGACT TTTGCTCAGA TGCTGAAGAA     120

CTACAGTCTG CATTTGGCAG AAATGAAGAT GAATTTGGAT TAAATGAGGA TGCTGAAGAT     180

TTGCCTCACC AAACAAAAGT GAAACAACTG AGAGAAAATT TTCAGGAAAA AAGACAGTGG     240

CTCTTGAAGT ATCAGTCACT TTTGAGAATG TTTCTTAGTT ACTGCATACT TCATGGATCC     300

CATGGTGGGG GTCTTGCATC TGTAAGAATG GAATTGATTT TGCTTTTGCA AGAATCTCAG     360

CAGGAAACAT CAGAACCACT ATTTTCTAGC CCTCTGTCAG AGCAAACCTC AGTGCCTCTC     420

CTCTTTGCTT GT                                                        432

(2) INFORMATION FOR SEQ ID NO: 126:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 126:

ACACAACTTG AATAGTAAAA TAGAAACTGA GCTGAAATTT CTAATTCACT TTCTAACCAT      60

AGTAAGAATG ATATTTCCCC CCAGGGATCA CCAAATATTT ATAAAAATTT GT             112

(2) INFORMATION FOR SEQ ID NO: 127:

(i) SEQUENCE CHARACTERISTICS:
        (A) LENGTH: 54 base pairs
        (B) TYPE: nucleic acid
        (C) STRANDEDNESS: single
        (D) TOPOLOGY: linear

```
        (ii) MOLECULE TYPE: cDNA (vi) ORIGINAL SOURCE:
             (A) ORGANISM: Homo sapiens (xi) SEQUENCE DESCRIPTION: SEQ ID NO: 127:

ACCACGAAAC CACAAACAAG ATGGAAGCAT CAATCCACTT GCCAAGCACA GCAG            54

(2) INFORMATION FOR SEQ ID NO: 128:

(i) SEQUENCE CHARACTERISTICS:
             (A) LENGTH: 323 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 128:

ACCTCATTAG TAATTGTTTT GTTGTTTCAT TTTTTTCTAA TGTCTCCCCT CTACCAGCTC       60

ACCTGAGATA ACAGAATGAA AATGGAAGGA CAGCCAGATT TCTCCTTTGC TCTCTGCTCA      120

TTCTCTCTGA AGTCTAGGTT ACCCATTTTG GGGACCCATT ATAGGCAATA AACACAGTTC      180

CCAAAGCATT TGGACAGTTT CTTGTTGTGT TTTAGAATGG TTTTCCTTTT TCTTAGCCTT      240

TTCCTGCAAA AGGCTCACTC AGTCCCTTGC TTGCTCAGTG GACTGGGCTC CCCAGGGCCT      300

AGGCTGCCTT CTTTTCCATG TCC                                             323

(2) INFORMATION FOR SEQ ID NO: 129:

(i) SEQUENCE CHARACTERISTICS:
             (A) LENGTH: 192 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 129:

ACATACATGT GTGTATATTT TTAAATATCA CTTTTGTATC ACTCTGACTT TTTAGCATAC       60

TGAAAACACA CTAACATAAT TTNTGTGAAC CATGATCAGA TACAACCCAA ATCATTCATC      120

TAGCACATTC ATCTGTGATA NAAAGATAGG TGAGTTTCAT TTCCTTCACG TTGGCCAATG      180

GATAAACAAA GT                                                         192

(2) INFORMATION FOR SEQ ID NO: 130:

(i) SEQUENCE CHARACTERISTICS:
             (A) LENGTH: 362 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 130:

CCCTTTTTTA TGGAATGAGT AGACTGTATG TTTGAANATT TANCCACAAC CTCTTTGACA       60
```

```
TATAATGACG CAACAAAAAG GTGCTGTTTA GTCCTATGGT TCAGTTTATG CCCCTGACAA      120

GTTTCCATTG TGTTTTGCCG ATCTTCTGGC TAATCGTGGT ATCCTCCATG TTATTAGTAA      180

TTCTGTATTC CATTTTGTTA ACGCCTGGTA GATGTAACCT GCTANGAGGC TAACTTTATA      240

CTTATTTAAA AGCTCTTATT TTGTGGTCAT TAAAATGGCA ATTTATGTGC AGCACTTTAT      300

TGCAGCAGGA AGCACGTGTG GGTTGGTTGT AAAGCTCTTT GCTAATCTTA AAAAGTAATG      360

GG                                                                    362

(2) INFORMATION FOR SEQ ID NO: 131:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 131:

CTTTTTGAAA GATCGTGTCC ACTCCTGTGG ACATCTTGTT TTAATGGAGT TTCCCATGCA       60

GTANGACTGG TATGGTTGCA GCTGTCCAGA TAAAAACATT TGAAGAGCTC CAAAATGAGA      120

GTTCTCCCAG GTTCGCCCTG CTGCTCCAAG TCTCAGCAGC AGCCTCTTTT AGGAGGCATC      180

TTCTGAACTA GATTAAGGCA GCTTGTAAAT CTGATGTGAT TTGGTTTATT ATCCAACTAA      240

CTTCCATCTG TTATCACTGG AGAAAGCCCA GACTCCCCAN GACNGGTACG GATTGTGGGC      300

ATANAAGGAT TGGGTGAAGC TGGCGTTGTG GT                                   332

(2) INFORMATION FOR SEQ ID NO: 132:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 132:

ACTTTTGCCA TTTTGTATAT ATAAACAATC TTGGGACATT CTCCTGAAAA CTAGGTGTCC       60

AGTGGCTAAG AGAACTCGAT TTCAAGCAAT TCTGAAAGGA AAACCAGCAT GACACAGAAT      120

CTCAAATTCC CAAACAGGGG CTCTGTGGGA AAAATGAGGG AGGACCTTTG TATCTCGGGT      180

TTTAGCAAGT TAAAATGAAN ATGACAGGAA AGGCTTATTT ATCAACAAAG AGAAGAGTTG      240

GGATGCTTCT AAAAAAAACT TTGGTAGAGA AAATAGGAAT GCTNAATCCT AGGGAAGCCT      300

GTAACAATCT ACAATTGGTC CA                                              322

(2) INFORMATION FOR SEQ ID NO: 133:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: cDNA
```

(vi) ORIGINAL SOURCE:
    (A) ORGANISM: Homo sapiens (xi) SEQUENCE DESCRIPTION: SEQ ID NO: 133:

| | | | | | |
|---|---|---|---|---|---|
| ACAAGCCTTC | ACAAGTTTAA | CTAAATTGGG | ATTAATCTTT | CTGTANTTAT | CTGCATAATT | 60
| CTTGTTTTTC | TTTCCATCTG | GCTCCTGGGT | TGACAATTTG | TGGAAACAAC | TCTATTGCTA | 120
| CTATTTAAAA | AAAATCACAA | ATCTTTCCCT | TTAAGCTATG | TTNAATTCAA | ACTATTCCTG | 180
| CTATTCCTGT | TTTGTCAAAG | AAATTATATT | TTTCAAAATA | TGTNTATTTG | TTTGATGGGT | 240
| CCCACGAAAC | ACTAATAAAA | ACCACAGAGA | CCAGCCTG | | | 278

(2) INFORMATION FOR SEQ ID NO: 134:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 134:

GTTTANAAAA CTTGTTTAGC TCCATAGAGG AAAGAATGTT AAACTTTGTA TTTTAAAACA    60
TGATTCTCTG AGGTTAAACT TGGTTTTCAA ATGTTATTTT TACTTGTATT TTGCTTTTGG   120
T                                                                  121

(2) INFORMATION FOR SEQ ID NO: 135:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 135:

ACTTANAACC ATGCCTAGCA CATCAGAATC CCTCAAAGAA CATCAGTATA ATCCTATACC    60
ATANCAAGTG GTGACTGGTT AAGCGTGCGA CAAAGGTCAG CTGGCACATT ACTTGTGTGC   120
AAACTTGATA CTTTTGTTCT AAGTAGGAAC TAGTATACAG TNCCTAGGAN TGGTACTCCA   180
GGGTGCCCCC CAACTCCTGC AGCCGCTCCT CTGTGCCAGN CCCTGNAAGG AACTTTCGCT   240
CCACCTCAAT CAAGCCCTGG GCCATGCTAC CTGCAATTGG CTGAACAAAC GTTTGCTGAG   300
TTCCCAAGGA TGCAAAGCCT GGTGCTCAAC TCCTGGGGCG TCAACTCAGT              350

(2) INFORMATION FOR SEQ ID NO: 136:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 136:

TGTACCGTGA AGACGACAGA AGTTGCATGG CAGGGACAGG GCAGGGCCGA GGCCAGGGTT      60

GCTGTGATTG TATCCGAATA NTCCTCGTGA GAAAAGATAA TGAGATGACG TGAGCAGCCT     120

GCAGACTTGT GTCTGCCTTC AANAAGCCAG ACAGGAAGGC CCTGCCTGCC TTGGCTCTGA     180

CCTGGCGGCC AGCCAGCCAG CCACAGGTGG GCTTCTTCCT TTTGTGGTGA CAACNCCAAG     240

AAAACTGCAG AGGCCCAGGG TCAGGTGTNA GTGGGTANGT GACCATAAAA CACCAGGTGC     300

TCCCAGGAAC CCGGGCAAAG GCCATCCCCA CCTACAGCCA GCATGCCCAC TGGCGTGATG     360

GGTGCAGANG GATGAAGCAG CCAGNTGTTC TGCTGTGGT                            399

(2) INFORMATION FOR SEQ ID NO: 137:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 137:

ACTGGTGTGG TNGGGGGTGA TGCTGGTGGT ANAAGTTGAN GTGACTTCAN GATGGTGTGT      60

GGAGGAAGTG TGTGAACGTA GGGATGTAGA NGTTTTGGCC GTGCTAAATG AGCTTCGGGA     120

TTGGCTGGTC CCACTGGTGG TCACTGTCAT TGGTGGGGTT CCTGT                    165

(2) INFORMATION FOR SEQ ID NO: 138:

(i) SEQUENCE CHARACTERISTICS:
        (A) LENGTH: 338 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 138:

ACTCACTGGA ATGCCACATT CACAACAGAA TCAGAGGTCT GTGAAAACAT TAATGGCTCC      60

TTAACTTCTC CAGTAAGAAT CAGGGACTTG AAATGGAAAC GTTAACAGCC ACATGCCCAA     120

TGCTGGGCAG TCTCCCATGC CTTCCACAGT GAAAGGGCTT GAGAAAAATC ACATCCAATG     180

TCATGTGTTT CCAGCCACAC CAAAAGGTGC TTGGGGTGGA GGGCTGGGGG CATANANGGT     240

CANGCCTCAG GAAGCCTCAA GTTCCATTCA GCTTTGCCAC TGTACATTCC CCATNTTTAA     300

AAAAACTGAT GCCTTTTTTT TTTTTTTTG TAAAATTC                              338

(2) INFORMATION FOR SEQ ID NO: 139:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 139:

```
GGGAATCTTG GTTTTTGGCA TCTGGTTTGC CTATAGCCGA GGCCACTTTG ACAGAACAAA      60

GAAAGGGACT TCGAGTAAGA AGGTGATTTA CAGCCAGCCT AGTGCCCGAA GTGAAGGAGA     120

ATTCAAACAG ACCTCGTCAT TCCTGGTGTG AGCCTGGTCG GCTCACCGCC TATCATCTGC     180

ATTTGCCTTA CTCAGGTGCT ACCGGACTCT GGCCCCTGAT GTCTGTAGTT TCACAGGATG     240

CCTTATTTGT CTTCTACACC CCACAGGGCC CCCTACTTCT TCGGATGTGT TTTTAATAAT     300

GTCAGCTATG TGCCCCATCC TCCTTCATGC CCTCCCTCCC TTTCCTACCA CTGCTGAGTG     360

GCCTGGAACT TGTTTAAAGT GT                                              382
```

(2) INFORMATION FOR SEQ ID NO: 140:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 140:

```
ACCAAANCTT CTTTCTGTTG TGTTNGATTT TACTATAGGG GTTTNGCTTN TTCTAAANAT      60

ACTTTTCATT TAACANCTTT TGTTAAGTGT CAGGCTGCAC TTTGCTCCAT ANAATTATTG     120

TTTTCACATT TCAACTTGTA TGTGTTTGTC TCTTANAGCA TTGGTGAAAT CACATATTTT     180

ATATTCAGCA TAAAGGAGAA                                                 200
```

(2) INFORMATION FOR SEQ ID NO: 141:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 141:

```
ACTTTATTTT CAAAACACTC ATATGTTGCA AAAAACACAT AGAAAAATAA AGTTTGGTGG      60

GGGTGCTGAC TAAACTTCAA GTCACAGACT TTTATGTGAC AGATTGGAGC AGGGTTTGTT     120

ATGCATGTAG AGAACCCAAA CTAATTTATT AAACAGGATA GAAACAGGCT GTCTGGGTGA     180

AATGGTTCTG AGAACCATCC AATTCACCTG TCAGATGCTG ATANACTAGC TCTTCAGATG     240

TTTTTCTACC AGTTCAGAGA TNGGTTAATG ACTANTTCCA ATGGGAAAA AGCAAGATGG      300

ATTCACAAAC CAAGTAATTT TAAACAAAGA CACTT                                335
```

(2) INFORMATION FOR SEQ ID NO: 142:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO: 142:

```
ACCAGGTTAA TATTGCCACA TATATCCTTT CCAATTGCGG GCTAAACAGA CGTGTATTTA      60
GGGTTGTTTA AAGACAACCC AGCTTAATAT CAAGAGAAAT TGTGACCTTT CATGGAGTAT     120
CTGATGGAGA AAACACTGAG TTTTGACAAA TCTTATTTTA TTCAGATAGC AGTCTGATCA     180
CACATGGTCC AACAACACTC AAATAATAAA TCAAATATNA TCAGATGTTA AAGATTGGTC     240
TTCAAACATC ATAGCCAATG ATGCCCCGCT TGCCTATAAT CTCTCCGACA TAAAACCACA     300
TCAACACCTC AGTGGCCACC AAACCATTCA GCACAGCTTC CTTAACTGTG AGCTGTTTGA     360
AGCTACCAGT CTGAGCACTA TTGACTATNT TTTTCANGCT CTGAATAGCT CTAGGGATCT     420
CAGCANGGGT GGGAGGAACC AGCTCAACCT TGGCGTANT                            459
```

(2) INFORMATION FOR SEQ ID NO: 143:

(i) SEQUENCE CHARACTERISTICS:
       (A) LENGTH: 140 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Homo sapiens (xi) SEQUENCE DESCRIPTION: SEQ ID NO: 143:

```
ACATTTCCTT CCACCAAGTC AGGACTCCTG GCTTCTGTGG GAGTTCTTAT CACCTGAGGG      60
AAATCCAAAC AGTCTCTCCT AGAAAGGAAT AGTGTCACCA ACCCCACCCA TCTCCCTGAG     120
ACCATCCGAC TTCCCTGTGT                                                 140
```

(2) INFORMATION FOR SEQ ID NO: 144:

(i) SEQUENCE CHARACTERISTICS:
       (A) LENGTH: 164 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Homo sapiens (xi) SEQUENCE DESCRIPTION: SEQ ID NO: 144:

```
ACTTCAGTAA CAACATACAA TAACAACATT AAGTGTATAT TGCCATCTTT GTCATTTTCT      60
ATCTATACCA CTCTCCCTTC TGAAAACAAN AATCACTANC CAATCACTTA TACAAATTTG     120
AGGCAATTAA TCCATATTTG TTTTCAATAA GGAAAAAAAG ATGT                      164
```

(2) INFORMATION FOR SEQ ID NO: 145:

(i) SEQUENCE CHARACTERISTICS:
       (A) LENGTH: 303 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Homo sapiens (xi) SEQUENCE DESCRIPTION: SEQ ID NO: 145:

ACGTAGACCA TCCAACTTTG TATTTGTAAT GGCAAACATC CAGNAGCAAT TCCTAAACAA      60

ACTGGAGGGT ATTTATACCC AATTATCCCA TTCATTAACA TGCCCTCCTC CTCAGGCTAT     120

GCAGGACAGC TATCATAAGT CGGCCCAGGC ATCCAGATAC TACCATTTGT ATAAACTTCA     180

GTAGGGGAGT CCATCCAAGT GACAGGTCTA ATCAAAGGAG GAAATGGAAC ATAAGCCCAG     240

TAGTAAAATN TTGCTTAGCT GAAACAGCCA CAAAAGACTT ACCGCCGTGG TGATTACCAT     300

CAA                                                                  303

(2) INFORMATION FOR SEQ ID NO: 146:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 146:

ACTGCAGCTC AATTAGAAGT GGTCTCTGAC TTTCATCANC TTCTCCCTGG GCTCCATGAC      60

ACTGGCCTGG AGTGACTCAT TGCTCTGGTT GGTTGAGAGA GCTCCTTTGC CAACAGGCCT     120

CCAAGTCAGG GCTGGGATTT GTTTCCTTTC CACATTCTAG CAACAATATG CTGGCCACTT     180

CCTGAACAGG GAGGGTGGGA GGAGCCAGCA TGGAACAAGC TGCCACTTTC TAAAGTAGCC     240

AGACTTGCCC CTGGGCCTGT CACACCTACT GATGACCTTC TGTGCCTGCA GGATGGAATG     300

TAGGGGTGAG CTGTGTGACT CTATGGT                                        327

(2) INFORMATION FOR SEQ ID NO: 147:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 147:

ACATTGTTTT TTTGAGATAA AGCATTGANA GAGCTCTCCT TAACGTGACA CAATGGAAGG      60

ACTGGAACAC ATACCCACAT CTTTGTTCTG AGGGATAATT TTCTGATAAA GTCTTGCTGT     120

ATATTCAAGC ACATATGTTA TATATTATTC AGTTCCATGT TTATAGCCTA GTT            173

(2) INFORMATION FOR SEQ ID NO: 148:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 148:

```
ACAACCACTT TATCTCATCG AATTTTTAAC CCAAACTCAC TCACTGTGCC TTTCTATCCT      60
ATGGGATATA TTATTTGATG CTCCATTTCA TCACACATAT ATGAATAATA CACTCATACT     120
GCCCTACTAC CTGCTGCAAT AATCACATTC CCTTCCTGTC CTGACCCTGA AGCCATTGGG     180
GTGGTCCTAG TGGCCATCAG TCCANGCCTG CACCTTGAGC CCTTGAGCTC CATTGCTCAC     240
NCCANCCCAC CTCACCGACC CCATCCTCTT ACACAGCTAC CTCCTTGCTC TCTAACCCCA     300
TAGATTATNT CCAAATTCAG TCAATTAAGT TACTATTAAC ACTCTACCCG ACATGTCCAG     360
CACCACTGGT AAGCCTTCTC CAGCCAACAC ACACACACAC ACACNCACAC ACACACATAT     420
CCAGGCACAG GCTACCTCAT CTTCACAATC ACCCCTTTAA TTACCATGCT ATGGTGG       477
```

(2) INFORMATION FOR SEQ ID NO: 149:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 149:

```
ACAGTTGTAT TATAATATCA AGAAATAAAC TTGCAATGAG AGCATTTAAG AGGGAAGAAC      60
TAACGTATTT TAGAGAGCCA AGGAAGGTTT CTGTGGGGAG TGGGATGTAA GGTGGGGCCT     120
GATGATAAAT AAGAGTCAGC CAGGTAAGTG GGTGGTGTGG TATGGGCACA GTGAAGAACA     180
TTTCAGGCAG AGGGAACAGC AGTGAAA                                        207
```

(2) INFORMATION FOR SEQ ID NO: 150:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 150:

```
ACCTTGATTT CATTGCTGCT CTGATGGAAA CCCAACTATC TAATTTAGCT AAAACATGGG      60
CACTTAAATG TGGTCAGTGT TTGGACTTGT TAACTANTGG CATCTTTGGG T              111
```

(2) INFORMATION FOR SEQ ID NO: 151:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 151:

```
AGCGCGGCAG GTCATATTGA ACATTCCAGA TACCTATCAT TACTCGATGC TGTTGATAAC      60
```

AGCAAGATGG CTTTGAACTC AGGGTCACCA CCAGCTATTG GACCTTACTA TGAAAACCAT        120

GGATACCAAC CGGAAAACCC CTATCCCGCA CAGCCCACTG TGGTCCCCAC TGTCTACGAG        180

GTGCATCCGG CTCAGT                                                       196

(2) INFORMATION FOR SEQ ID NO: 152:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 152:

ACAGCACTTT CACATGTAAG AAGGGAGAAA TTCCTAAATG TAGGAGAAAG ATAACAGAAC         60

CTTCCCCTTT TCATCTAGTG GTGGAAACCT GATGCTTTAT GTTGACAGGA ATAGAACCAG        120

GAGGGAGTTT GT                                                           132

(2) INFORMATION FOR SEQ ID NO: 153:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 153:

ACAANACCCA NGANAGGCCA CTGGCCGTGG TGTCATGGCC TCCAAACATG AAAGTGTCAG         60

CTTCTGCTCT TATGTCCTCA TCTGACAACT CTTTACCATT TTTATCCTCG CTCAGCAGGA        120

GCACATCAAT AAAGTCCAAA GTCTTGGACT TGGCCTTGGC TTGGAGGAAG TCATCAACAC        180

CCTGGCTAGT GAGGGTGCGG CGCCGCTCCT GGATGACGGC ATCTGTGAAG TCGTGCACCA        240

GTCTGCAGGC CCTGTGGAAG CGCCGTCCAC ACGGAGTNAG GAATT                       285

(2) INFORMATION FOR SEQ ID NO: 154:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 154:

ACCACAGTCC TGTTGGGCCA GGGCTTCATG ACCCTTTCTG TGAAAAGCCA TATTATCACC         60

ACCCCAAATT TTTCCTTAAA TATCTTTAAC TGAAGGGGTC AGCCTCTTGA CTGCAAAGAC        120

CCTAAGCCGG TTACACAGCT AACTCCCACT GGCCCTGATT TGTGAAATTG CTGCTGCCTG        180

ATTGGCACAG GAGTCGAAGG TGTTCAGCTC CCCTCCTCCG TGGAACGAGA CTCTGATTTG        240

```
AGTTTCACAA ATTCTCGGGC CACCTCGTCA TTGCTCCTCT GAAATAAAAT CCGGAGAATG      300

GTCAGGCCTG TCTCATCCAT ATGGATCTTC CGG                                  333
```

(2) INFORMATION FOR SEQ ID NO: 155:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 155:

```
ACTGGAAATA ATAAAACCCA CATCACAGTG TTGTGTCAAA GATCATCAGG GCATGGATGG       60

GAAAGTGCTT TGGGAACTGT AAAGTGCCTA ACACATGATC GATGATTTTT GTTATAATAT      120

TTGAATCACG GTGCATACAA ACTCTCCTGC CTGCTCCTCC TGGGCCCCAG CCCCAGCCCC      180

ATCACAGCTC ACTGCTCTGT TCATCCAGGC CCAGCATGTA GTGGCTGATT CTTCTTGGCT      240

GCTTTTAGCC TCCANAAGTT TCTCTGAAGC CAACCAAACC TCTANGTGTA AGGCATGCTG      300

GCCCTGGT                                                              308
```

(2) INFORMATION FOR SEQ ID NO: 156:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 156:

```
ACCTTGCTCG GTGCTTGGAA CATATTAGGA ACTCAAAATA TGAGATGATA ACAGTGCCTA       60

TTATTGATTA CTGAGAGAAC TGTTAGACAT TTAGTTGAAG ATTTTCTACA CAGGAACTGA      120

GAATAGGAGA TTATGTTTGG CCCTCATATT CTCTCCTATC CTCCTTGCCT CATTCTATGT      180

CTAATATATT CTCAATCAAA TAAGGTTAGC ATAATCAGGA AATCGACCAA ATACCAATAT      240

AAAACCAGAT GTCTATCCTT AAGATTTTCA AATAGAAAAC AAATTAACAG ACTAT          295
```

(2) INFORMATION FOR SEQ ID NO: 157:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 157:

```
ACAAGTTTAA ATAGTGCTGT CACTGTGCAT GTGCTGAAAT GTGAAATCCA CCACATTTCT       60

GAAGAGCAAA ACAAATTCTG TCATGTAATC TCTATCTTGG GTCGTGGGTA TATCTGTCCC      120

CTTAGT                                                                126
```

(2) INFORMATION FOR SEQ ID NO: 158:

(i) SEQUENCE CHARACTERISTICS:
        (A) LENGTH: 442 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 158:

```
ACCCACTGGT CTTGGAAACA CCCATCCTTA ATACGATGAT TTTTCTGTCG TGTGAAAATG     60

AANCCAGCAG GCTGCCCCTA GTCAGTCCTT CCTTCCAGAG AAAAAGAGAT TTGAGAAAGT    120

GCCTGGGTAA TTCACCATTA ATTTCCTCCC CCAAACTCTC TGAGTCTTCC CTTAATATTT    180

CTGGTGGTTC TGACCAAAGC AGGTCATGGT TTGTTGAGCA TTTGGGATCC CAGTGAAGTA    240

NATGTTTGTA GCCTTGCATA CTTAGCCCTT CCCACGCACA AACGGAGTGG CAGAGTGGTG    300

CCAACCCTGT TTTCCCAGTC CACGTAGACA GATTCACAGT GCGGAATTCT GGAAGCTGGA    360

NACAGACGGG CTCTTTGCAG AGCCGGGACT CTGAGANGGA CATGAGGGCC TCTGCCTCTG    420

TGTTCATTCT CTGATGTCCT GT                                            442
```

(2) INFORMATION FOR SEQ ID NO: 159:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 159:

```
ACTTCCAGGT AACGTTGTTG TTTCCGTTGA GCCTGAACTG ATGGGTGACG TTGTAGGTTC     60

TCCAACAAGA ACTGAGGTTG CAGAGCGGGT AGGGAAGAGT GCTGTTCCAG TTGCACCTGG    120

GCTGCTGTGG ACTGTTGTTG ATTCCTCACT ACGGCCCAAG GTTGTGGAAC TGGCANAAAG    180

GTGTGTTGTT GGANTTGAGC TCGGGCGGCT GTGGTAGGTT GTGGGCTCTT CAACAGGGGC    240

TGCTGTGGTG CCGGGANGTG AANGTGTTGT GTCACTTGAG CTTGGCCAGC TCTGAAAGT     300

ANTANATTCT TCCTGAAGGC CAGCGCTTGT GGAGCTGGCA NGGGTCANTG TTGTGTGTAA    360

CGAACCAGTG CTGCTGTGGG TGGGTGTANA TCCTCCACAA AGCCTGAAGT TATGGTGTCN    420

TCAGGTAANA ATGTGGTTTC AGTGTCCCTG GGCNGCTGTG GAAGGTTGTA NATTGTCACC    480

AAGGGAATAA GCTGTGGT                                                 498
```

(2) INFORMATION FOR SEQ ID NO: 160:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ii) MOLECULE TYPE: cDNA (vi) ORIGINAL SOURCE:

(A) ORGANISM: Homo sapiens (xi) SEQUENCE DESCRIPTION: SEQ ID NO: 160:

ACCTGCATCC AGCTTCCCTG CCAAACTCAC AAGGAGACAT CAACCTCTAG ACAGGGAAAC        60

AGCTTCAGGA TACTTCCAGG AGACAGAGCC ACCAGCAGCA AAACAAATAT TCCCATGCCT       120

GGAGCATGGC ATAGAGGAAG CTGANAAATG TGGGGTCTGA GGAAGCCATT TGAGTCTGGC       180

CACTAGACAT CTCATCAGCC ACTTGTGTGA AGAGATGCCC CATGACCCCA GATGCCTCTC       240

CCACCCTTAC CTCCATCTCA CACACTTGAG CTTTCCACTC TGTATAATTC TAACATCCTG       300

GAGAAAAATG GCAGTTTGAC CGAACCTGTT CACAACGGTA GAGGCTGATT TCTAACGAAA       360

CTTGTAGAAT GAAGCCTGGA                                                  380

(2) INFORMATION FOR SEQ ID NO: 161:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 161:

ACTCCACATC CCCTCTGAGC AGGCGGTTGT CGTTCAAGGT GTATTTGGCC TTGCCTGTCA        60

CACTGTCCAC TGGCCCCTTA TCCACTTGGT GCTTAATCCC TCGAAAGAGC ATGT            114

(2) INFORMATION FOR SEQ ID NO: 162:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 162:

ACTTTCTGAA TCGAATCAAA TGATACTTAG TGTAGTTTTA ATATCCTCAT ATATATCAAA        60

GTTTTACTAC TCTGATAATT TTGTAAACCA GGTAACCAGA ACATCCAGTC ATACAGCTTT       120

TGGTGATATA TAACTTGGCA ATAACCCAGT CTGGTGATAC ATAAAACTAC TCACTGT         177

(2) INFORMATION FOR SEQ ID NO: 163:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 163:

CATTTATACA GACAGGCGTG AAGACATTCA CGACAAAAAC GCGAAATTCT ATCCCGTGAC        60

CANAGAAGGC AGCTACGGCT ACTCCTACAT CCTGGCGTGG GTGGCCTTCG CCTGCACCTT       120

(2) INFORMATION FOR SEQ ID NO: 164:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 164:

```
CATCAGCGGC ATGATGT                                                    137
```

(2) INFORMATION FOR SEQ ID NO: 164:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 164:

```
CTTATCACAA TGAATGTTCT CCTGGGCAGC GTTGTGATCT TTGCCACCTT CGTGACTTTA      60
TGCAATGCAT CATGCTATTT CATACCTAAT GAGGGAGTTC CAGGAGATTC AACCAGGAAA     120
TGCATGGATC TCAAAGGAAA CAAACACCCA ATAAACTCGG AGTGGCAGAC TGACAACTGT     180
GAGACATGCA CTTGCTACGA AACAGAAATT TCATGTTGCA CCCTTGTTTC TACACCTGTG     240
GGTTATGACA AGACAACTG CCAAAGAATC TTCAAGAAGG AGGACTGCAA GTATATCGTG      300
GTGGAGAAGA AGGACCCAAA AAAGACCTGT TCTGTCAGTG AATGGATAAT CTAATGTGCT     360
TCTAGTAGGC ACAGGGCTCC CAGGCCAGGC CTCATTCTCC TCTGGCCTCT AATAGTCAAT     420
GATTGTGTAG CCATGCCTAT CAGTAAAAAG ATNTTTGAGC AAACACTTT                 469
```

(2) INFORMATION FOR SEQ ID NO: 165:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 165:

```
ACAGTTTTTT ATANATATCG ACATTGCCGG CACTTGTGTT CAGTTTCATA AAGCTGGTGG      60
ATCCGCTGTC ATCCACTATT CCTTGGCTAG AGTAAAAATT ATTCTTATAG CCCATGTCCC     120
TGCAGGCCGC CCGCCCGTAG TTCTCGTTCC AGTCGTCTTG GCACACAGGG TGCCAGGACT     180
TCCTCTGAGA TGAGT                                                      195
```

(2) INFORMATION FOR SEQ ID NO: 166:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 166:

```
ACATCTTAGT AGTGTGGCAC ATCAGGGGGC CATCAGGGTC ACAGTCACTC ATAGCCTCGC      60
CGAGGTCGGA GTCCACACCA CCGGTGTAGG TGTGCTCAAT CTTGGGCTTG GCGCCCACCT     120
```

```
TTGGAGAAGG GATATGCTGC ACACACATGT CCACAAAGCC TGTGAACTCG CCAAAGAATT      180

TTTGCAGACC AGCCTGAGCA AGGGGCGGAT GTTCAGCTTC AGCTCCTCCT TCGTCAGGTG      240

GATGCCAACC TCGTCTANGG TCCGTGGGAA GCTGGTGTCC ACNTCACCTA CAACCTGGGC      300

GANGATCTTA TAAAGAGGCT CCNAGATAAA CTCCACGAAA CTTCTCTGGG AGCTGCTAGT      360

NGGGGCCTTT TTGGTGAACT TTC                                              383
```

(2) INFORMATION FOR SEQ ID NO: 167:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 167:

```
ACAGAGCCAG ACCTTGGCCA TAAATGAANC AGAGATTAAG ACTAAACCCC AAGTCGANAT       60

TGGAGCAGAA ACTGGAGCAA GAAGTGGGCC TGGGGCTGAA GTAGAGACCA AGGCCACTGC      120

TATANCCATA CACAGAGCCA ACTCTCAGGC CAAGGCNATG GTTGGGGCAG ANCCAGAGAC      180

TCAATCTGAN TCCAAAGTGG TGGCTGGAAC ACTGGTCATG ACANAGGCAG TGACTCTGAC      240

TGANGTC                                                                247
```

(2) INFORMATION FOR SEQ ID NO: 168:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 168:

```
ACTTCTAAGT TTTCTAGAAG TGGAAGGATT GTANTCATCC TGAAAATGGG TTTACTTCAA       60

AATCCCTCAN CCTTGTTCTT CACNACTGTC TATACTGANA GTGTCATGTT TCCACAAAGG      120

GCTGACACCT GAGCCTGNAT TTTCACTCAT CCCTGAGAAG CCCTTTCCAG TAGGGTGGGC      180

AATTCCCAAC TTCCTTGCCA CAAGCTTCCC AGGCTTTCTC CCCTGGAAAA CTCCAGCTTG      240

AGTCCCAGAT ACACTCATGG GCTGCCCTGG GCA                                   273
```

(2) INFORMATION FOR SEQ ID NO: 169:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 169:

```
ACAGCCTTGG CTTCCCCAAA CTCCACAGTC TCAGTGCAGA AAGATCATCT TCCAGCAGTC       60
```

```
AGCTCAGACC AGGGTCAAAG GATGTGACAT CAACAGTTTC TGGTTTCAGA ACAGGTTCTA      120

CTACTGTCAA ATGACCCCCC ATACTTCCTC AAAGGCTGTG GTAAGTTTTG CACAGGTGAG      180

GGCAGCAGAA AGGGGGTANT TACTGATGGA CACCATCTTC TCTGTATACT CCACACTGAC      240

CTTGCCATGG GCAAAGGCCC CTACCACAAA AACAATAGGA TCACTGCTGG GCACCAGCTC      300

ACGCACATCA CTGACAACCG GGATGGAAAA AGAANTGCCA ACTTTCATAC ATCCAACTGG      360

AAAGTGATCT GATACTGGAT TCTTAATTAC CTTCAAAAGC TTCTGGGGGC CATCAGCTGC      420

TCGAACACTG A                                                          431

(2) INFORMATION FOR SEQ ID NO: 170:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 170:

ACCTGTGGGC TGGGCTGTTA TGCCTGTGCC GGCTGCTGAA AGGGAGTTCA GAGGTGGAGC       60

TCAAGGAGCT CTGCAGGCAT TTTGCCAANC CTCTCCANAG CANAGGGAGC AACCTACACT      120

CCCCGCTAGA AAGACACCAG ATTGGAGTCC TGGGAGGGGG AGTTGGGGTG GGCATTTGAT      180

GTATACTTGT CACCTGAATG AANGAGCCAG AGAGGAANGA GACGAANATG ANATTGGCCT      240

TCAAAGCTAG GGGTCTGGCA GGTGGA                                          266

(2) INFORMATION FOR SEQ ID NO: 171:

(i) SEQUENCE CHARACTERISTICS:
        (A) LENGTH: 1248 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 171:

GGCAGCCAAA TCATAAACGG CGAGGACTGC AGCCCGCACT CGCAGCCCTG GCAGGCGGCA       60

CTGGTCATGG AAAACGAATT GTTCTGCTCG GGCGTCCTGG TGCATCCGCA GTGGGTGCTG      120

TCAGCCGCAC ACTGTTTCCA GAAGTGAGTG CAGAGCTCCT ACACCATCGG GCTGGGCCTG      180

CACAGTCTTG AGGCCGACCA AGAGCCAGGG AGCCAGATGT GGAGGCCAG  CCTCTCCGTA      240

CGGCACCCAG AGTACAACAG ACCCTTGCTC GCTAACGACC TCATGCTCAT CAAGTTGGAC      300

GAATCCGTGT CCGAGTCTGA CACCATCCGG AGCATCAGCA TTGCTTCGCA GTGCCCTACC      360

GCGGGGAACT CTTGCCTCGT TTCTGGCTGG GGTCTGCTGG CGAACGGCAG AATGCCTACC      420

GTGCTGCAGT GCGTGAACGT GTCGGTGGTG TCTGAGGAGG TCTGCAGTAA GCTCTATGAC      480

CCGCTGTACC ACCCCAGCAT GTTCTGCGCC GGCGGAGGGC AAGACCAGAA GGACTCCTGC      540

AACGGTGACT CTGGGGGGCC CCTGATCTGC AACGGGTACT GCAGGGCCT  TGTGTCTTTC      600

GGAAAAGCCC CGTGTGGCCA AGTTGGCGTG CCAGGTGTCT ACACCAACCT CTGCAAATTC      660
```

```
ACTGAGTGGA TAGAGAAAAC CGTCCAGGCC AGTTAACTCT GGGGACTGGG AACCCATGAA      720

ATTGACCCCC AAATACATCC TGCGGAAGGA ATTCAGGAAT ATCTGTTCCC AGCCCCTCCT      780

CCCTCAGGCC CAGGAGTCCA GGCCCCCAGC CCCTCCTCCC TCAAACCAAG GGTACAGATC      840

CCCAGCCCCT CCTCCCTCAG ACCCAGGAGT CCAGACCCCC CAGCCCCTCC TCCCTCAGAC      900

CCAGGAGTCC AGCCCCTCCT CCCTCAGACC CAGGAGTCCA GACCCCCAG CCCCTCCTCC       960

CTCAGACCCA GGGGTCCAGG CCCCCAACCC CTCCTCCCTC AGACTCAGAG GTCCAAGCCC     1020

CCAACCCNTC ATTCCCCAGA CCCAGAGGTC CAGGTCCCAG CCCCTCNTCC CTCAGACCCA     1080

GCGGTCCAAT GCCACCTAGA CTNTCCCTGT ACACAGTGCC CCCTTGTGGC ACGTTGACCC     1140

AACCTTACCA GTTGGTTTTT CATTTTTNGT CCCTTTCCCC TAGATCCAGA AATAAAGTTT     1200

AAGAGAAGNG CAAAAAAAAA AAAAAAAAAA AAAAAAAAAA AAAAAAAA                  1248
```

(2) INFORMATION FOR SEQ ID NO: 172:

(i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 172:

```
Met Val Glu Ala Ser Leu Ser Val Arg His Pro Glu Tyr Asn Arg Pro
1               5                   10                  15

Leu Leu Ala Asn Asp Leu Met Leu Ile Lys Leu Asp Glu Ser Val Ser
            20                  25                  30

Glu Ser Asp Thr Ile Arg Ser Ile Ser Ile Ala Ser Gln Cys Pro Thr
        35                  40                  45

Ala Gly Asn Ser Cys Leu Val Ser Gly Trp Gly Leu Leu Ala Asn Gly
    50                  55                  60

Arg Met Pro Thr Val Leu Gln Cys Val Asn Val Ser Val Val Ser Glu
65                  70                  75                  80

Glu Val Cys Ser Lys Leu Tyr Asp Pro Leu Tyr His Pro Ser Met Phe
                85                  90                  95

Cys Ala Gly Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
        115                 120                 125

Gly Lys Ala Pro Cys Gly Gln Val Gly Val Pro Gly Val Tyr Thr Asn
    130                 135                 140

Leu Cys Lys Phe Thr Glu Trp Ile Glu Lys Thr Val Gln Ala Ser
145                 150                 155
```

(2) INFORMATION FOR SEQ ID NO: 173:

(i) SEQUENCE CHARACTERISTICS:
        (A) LENGTH: 1265 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 173:

```
GGCAGCCCGC ACTCGCAGCC CTGGCAGGCG GCACTGGTCA TGGAAAACGA ATTGTTCTGC      60
TCGGGCGTCC TGGTGCATCC GCAGTGGGTG CTGTCAGCCG CACACTGTTT CCAGAACTCC     120
TACACCATCG GGCTGGGCCT GCACAGTCTT GAGGCCGACC AAGAGCCAGG GAGCCAGATG     180
GTGGAGGCCA GCCTCTCCGT ACGGCACCCA GAGTACAACA GACCCTTGCT CGCTAACGAC     240
CTCATGCTCA TCAAGTTGGA CGAATCCGTG TCCGAGTCTG ACACCATCCG GAGCATCAGC     300
ATTGCTTCGC AGTGCCCTAC CGCGGGGAAC TCTTGCCTCG TTTCTGGCTG GGGTCTGCTG     360
GCGAACGGTG AGCTCACGGG TGTGTGTCTG CCCTCTTCAA GGAGGTCCTC TGCCCAGTCG     420
CGGGGGCTGA CCCAGAGCTC TGCGTCCCAG GCAGAATGCC TACCGTGCTG CAGTGCGTGA     480
ACGTGTCGGT GGTGTCTGAG GAGGTCTGCA GTAAGCTCTA TGACCCGCTG TACCACCCCA     540
GCATGTTCTG CGCCGGCGGA GGGCAAGACC AGAAGGACTC CTGCAACGGT GACTCTGGGG     600
GGCCCCTGAT CTGCAACGGG TACTTGCAGG GCCTTGTGTC TTTCGGAAAA GCCCCGTGTG     660
GCCAAGTTGG CGTGCCAGGT GTCTACACCA ACCTCTGCAA ATTCACTGAG TGGATAGAGA     720
AAACCGTCCA GGCCAGTTAA CTCTGGGGAC TGGGAACCCA TGAAATTGAC CCCCAAATAC     780
ATCCTGCGGA AGGAATTCAG GAATATCTGT TCCCAGCCCC TCCTCCCTCA GGCCCAGGAG     840
TCCAGGCCCC CAGCCCCTCC TCCCTCAAAC CAAGGGTACA GATCCCCAGC CCCTCCTCCC     900
TCAGACCCAG GAGTCCAGAC CCCCCAGCCC CTCCTCCCTC AGACCCAGGA GTCCAGCCCC     960
TCCTCCNTCA GACCCAGGAG TCCAGACCCC CCAGCCCCTC CTCCCTCAGA CCCAGGGGTT    1020
GAGGCCCCCA ACCCCTCCTC CTTCAGAGTC AGAGGTCCAA GCCCCCAACC CCTCGTTCCC    1080
CAGACCCAGA GGTNNAGGTC CCAGCCCCTC TTCCNTCAGA CCCAGNGGTC CAATGCCACC    1140
TAGATTTTCC CTGNACACAG TGCCCCCTTG TGGNANGTTG ACCCAACCTT ACCAGTTGGT    1200
TTTTCATTTT TNGTCCCTTT CCCCTAGATC CAGAAATAAA GTTTAAGAGA NGNGCAAAAA    1260
AAAAA                                                                1265
```

(2) INFORMATION FOR SEQ ID NO: 174:

(i) SEQUENCE CHARACTERISTICS:
        (A) LENGTH: 1459 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 174:

```
GGTCAGCCGC ACACTGTTTC CAGAAGTGAG TGCAGAGCTC CTACACCATC GGGCTGGGCC      60
TGCACAGTCT TGAGGCCGAC CAAGAGCCAG GGAGCCAGAT GGTGGAGGCC AGCCTCTCCG     120
TACGGCACCC AGAGTACAAC AGACCCTTGC TCGCTAACGA CCTCATGCTC ATCAAGTTGG     180
ACGAATCCGT GTCCGAGTCT GACACCATCC GGAGCATCAG CATTGCTTCG CAGTGCCCTA     240
CCGCGGGGAA CTCTTGCCTC GTTTCTGGCT GGGGTCTGCT GGCGAACGGT GAGCTCACGG     300
GTGTGTGTCT GCCCTCTTCA AGGAGGTCCT CTGCCCAGTC GCGGGGGCTG ACCCAGAGCT     360
CTGCGTCCCA GGCAGAATGC CTACCGTGCT GCAGTGCGTG AACGTGTCGG TGGTGTCTGA     420
NGAGGTCTGC ANTAAGCTCT ATGACCCGCT GTACCACCCC ANCATGTTCT GCGCCGGCGG     480
```

```
AGGGCAAGAC CAGAAGGACT CCTGCAACGT GAGAGAGGGG AAAGGGGAGG GCAGGCGACT       540

CAGGGAAGGG TGGAGAAGGG GGAGACAGAG ACACACAGGG CCGCATGGCG AGATGCAGAG       600

ATGGAGAGAC ACACAGGGAG ACAGTGACAA CTAGAGAGAG AAACTGAGAG AAACAGAGAA       660

ATAAACACAG GAATAAAGAG AAGCAAAGGA AGAGAGAAAC AGAAACAGAC ATGGGGAGGC       720

AGAAACACAC ACACATAGAA ATGCAGTTGA CCTTCCAACA GCATGGGGCC TGAGGGCGGT       780

GACCTCCACC CAATAGAAAA TCCTCTTATA ACTTTTGACT CCCCAAAAAC CTGACTAGAA       840

ATAGCCTACT GTTGACGGGG AGCCTTACCA ATAACATAAA TAGTCGATTT ATGCATACGT       900

TTTATGCATT CATGATATAC CTTTGTTGGA ATTTTTTGAT ATTTCTAAGC TACACAGTTC       960

GTCTGTGAAT TTTTTTAAAT TGTTGCAACT CTCCTAAAAT TTTTCTGATG TGTTTATTGA      1020

AAAAATCCAA GTATAAGTGG ACTTGTGCAT TCAAACCAGG GTTGTTCAAG GGTCAACTGT      1080

GTACCCAGAG GGAAACAGTG ACACAGATTC ATAGAGGTGA AACACGAAGA GAAACAGGAA      1140

AAATCAAGAC TCTACAAAGA GGCTGGGCAG GGTGGCTCAT GCCTGTAATC CCAGCACTTT      1200

GGGAGGCGAG GCAGGCAGAT CACTTGAGGT AAGGAGTTCA AGACCAGCCT GGCCAAAATG      1260

GTGAAATCCT GTCTGTACTA AAAATACAAA AGTTAGCTGG ATATGGTGGC AGGCGCCTGT      1320

AATCCCAGCT ACTTGGGAGG CTGAGGCAGG AGAATTGCTT GAATATGGGA GGCAGAGGTT      1380

GAAGTGAGTT GAGATCACAC CACTATACTC CAGCTGGGGC AACAGAGTAA GACTCTGTCT      1440

CAAAAAAAAA AAAAAAAA                                                   1459

(2) INFORMATION FOR SEQ ID NO: 175:

(i) SEQUENCE CHARACTERISTICS:
        (A) LENGTH: 1167 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 175:

GCGCAGCCCT GGCAGGCGGC ACTGGTCATG GAAAACGAAT TGTTCTGCTC GGGCGTCCTG        60

GTGCATCCGC AGTGGGTGCT GTCAGCCGCA CACTGTTTCC AGAACTCCTA CACCATCGGG       120

CTGGGCCTGC ACAGTCTTGA GGCCGACCAA GAGCCAGGGA GCCAGATGGT GGAGGCCAGC       180

CTCTCCGTAC GGCACCCAGA GTACAACAGA CTCTTGCTCG CTAACGACCT CATGCTCATC       240

AAGTTGGACG AATCCGTGTC CGAGTCTGAC ACCATCCGGA GCATCAGCAT TGCTTCGCAG       300

TGCCCTACCG CGGGGAACTC TTGCCTCGTN TCTGGCTGGG GTCTGCTGGC GAACGGCAGA       360

ATGCCTACCG TGCTGCACTG CGTGAACGTG TCGGTGGTGT CTGAGGANGT CTGCAGTAAG       420

CTCTATGACC CGCTGTACCA CCCCAGCATG TTCTGCGCCG GCGGAGGGCA AGACCAGAAG       480

GACTCCTGCA ACGGTGACTC TGGGGGGCCC CTGATCTGCA ACGGGTACTT GCAGGGCCTT       540

GTGTCTTTCG GAAAAGCCCC GTGTGGCCAA CTTGGCGTGC CAGGTGTCTA CACCAACCTC       600

TGCAAATTCA CTGAGTGGAT AGAGAAAACC GTCCAGNCCA GTTAACTCTG GGACTGGGA       660

ACCCATGAAA TTGACCCCCA AATACATCCT GCGGAANGAA TTCAGGAATA TCTGTTCCCA       720

GCCCCTCCTC CCTCAGGCCC AGGAGTCCAG GCCCCCAGCC CCTCCTCCCT CAAACCAAGG       780

GTACAGATCC CCAGCCCCTC CTCCCTCAGA CCCAGGAGTC CAGACCCCCC AGCCCCTCNT       840

CCNTCAGACC CAGGAGTCCA GCCCCTCCTC CNTCAGACGC AGGAGTCCAG ACCCCCCAGC       900
```

```
CCNTCNTCCG TCAGACCCAG GGGTGCAGGC CCCCAACCCC TCNTCCNTCA GAGTCAGAGG      960

TCCAAGCCCC CAACCCCTCG TTCCCCAGAC CCAGAGGTNC AGGTCCCAGC CCCTCCTCCC     1020

TCAGACCCAG CGGTCCAATG CCACCTAGAN TNTCCCTGTA CACAGTGCCC CCTTGTGGCA     1080

NGTTGACCCA ACCTTACCAG TTGGTTTTTC ATTTTTTGTC CCTTTCCCCT AGATCCAGAA     1140

ATAAAGTNTA AGAGAAGCGC AAAAAAA                                         1167
```

(2) INFORMATION FOR SEQ ID NO: 176:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 176:

```
Met Glu Asn Glu Leu Phe Cys Ser Gly Val Leu Val His Pro Gln Trp
1               5                   10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Leu Leu Leu
50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Gly Arg Met
            100                 105                 110

Pro Thr Val Leu His Cys Val Asn Val Ser Val Val Ser Glu Xaa Val
        115                 120                 125

Cys Ser Lys Leu Tyr Asp Pro Leu Tyr His Pro Ser Met Phe Cys Ala
130                 135                 140

Gly Gly Gly Gln Asp Gln Lys Asp Ser Cys Asn Gly Asp Ser Gly Gly
145                 150                 155                 160

Pro Leu Ile Cys Asn Gly Tyr Leu Gln Gly Leu Val Ser Phe Gly Lys
                165                 170                 175

Ala Pro Cys Gly Gln Leu Gly Val Pro Gly Val Tyr Thr Asn Leu Cys
            180                 185                 190

Lys Phe Thr Glu Trp Ile Glu Lys Thr Val Gln Xaa Ser
        195                 200                 205
```

(2) INFORMATION FOR SEQ ID NO: 177:

(i) SEQUENCE CHARACTERISTICS:
        (A) LENGTH: 1119 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 177:

```
GCGCACTCGC AGCCCTGGCA GGCGGCACTG GTCATGGAAA ACGAATTGTT CTGCTCGGGC      60
GTCCTGGTGC ATCCGCAGTG GGTGCTGTCA GCCGCACACT GTTTCCAGAA CTCCTACACC     120
ATCGGGCTGG GCCTGCACAG TCTTGAGGCC GACCAAGAGC CAGGGAGCCA GATGGTGGAG     180
GCCAGCCTCT CCGTACGGCA CCCAGAGTAC AACAGACCCT TGCTCGCTAA CGACCTCATG     240
CTCATCAAGT TGGACGAATC CGTGTCCGAG TCTGACACCA TCCGGAGCAT CAGCATTGCT     300
TCGCAGTGCC CTACCGCGGG GAACTCTTGC CTCGTTTCTG GCTGGGGTCT GCTGGCGAAC     360
GATGCTGTGA TTGCCATCCA GTCCCAGACT GTGGGAGGCT GGGAGTGTGA GAAGCTTTCC     420
CAACCCTGGC AGGGTTGTAC CATTTCGGCA ACTTCCAGTG CAAGGACGTC CTGCTGCATC     480
CTCACTGGGT GCTCACTACT GCTCACTGCA TCACCCGGAA CACTGTGATC AACTAGCCAG     540
CACCATAGTT CTCCGAAGTC AGACTATCAT GATTACTGTG TTGACTGTGC TGTCTATTGT     600
ACTAACCATG CCGATGTTTA GGTGAAATTA GCGTCACTTG GCCTCAACCA TCTTGGTATC     660
CAGTTATCCT CACTGAATTG AGATTTCCTG CTTCAGTGTC AGCCATTCCC ACATAATTTC     720
TGACCTACAG AGGTGAGGGA TCATATAGCT CTTCAAGGAT GCTGGTACTC CCCTCACAAA     780
TTCATTTCTC CTGTTGTAGT GAAAGGTGCG CCCTCTGGAG CCTCCCAGGG TGGGTGTGCA     840
GGTCACAATG ATGAATGTAT GATCGTGTTC CCATTACCCA AAGCCTTTAA ATCCCTCATG     900
CTCAGTACAC CAGGGCAGGT CTAGCATTTC TTCATTTAGT GTATGCTGTC CATTCATGCA     960
ACCACCTCAG GACTCCTGGA TTCTCTGCCT AGTTGAGCTC CTGCATGCTG CCTCCTTGGG    1020
GAGGTGAGGG AGAGGGCCCA TGGTTCAATG GGATCTGTGC AGTTGTAACA CATTAGGTGC    1080
TTAATAAACA GAAGCTGTGA TGTTAAAAAA AAAAAAAA                             1119
```

(2) INFORMATION FOR SEQ ID NO: 178:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO: 178:

```
Met Glu Asn Glu Leu Phe Cys Ser Gly Val Leu Val His Pro Gln Trp
1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Pro Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Gly Trp Glu Cys Glu Lys Leu
```

```
                115                 120                 125
Ser Gln Pro Trp Gln Gly Cys Thr Ile Ser Ala Thr Ser Ser Ala Arg
    130                 135                 140

Thr Ser Cys Cys Ile Leu Thr Gly Cys Ser Leu Leu Thr Ala Ser
145                 150                 155                 160

Pro Gly Thr Leu (2) INFORMATION FOR SEQ ID NO: 179:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (xi) SEQUENCE DESCRIPTION: SEQ ID NO: 179:

CTGGAGTGCC TTGGTGTTTC AAGCCCCTGC AGGAAGCAGA ATGCACCTTC TGAGGCACCT         60

CCAGCTGCCC CCGGCCGGGG GATGCGAGGC TCGGAGCACC CTTGCCCGGC TGTGATTGCT        120

GCCAGGCACT GTTCATCTCA GCTTTTCTGT CCCTTTGCTC CCGGCAAGCG CTTCTGCTGA        180

AAGTTCATAT CTGGAGCCTG ATGTCTTAAC GAATAAAGGT CCCATGCTCC ACCCGAAAAA        240

AAAAAAAAAA                                                              250

(2) INFORMATION FOR SEQ ID NO: 180:

(i) SEQUENCE CHARACTERISTICS:
        (A) LENGTH: 202 base pairs
        (B) TYPE: nucleic acid
        (C) STRANDEDNESS: single
        (D) TOPOLOGY: linear (xi) SEQUENCE DESCRIPTION: SEQ ID NO: 180:

ACTAGTCCAG TGTGGTGGAA TTCCATTGTG TTGGGCCCAA CACAATGGCT ACCTTTAACA         60

TCACCCAGAC CCCGCCCCTG CCCGTGCCCC ACGCTGCTGC TAACGACAGT ATGATGCTTA        120

CTCTGCTACT CGGAAACTAT TTTTATGTAA TTAATGTATG CTTTCTTGTT TATAAATGCC        180

TGATTTAAAA AAAAAAAAA AA                                                 202

(2) INFORMATION FOR SEQ ID NO: 181:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (xi) SEQUENCE DESCRIPTION: SEQ ID NO: 181:

TCCYTTTGKT NAGGTTTKKG AGACAMCCCK AGACCTWAAN CTGTGTCACA GACTTCYNGG         60

AATGTTTAGG CAGTGCTAGT AATTTCYTCG TAATGATTCT GTTATTACTT TCCTNATTCT        120

TTATTCCTCT TTCTTCTGAA GATTAATGAA GTTGAAAATT GAGGTGGATA AATACAAAAA        180

GGTAGTGTGA TAGTATAAGT ATCTAAGTGC AGATGAAAGT GTGTTATATA TATCCATTCA        240

AAATTATGCA AGTTAGTAAT TACTCAGGGT TAACTAAATT ACTTTAATAT GCTGTTGAAC        300

CTACTCTGTT CCTTGGCTAG AAAAAATTAT AAACAGGACT TTGTTAGTTT GGGAAGCCAA        360

ATTGATAATA TTCTATGTTC TAAAAGTTGG GCTATACATA AATTATTAAG AAATATGGAW        420

TTTTATTCCC AGGAATATGG KGTTCATTTT ATGAATATTA CSCRGGATAG AWGTWTGAGT        480

AAAAYCAGTT TTGGTWAATA YGTWAATATG TCMTAAATAA ACAAKGCTTT GACTTATTTC        540
```

CAAAAAAAAA AAAAAAAA                                                          558

(2) INFORMATION FOR SEQ ID NO: 182:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (xi) SEQUENCE DESCRIPTION: SEQ ID NO: 182:

ACAGGGWTTK GRGGATGCTA AGSCCCCRGA RWTYGTTTGA TCCAACCCTG GCTTWTTTTC    60

AGAGGGAAA ATGGGGCCTA GAAGTTACAG MSCATYTAGY TGGTGCGMTG GCACCCCTGG    120

CSTCACACAG ASTCCCGAGT AGCTGGGACT ACAGGCACAC AGTCACTGAA GCAGGCCCTG   180

TTWGCAATTC ACGTTGCCAC CTCCAACTTA AACATTCTTC ATATGTGATG TCCTTAGTCA   240

CTAAGGTTAA ACTTTCCCAC CCAGAAAAGG CAACTTAGAT AAAATCTTAG AGTACTTTCA   300

TACTMTTCTA AGTCCTCTTC CAGCCTCACT KKGAGTCCTM CYTGGGGGTT GATAGGAANT   360

NTCTCTTGGC TTTCTCAATA AARTCTCTAT YCATCTCATG TTTAATTTGG TACGCATARA   420

AWTGSTGARA AAATTAAAAT GTTCTGGTTY MACTTTAAAA ARAAAAAAAA AAAAAAAA     479

(2) INFORMATION FOR SEQ ID NO: 183:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (xi) SEQUENCE DESCRIPTION: SEQ ID NO: 183:

AGGCGGGAGC AGAAGCTAAA GCCAAAGCCC AAGAAGAGTG GCAGTGCCAG CACTGGTGCC    60

AGTACCAGTA CCAATAACAG TGCCAGTGCC AGTGCCAGCA CCAGTGGTGG CTTCAGTGCT   120

GGTGCCAGCC TGACCGCCAC TCTCACATTT GGGCTCTTCG CTGGCCTTGG TGGAGCTGGT   180

GCCAGCACCA GTGGCAGCTC TGGTGCCTGT GGTTTCTCCT ACAAGTGAGA TTTTAGATAT   240

TGTTAATCCT GCCAGTCTTT CTCTTCAAGC CAGGGTGCAT CCTCAGAAAC CTACTCAACA   300

CAGCACTCTA GGCAGCCACT ATCAATCAAT TGAAGTTGAC ACTCTGCATT ARATCTATTT   360

GCCATTTCAA AAAAAAAAAA AAAA                                          384

(2) INFORMATION FOR SEQ ID NO: 184:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (xi) SEQUENCE DESCRIPTION: SEQ ID NO: 184:

ACCGAATTGG GACCGCTGGC TTATAAGCGA TCATGTYYNT CCRGTATKAC CTCAACGAGC    60

AGGGAGATCG AGTCTATACG CTGAAGAAAT TTGACCCGAT GGGACAACAG ACCTGCTCAG   120

CCCATCCTGC TCGGTTCTCC CCAGATGACA AATACTCTSG ACACCGAATC ACCATCAAGA   180

AACGCTTCAA GGTGCTCATG ACCCAGCAAC CGCGCCCTGT CCTCTGAGGG TCCCTTAAAC   240

TGATGTCTTT TCTGCCACCT GTTACCCCTC GGAGACTCCG TAACCAAACT CTTCGGACTG   300

TGAGCCCTGA TGCCTTTTTG CCAGCCATAC TCTTTGGCAT CCAGTCTCTC GTGGCGATTG   360

ATTATGCTTG TGTGAGGCAA TCATGGTGGC ATCACCCATA AAGGGAACAC ATTTGACTTT   420

```
TTTTTCTCAT ATTTTAAATT ACTACMAGAW TATTWMAGAW WAAATGAWTT GAAAAACTST      480

TAAAAAAAAA AAAAAA                                                     496
```

(2) INFORMATION FOR SEQ ID NO: 185:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (xi) SEQUENCE DESCRIPTION: SEQ ID NO: 185:

```
GCTGGTAGCC TATGGCGKGG CCCACGGAGG GGCTCCTGAG GCCACGGRAC AGTGACTTCC       60

CAAGTATCYT GCGCSGCGTC TTCTACCGTC CCTACCTGCA GATCTTCGGG CAGATTCCCC      120

AGGAGGACAT GGACGTGGCC CTCATGGAGC ACAGCAACTG YTCGTCGGAG CCCGGCTTCT      180

GGGCACACCC TCCTGGGGCC CAGGCGGGCA CCTGCGTCTC CCAGTATGCC AACTGGCTGG      240

TGGTGCTGCT CCTCGTCATC TTCCTGCTCG TGGCCAACAT CCTGCTGGTC AACTTGCTCA      300

TTGCCATGTT CAGTTACACA TTCGGCAAAG TACAGGGCAA CAGCGATCTC TACTGGGAAG      360

GCGCAGCGTT ACCGCCTCAT CCGG                                            384
```

(2) INFORMATION FOR SEQ ID NO: 186:

(i) SEQUENCE CHARACTERISTICS:
        (A) LENGTH: 577 base pairs
        (B) TYPE: nucleic acid
        (C) STRANDEDNESS: single
        (D) TOPOLOGY: linear (xi) SEQUENCE DESCRIPTION: SEQ ID NO: 186:

```
GAGTTAGCTC CTCCACAACC TTGATGAGGT CGTCTGCAGT GGCCTCTCGC TTCATACCGC       60

TNCCATCGTC ATACTGTAGG TTTGCCACCA CYTCCTGGCA TCTTGGGGCG GCNTAATATT      120

CCAGGAAACT CTCAATCAAG TCACCGTCGA TGAAACCTGT GGGCTGGTTC TGTCTTCCGC      180

TCGGTGTGAA AGGATCTCCC AGAAGGAGTG CTCGATCTTC CCCACACTTT TGATGACTTT      240

ATTGAGTCGA TTCTGCATGT CCAGCAGGAG GTTGTACCAG CTCTCTGACA GTGAGGTCAC      300

CAGCCCTATC ATGCCGTTGA MCGTGCCGAA GARCACCGAG CCTTGTGTGG GGGKKGAAGT      360

CTCACCCAGA TTCTGCATTA CCAGAGAGCC GTGGCAAAAG ACATTGACAA ACTCGCCCAG      420

GTGGAAAAAG AMCAMCTCCT GGARGTGCTN GCCGCTCCTC GTCMGTTGGT GGCAGCGCTW      480

TCCTTTTGAC ACACAAACAA GTTAAAGGCA TTTTCAGCCC CCAGAAANTT GTCATCATCC      540

AAGATNTCGC ACAGCACTNA TCCAGTTGGG ATTAAAT                              577
```

(2) INFORMATION FOR SEQ ID NO: 187:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (xi) SEQUENCE DESCRIPTION: SEQ ID NO: 187:

```
AACATCTTCC TGTATAATGC TGTGTAATAT CGATCCGATN TTGTCTGSTG AGAATYCATW       60

ACTKGGAAAA GMAACATTAA AGCCTGGACA CTGGTATTAA AATTCACAAT ATGCAACACT      120

TTAAACAGTG TGTCAATCTG CTCCCYYNAC TTTGTCATCA CCAGTCTGGG AAKAAGGGTA      180

TGCCCTATTC ACACCTGTTA AAAGGGCGCT AAGCATTTTT GATTCAACAT CTTTTTTTTT      240
```

| | | |
|---|---|---|
| GACACAAGTC CGAAAAAAGC AAAAGTAAAC AGTTATYAAT TTGTTAGCCA ATTCACTTTC | 300 | |
| TTCATGGGAC AGAGCCATYT GATTTAAAAA GCAAATTGCA TAATATTGAG CTTYGGGAGC | 360 | |
| TGATATTTGA GCGGAAGAGT AGCCTTTCTA CTTCACCAGA CACAACTCCC TTTCATATTG | 420 | |
| GGATGTTNAC NAAAGTWATG TCTCTWACAG ATGGGATGCT TTTGTGGCAA TTCTGTTCTG | 480 | |
| AGGATCTCCC AGTTTATTTA CCACTTGCAC AAGAAGGCGT TTTCTTCCTC AGGC | 534 | |

(2) INFORMATION FOR SEQ ID NO: 188:

(i) SEQUENCE CHARACTERISTICS:
        (A) LENGTH: 761 base pairs
        (B) TYPE: nucleic acid
        (C) STRANDEDNESS: single
        (D) TOPOLOGY: linear (xi) SEQUENCE DESCRIPTION: SEQ ID NO: 188:

| | | |
|---|---|---|
| AGAAACCAGT ATCTCTNAAA ACAACCTCTC ATACCTTGTG GACCTAATTT TGTGTGCGTG | 60 | |
| TGTGTGTGCG CGCATATTAT ATAGACAGGC ACATCTTTTT TACTTTTGTA AAAGCTTATG | 120 | |
| CCTCTTTGGT ATCTATATCT GTGAAAGTTT TAATGATCTG CCATAATGTC TTGGGGACCT | 180 | |
| TTGTCTTCTG TGTAAATGGT ACTAGAGAAA ACACCTATNT TATGAGTCAA TCTAGTTNGT | 240 | |
| TTTATTCGAC ATGAAGGAAA TTTCCAGATN ACAAACACTNA CAAACTCTCC CTKGACKARG | 300 | |
| GGGGACAAAG AAAAGCAAAA CTGAMCATAA RAAACAATWA CCTGGTGAGA ARTTGCATAA | 360 | |
| ACAGAAATWR GGTAGTATAT TGAARNACAG CATCATTAAA RMGTTWTKTT WTTCTCCCTT | 420 | |
| GCAAAAAACA TGTACNGACT TCCCGTTGAG TAATGCCAAG TTGTTTTTTT TATNATAAAA | 480 | |
| CTTGCCCTTC ATTACATGTT TNAAAGTGGT GTGGTGGGCC AAAATATTGA AATGATGGAA | 540 | |
| CTGACTGATA AAGCTGTACA AATAAGCAGT GTGCCTAACA AGCAACACAG TAATGTTGAC | 600 | |
| ATGCTTAATT CACAAATGCT AATTTCATTA TAAATGTTTG CTAAAATACA CTTTGAACTA | 660 | |
| TTTTTCTGTN TTCCCAGAGC TGAGATNTTA GATTTTATGT AGTATNAAGT GAAAAANTAC | 720 | |
| GAAAATAATA ACATTGAAGA AAAANANAAA AAANAAAAAA A | 761 | |

(2) INFORMATION FOR SEQ ID NO: 189:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (xi) SEQUENCE DESCRIPTION: SEQ ID NO: 189:

| | | |
|---|---|---|
| TTTTTTTTTT TTTGCCGATN CTACTATTTT ATTGCAGGAN GTGGGGTGT ATGCACCGCA | 60 | |
| CACCGGGGCT ATNAGAAGCA AGAAGGAAGG AGGGAGGGCA CAGCCCCTTG CTGAGCAACA | 120 | |
| AAGCCGCCTG CTGCCTTCTC TGTCTGTCTC CTGGTGCAGG CACATGGGGA GACCTTCCCC | 180 | |
| AAGGCAGGGG CCACCAGTCC AGGGGTGGGA ATACAGGGGG TGGGANGTGT GCATAAGAAG | 240 | |
| TGATAGGCAC AGGCCACCCG GTACAGACCC CTCGGCTCCT GACAGGTNGA TTTCGACCAG | 300 | |
| GTCATTGTGC CCTGCCCAGG CACAGCGTAN ATCTGGAAAA GACAGAATGC TTTCCTTTTC | 360 | |
| AAATTTGGCT NGTCATNGAA NGGGCANTTT TCCAANTTNG GCTNGGTCTT GGTACNCTTG | 420 | |
| GTTCGGCCCA GCTCCNCGTC CAAAAANTAT TCACCCNNCT CCNAATTGCT TGCNGGNCCC | 480 | |
| CC | 482 | |

(2) INFORMATION FOR SEQ ID NO: 190:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (xi) SEQUENCE DESCRIPTION: SEQ ID NO: 190:

| | | | | | |
|---|---|---|---|---|---|
| TTTTTTTTTT | TTTTAAAACA | GTTTTTCACA | ACAAAATTTA | TTAGAAGAAT | AGTGGTTTTG | 60 |
| AAAACTCTCG | CATCCAGTGA | GAACTACCAT | ACACCACATT | ACAGCTNGGA | ATGTNCTCCA | 120 |
| AATGTCTGGT | CAAATGATAC | AATGGAACCA | TTCAATCTTA | CACATGCACG | AAAGAACAAG | 180 |
| CGCTTTTGAC | ATACAATGCA | CAAAAAAAAA | AGGGGGGGGG | GACCACATGG | ATTAAAATTT | 240 |
| TAAGTACTCA | TCACATACAT | TAAGACACAG | TTCTAGTCCA | GTCNAAAATC | AGAACTGCNT | 300 |
| TGAAAAATTT | CATGTATGCA | ATCCAACCAA | AGAACTTNAT | TGGTGATCAT | GANTNCTCTA | 360 |
| CTACATCNAC | CTTGATCATT | GCCAGGAACN | AAAAGTTNAA | ANCACNCNGT | ACAAAAANAA | 420 |
| TCTGTAATTN | ANTTCAACCT | CCGTACNGAA | AAATNTTNNT | TATACACTCC | C | 471 |

(2) INFORMATION FOR SEQ ID NO: 191:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (xi) SEQUENCE DESCRIPTION: SEQ ID NO: 191:

| | | | | | |
|---|---|---|---|---|---|
| GAGGGATTGA | AGGTCTGTTC | TASTGTCGGM | CTGTTCAGCC | ACCAACTCTA | ACAAGTTGCT | 60 |
| GTCTTCCACT | CACTGTCTGT | AAGCTTTTTA | ACCCAGACWG | TATCTTCATA | AATAGAACAA | 120 |
| ATTCTTCACC | AGTCACATCT | TCTAGGACCT | TTTTGGATTC | AGTTAGTATA | AGCTCTTCCA | 180 |
| CTTCCTTTGT | TAAGACTTCA | TCTGGTAAAG | TCTTAAGTTT | TGTAGAAAGG | AATTYAATTG | 240 |
| CTCGTTCTCT | AACAATGTCC | TCTCCTTGAA | GTATTTGGCT | GAACAACCCA | CCTAAAGTCC | 300 |
| CTTTGTGCAT | CCATTTTAAA | TATACTTAAT | AGGGCATTGK | TNCACTAGGT | TAAATTCTGC | 360 |
| AAGAGTCATC | TGTCTGCAAA | AGTTGCGTTA | GTATATCTGC | CA | | 402 |

(2) INFORMATION FOR SEQ ID NO: 192:

(i) SEQUENCE CHARACTERISTICS:
        (A) LENGTH: 601 base pairs
        (B) TYPE: nucleic acid
        (C) STRANDEDNESS: single
        (D) TOPOLOGY: linear (xi) SEQUENCE DESCRIPTION: SEQ ID NO: 192:

| | | | | | |
|---|---|---|---|---|---|
| GAGCTCGGAT | CCAATAATCT | TTGTCTGAGG | GCAGCACACA | TATNCAGTGC | CATGGNAACT | 60 |
| GGTCTACCCC | ACATGGGAGC | AGCATGCCGT | AGNTATATAA | GGTCATTCCC | TGAGTCAGAC | 120 |
| ATGCYTYTTT | GAYTACCGTG | TGCCAAGTGC | TGGTGATTCT | YAACACACYT | CCATCCCGYT | 180 |
| CTTTTGTGGA | AAAACTGGCA | CTTKTCTGGA | ACTAGCARGA | CATCACTTAC | AAATTCACCC | 240 |
| ACGAGACACT | TGAAAGGTGT | AACAAAGCGA | YTCTTGCATT | GCTTTTTGTC | CCTCCGGCAC | 300 |
| CAGTTGTCAA | TACTAACCCG | CTGGTTTGCC | TCCATCACAT | TTGTGATCTG | TAGCTCTGGA | 360 |
| TACATCTCCT | GACAGTACTG | AAGAACTTCT | TCTTTTGTTT | CAAAAGCARC | TCTTGGTGCC | 420 |
| TGTTGGATCA | GGTTCCCATT | TCCCAGTCYG | AATGTTCACA | TGGCATATTT | WACTTCCCAC | 480 |
| AAAACATTGC | GATTTGAGGC | TCAGCAACAG | CAAATCCTGT | TCCGGCATTG | GCTGCAAGAG | 540 |
| CCTCGATGTA | GCCGGCCAGC | GCCAAGGCAG | GCGCCGTGAG | CCCCACCAGC | AGCAGAAGCA | 600 |

| | |
|---|---:|
| G | 601 |

(2) INFORMATION FOR SEQ ID NO: 193:

(i) SEQUENCE CHARACTERISTICS:
        (A) LENGTH: 608 base pairs
        (B) TYPE: nucleic acid
        (C) STRANDEDNESS: single
        (D) TOPOLOGY: linear (xi) SEQUENCE DESCRIPTION: SEQ ID NO: 193:

| | |
|---|---:|
| ATACAGCCCA NATCCCACCA CGAAGATGCG CTTGTTGACT GAGAACCTGA TGCGGTCACT | 60 |
| GGTCCCGCTG TAGCCCCAGC GACTCTCCAC CTGCTGGAAG CGGTTGATGC TGCACTCYTT | 120 |
| CCCAACGCAG GCAGMAGCGG GSCCGGTCAA TGAACTCCAY TCGTGGCTTG GGGTKGACGG | 180 |
| TKAAGTGCAG GAAGAGGCTG ACCACCTCGC GGTCCACCAG GATGCCCGAC TGTGCGGGAC | 240 |
| CTGCAGCGAA ACTCCTCGAT GGTCATGAGC GGGAAGCGAA TGAGGCCCAG GGCCTTGCCC | 300 |
| AGAACCTTCC GCCTGTTCTC TGGCGTCACC TGCAGCTGCT GCCGCTGACA CTCGGCCTCG | 360 |
| GACCAGCGGA CAAACGGCRT TGAACAGCCG CACCTCACGG ATGCCCAGTG TGTCGCGCTC | 420 |
| CAGGAMMGSC ACCAGCGTGT CCAGGTCAAT GTCGGTGAAG CCCTCCGCGG GTRATGGCGT | 480 |
| CTGCAGTGTT TTTGTCGATG TTCTCCAGGC ACAGGCTGGC CAGCTGCGGT TCATCGAAGA | 540 |
| GTCGCGCCTG CGTGAGCAGC ATGAAGGCGT TGTCGGCTCG CAGTTCTTCT TCAGGAACTC | 600 |
| CACGCAAT | 608 |

(2) INFORMATION FOR SEQ ID NO: 194:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (xi) SEQUENCE DESCRIPTION: SEQ ID NO: 194:

| | |
|---|---:|
| GAACGGCTGG ACCTTGCCTC GCATTGTGCT TGCTGGCAGG GAATACCTTG GCAAGCAGYT | 60 |
| CCAGTCCGAG CAGCCCCAGA CCGCTGCCGC CCGAAGCTAA GCCTGCCTCT GGCCTTCCCC | 120 |
| TCCGCCTCAA TGCAGAACCA GTAGTGGGAG CACTGTGTTT AGAGTTAAGA GTGAACACTG | 180 |
| TTTGATTTTA CTTGGGAATT TCCTCTGTTA TATAGCTTTT CCCAATGCTA ATTTCCAAAC | 240 |
| AACAACAACA AAATAACATG TTTGCCTGTT AAGTTGTATA AAAGTAGGTG ATTCTGTATT | 300 |
| TAAAGAAAAT ATTACTGTTA CATATACTGC TTGCAATTTC TGTATTTATT GKTNCTSTGG | 360 |
| AAATAAATAT AGTTATTAAA GGTTGTCANT CC | 392 |

(2) INFORMATION FOR SEQ ID NO: 195:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (xi) SEQUENCE DESCRIPTION: SEQ ID NO: 195:

| | |
|---|---:|
| CCSTTKGAGG GGTKAGGKYC CAGTTYCCGA GTGGAAGAAA CAGGCCAGGA GAAGTGCGTG | 60 |
| CCGAGCTGAG GCAGATGTTC CCACAGTGAC CCCCAGAGCC STGGGSTATA GTYTCTGACC | 120 |
| CCTCNCAAGG AAAGACCACS TTCTGGGGAC ATGGGCTGGA GGGCAGGACC TAGAGGCACC | 180 |
| AAGGGAAGGC CCCATTCCGG GGSTGTTCCC CGAGGAGGAA GGGAAGGGGC TCTGTGTGCC | 240 |

```
CCCCASGAGG AAGAGGCCCT GAGTCCTGGG ATCAGACACC CCTTCACGTG TATCCCCACA      300

CAAATGCAAG CTCACCAAGG TCCCCTCTCA GTCCCCTTCC STACACCCTG AMCGGCCACT      360

GSCSCACACC CACCCAGAGC ACGCCACCCG CCATGGGGAR TGTGCTCAAG GARTCGCNGG      420

GCARCGTGGA CATCTNGTCC CAGAAGGGGG CAGAATCTCC AATAGANGGA CTGARCMSTT      480

GCTNANAAAA AAAAANAAAA AA                                              502

(2) INFORMATION FOR SEQ ID NO: 196:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (xi) SEQUENCE DESCRIPTION: SEQ ID NO: 196:

GGTTACTTGG TTTCATTGCC ACCACTTAGT GGATGTCATT TAGAACCATT TTGTCTGCTC       60

CCTCTGGAAG CCTTGCGCAG AGCGGACTTT GTAATTGTTG GAGAATAACT GCTGAATTTT      120

WAGCTGTTTK GAGTTGATTS GCACCACTGC ACCCACAACT TCAATATGAA AACYAWTTGA      180

ACTWATTTAT TATCTTGTGA AAAGTATAAC AATGAAAATT TTGTTCATAC TGTATTKATC      240

AAGTATGATG AAAAGCAAWA GATATATATT CTTTTATTAT GTTAAATTAT GATTGCCATT      300

ATTAATCGGC AAAATGTGGA GTGTATGTTC TTTTCACAGT AATATATGCC TTTTGTAACT      360

TCACTTGGTT ATTTTATTGT AAATGARTTA CAAAATTCTT AATTTAAGAR AATGGTATGT      420

WATATTTATT TCATTAATTT CTTTCCTKGT TTACGTWAAT TTGAAAAGA WTGCATGATT       480

TCTTGACAGA AATCGATCTT GATGCTGTGG AAGTAGTTTG ACCCACATCC CTATGAGTTT      540

TTCTTAGAAT GTATAAAGGT TGTAGCCCAT CNAACTTCAA AGAAAAAAAT GACCACATAC      600

TTTGCAATCA GGCTGAAATG TGGCATGCTN TTCTAATTCC AACTTTATAA ACTAGCAAAN      660

AAGTG                                                                  665

(2) INFORMATION FOR SEQ ID NO: 197:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (xi) SEQUENCE DESCRIPTION: SEQ ID NO: 197:

TTTTNTTTTT TTTTTTTTGC AGGAAGGATT CCATTTATTG TGGATGCATT TTCACAATAT       60

ATGTTTATTG GAGCGATCCA TTATCAGTGA AAAGTATCAA GTGTTTATAA NATTTTTAGG      120

AAGGCAGATT CACAGAACAT GCTNGTCNGC TTGCAGTTTT ACCTCGTANA GATNACAGAG      180

AATTATAGTC NAACCAGTAA ACNAGGAATT TACTTTTCAA AAGATTAAAT CCAAACTGAA      240

CAAAATTCTA CCCTGAAACT TACTCCATCC AAATATTGGA ATAANAGTCA GCAGTGATAC      300

ATTCTCTTCT GAACTTTAGA TTTTCTAGAA AAATATGTAA TAGTGATCAG GAAGAGCTCT      360

TGTTCAAAAG TACAACNAAG CAATGTTCCC TTACCATAGG CCTTAATTCA AACTTTGATC      420

CATTTCACTC CCATCACGGG AGTCAATGCT ACCTGGGACA CTTGTATTTT GTTCATNCTG      480

ANCNTGGCTT AA                                                          492

(2) INFORMATION FOR SEQ ID NO: 198:

(i) SEQUENCE CHARACTERISTICS:
```

(A) LENGTH: 478 base pairs
        (B) TYPE: nucleic acid
        (C) STRANDEDNESS: single
        (D) TOPOLOGY: linear (xi) SEQUENCE DESCRIPTION: SEQ ID NO: 198:

TTTNTTTTGN ATTTCANTCT GTANNAANTA TTTTCATTAT GTTTATTANA AAAATATNAA      60

TGTNTCCACN ACAAATCATN TTACNTNAGT AAGAGGCCAN CTACATTGTA CAACATACAC     120

TGAGTATATT TTGAAAAGGA CAAGTTTAAA GTANACNCAT ATTGCCGANC ATANCACATT     180

TATACATGGC TTGATTGATA TTTAGCACAG CANAAACTGA GTGAGTTACC AGAAANAAAT     240

NATATATGTC AATCNGATTT AAGATACAAA ACAGATCCTA TGGTACATAN CATCNTGTAG     300

GAGTTGTGGC TTTATGTTTA CTGAAAGTCA ATGCAGTTCC TGTACAAAGA GATGGCCGTA     360

AGCATTCTAG TACCTCTACT CCATGGTTAA GAATCGTACA CTTATGTTTA CATATGTNCA     420

GGGTAAGAAT TGTGTTAAGT NAANTTATGG AGAGGTCCAN GAGAAAAATT TGATNCAA      478

(2) INFORMATION FOR SEQ ID NO: 199:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (xi) SEQUENCE DESCRIPTION: SEQ ID NO: 199:

AGTGACTTGT CCTCCAACAA AACCCCTTGA TCAAGTTTGT GGCACTGACA ATCAGACCTA      60

TGCTAGTTCC TGTCATCTAT TCGCTACTAA ATGCAGACTG GAGGGACCA AAAAGGGGCA     120

TCAACTCCAG CTGGATTATT TTGGAGCCTG CAAATCTATT CCTACTTGTA CGGACTTTGA     180

AGTGATTCAG TTTCCTCTAC GGATGAGAGA CTGGCTCAAG AATATCCTCA TGCAGCTTTA     240

TGAAGCCNAC TCTGAACACG CTGGTTATCT NAGATGAGAA NCAGAGAAAT AAAGTCNAGA     300

AAATTTACCT GGANGAAAAG AGGCTTTNGG CTGGGGACCA TCCCATTGAA CCTTCTCTTA     360

ANGGACTTTA AGAANAAACT ACCACATGTN TGTNGTATCC TGGTGCCNGG CCGTTTANTG     420

AACNTNGACN NCACCCTTNT GGAATANANT CTTGACNGCN TCCTGAACTT GCTCCTCTGC     480

GA                                                                  482

(2) INFORMATION FOR SEQ ID NO: 200:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (xi) SEQUENCE DESCRIPTION: SEQ ID NO: 200:

CGGCCGCAAG TGCAACTCCA GCTGGGGCCG TGCGGACGAA GATTCTGCCA GCAGTTGGTC      60

CGACTGCGAC GACGGCGGCG GCGACAGTCG CAGGTGCAGC GCGGGCGCCT GGGGTCTTGC     120

AAGGCTGAGC TGACGCCGCA GAGGTCGTGT CACGTCCCAC GACCTTGACG CCGTCGGGGA     180

CAGCCGGAAC AGAGCCCGGT GAANGCGGGA GGCCTCGGGG AGCCCCTCGG GAAGGGCGGC     240

CCGAGAGATA CGCAGGTGCA GGTGGCCGCC                                    270

(2) INFORMATION FOR SEQ ID NO: 201:

(i) SEQUENCE CHARACTERISTICS:
        (A) LENGTH: 419 base pairs
        (B) TYPE: nucleic acid (C) STRANDEDNESS: single
        (D) TOPOLOGY: linear (xi) SEQUENCE DESCRIPTION: SEQ ID NO: 201:

TTTTTTTTTT TTTTGGAATC TACTGCGAGC ACAGCAGGTC AGCAACAAGT TTATTTTGCA         60

GCTAGCAAGG TAACAGGGTA GGGCATGGTT ACATGTTCAG GTCAACTTCC TTTGTCGTGG        120

TTGATTGGTT TGTCTTTATG GGGGCGGGGT GGGGTAGGGG AAANCGAAGC ANAANTAACA        180

TGGAGTGGGT GCACCCTCCC TGTAGAACCT GGTTACNAAA GCTTGGGGCA GTTCACCTGG        240

TCTGTGACCG TCATTTTCTT GACATCAATG TTATTAGAAG TCAGGATATC TTTTAGAGAG        300

TCCACTGTNT CTGGAGGGAG ATTAGGGTTT CTTGCCAANA TCCAANCAAA ATCCACNTGA        360

AAAAGTTGGA TGATNCANGT ACNGAATACC GANGGCATAN TTCTCATANT CGGTGGCCA        419

(2) INFORMATION FOR SEQ ID NO: 202:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (xi) SEQUENCE DESCRIPTION: SEQ ID NO: 202:

TTTNTTTTTT TTTTTTTTTT TTTTTTTTTT TTTTTTTTTT TTTTTTTTTT TTTTTTTTTT         60

TGGCACTTAA TCCATTTTTA TTTCAAAATG TCTACAAANT TTNAATNCNC CATTATACNG        120

GTNATTTTNC AAAATCTAAA NNTTATTCAA ATNTNAGCCA AANTCCTTAC NCAAATNNAA        180

TACNCNCAAA AATCAAAAAT ATACNTNTCT TTCAGCAAAC TTNGTTACAT AAATTAAAAA        240

AATATATACG GCTGGTGTTT TCAAAGTACA ATTATCTTAA CACTGCAAAC ATNTTTNNAA        300

GGAACTAAAA TAAAAAAAAA CACTNCCGCA AAGGTTAAAG GGAACAACAA ATTCNTTTTA        360

CAACANCNNC NATTATAAAA ATCATATCTC AAATCTTAGG GGAATATATA CTTCACACNG        420

GGATCTTAAC TTTTACTNCA CTTTGTTTAT TTTTTTANAA CCATTGTNTT GGGCCCAACA        480

CAATGGNAAT NCCNCCNCNC TGGACTAGT                                          509

(2) INFORMATION FOR SEQ ID NO: 203:

(i) SEQUENCE CHARACTERISTICS:
        (A) LENGTH: 583 base pairs
        (B) TYPE: nucleic acid
        (C) STRANDEDNESS: single
        (D) TOPOLOGY: linear (xi) SEQUENCE DESCRIPTION: SEQ ID NO: 203:

TTTTTTTTTT TTTTTTTTGA CCCCCCTCTT ATAAAAAACA AGTTACCATT TTATTTTACT         60

TACACATATT TATTTTATAA TTGGTATTAG ATATTCAAAA GGCAGCTTTT AAAATCAAAC        120

TAAATGGAAA CTGCCTTAGA TACATAATTC TTAGGAATTA GCTTAAAATC TGCCTAAAGT        180

GAAAATCTTC TCTAGCTCTT TTGACTGTAA ATTTTGACT CTTGTAAAAC ATCCAAATTC        240

ATTTTTCTTG TCTTTAAAAT TATCTAATCT TTCCATTTTT TCCCTATTCC AAGTCAATTT        300

GCTTCTCTAG CCTCATTTCC TAGCTCTTAT CTACTATTAG TAAGTGGCTT TTTTCCTAAA        360

AGGGAAAACA GGAAGAGANA ATGGCACACA AAACAAACAT TTTATATTCA TATTTCTACC        420

TACGTTAATA AAATAGCATT TTGTGAAGCC AGCTCAAAAG AAGGCTTAGA TCCTTTTATG        480

TCCATTTTAG TCACTAAACG ATATCNAAAG TGCCAGAATG CAAAAGGTTT GTGAACATTT        540

ATTCAAAAGC TAATATAAGA TATTTCACAT ACTCATCTTT CTG                          583

(2) INFORMATION FOR SEQ ID NO: 204:

(i) SEQUENCE CHARACTERISTICS:
        (A) LENGTH: 589 base pairs
        (B) TYPE: nucleic acid
        (C) STRANDEDNESS: single
        (D) TOPOLOGY: linear (xi) SEQUENCE DESCRIPTION: SEQ ID NO: 204:

```
TTTTTTTTNT TTTTTTTTTT TTTTTTNCTC TTCTTTTTTT TTGANAATGA GGATCGAGTT      60
TTTCACTCTC TAGATAGGGC ATGAAGAAAA CTCATCTTTC CAGCTTTAAA ATAACAATCA     120
AATCTCTTAT GCTATATCAT ATTTTAAGTT AAACTAATGA GTCACTGGCT TATCTTCTCC     180
TGAAGGAAAT CTGTTCATTC TTCTCATTCA TATAGTTATA TCAAGTACTA CCTTGCATAT     240
TGAGAGGTTT TTCTTCTCTA TTTACACATA TATTTCCATG TGAATTTGTA TCAAACCTTT     300
ATTTTCATGC AAACTAGAAA ATAATGTNTT CTTTTGCATA AGAGAAGAGA ACAATATNAG     360
CATTACAAAA CTGCTCAAAT TGTTTGTTAA GNTTATCCAT TATAATTAGT TNGGCAGGAG     420
CTAATACAAA TCACATTTAC NGACNAGCAA TAATAAAACT GAAGTACCAG TTAAATATCC     480
AAAATAATTA AGGAACATT TTTAGCCTGG GTATAATTAG CTAATTCACT TTACAAGCAT     540
TTATTNAGAA TGAATTCACA TGTTATTATT CCNTAGCCCA ACACAATGG               589
```

(2) INFORMATION FOR SEQ ID NO: 205:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (xi) SEQUENCE DESCRIPTION: SEQ ID NO: 205:

```
TTTTTNTTTT TTTTTTCAGT AATAATCAGA ACAATATTTA TTTTTATATT TAAAATTCAT      60
AGAAAAGTGC CTTACATTTA ATAAAAGTTT GTTTCTCAAA GTGATCAGAG GAATTAGATA     120
TNGTCTTGAA CACCAATATT AATTTGAGGA AAATACACCA AAATACATTA AGTAAATTAT     180
TTAAGATCAT AGAGCTTGTA AGTGAAAAGA TAAAATTTGA CCTCAGAAAC TCTGAGCATT     240
AAAAATCCAC TATTAGCAAA TAAATTACTA TGGACTTCTT GCTTTAATTT TGTGATGAAT     300
ATGGGGTGTC ACTGGTAAAC CAACACATTC TGAAGGATAC ATTACTTAGT GATAGATTCT     360
TATGTACTTT GCTANATNAC GTGGATATGA GTTGACAAGT TTCTCTTTCT TCAATCTTTT     420
AAGGGGCNGA NGAAATGAGG AAGAAAAGAA AAGGATTACG CATACTGTTC TTTCTATNGG     480
AAGGATTAGA TATGTTTCCT TTGCCAATAT TAAAAAAATA ATAATGTTTA CTACTAGTGA     540
AACCC                                                               545
```

(2) INFORMATION FOR SEQ ID NO: 206:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 206:

```
TTTTTTTTTT TTTTTTAGTC AAGTTTCTNA TTTTTATTAT AATTAAAGTC TTGGTCATTT      60
CATTTATTAG CTCTGCAACT TACATATTTA AATTAAAGAA ACGTTNTTAG ACAACTGTNA     120
```

-continued

| | | |
|---|---|---|
| CAATTTATAA ATGTAAGGTG CCATTATTGA GTANATATAT TCCTCCAAGA GTGGATGTGT | 180 |
| CCCTTCTCCC ACCAACTAAT GAANCAGCAA CATTAGTTTA ATTTTATTAG TAGATNATAC | 240 |
| ACTGCTGCAA ACGCTAATTC TCTTCTCCAT CCCCATGTNG ATATTGTGTA TATGTGTGAG | 300 |
| TTGGTNAGAA TGCATCANCA ATCTNACAAT CAACAGCAAG ATGAAGCTAG GCNTGGGCTT | 360 |
| TCGGTGAAAA TAGACTGTGT CTGTCTGAAT CAAATGATCT GACCTATCCT CGGTGGCAAG | 420 |
| AACTCTTCGA ACCGCTTCCT CAAAGGCNGC TGCCACATTT GTGGCNTCTN TTGCACTTGT | 480 |
| TTCAAAA | 487 |

(2) INFORMATION FOR SEQ ID NO: 207:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 207:

| | | |
|---|---|---|
| TGAATTGGCT AAAAGACTGC ATTTTTANAA CTAGCAACTC TTATTTCTTT CCTTTAAAAA | 60 |
| TACATAGCAT TAAATCCCAA ATCCTATTTA AAGACCTGAC AGCTTGAGAA GGTCACTACT | 120 |
| GCATTTATAG GACCTTCTGG TGGTTCTGCT GTTACNTTTG AANTCTGACA ATCCTTGANA | 180 |
| ATCTTTGCAT GCAGAGGAGG TAAAAGGTAT TGGATTTTCA CAGAGGAANA ACACAGCGCA | 240 |
| GAAATGAAGG GGCCAGGCTT ACTGAGCTTG TCCACTGGAG GGCTCATGGG TGGGACATGG | 300 |
| AAAAGAAGGC AGCCTAGGCC CTGGGGAGCC CA | 332 |

(2) INFORMATION FOR SEQ ID NO: 208:

(i) SEQUENCE CHARACTERISTICS:
        (A) LENGTH: 524 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 208:

| | | |
|---|---|---|
| AGGGCGTGGT GCGGAGGGCG TTACTGTTTT GTCTCAGTAA CAATAAATAC AAAAAGACTG | 60 |
| GTTGTGTTCC GGCCCCATCC AACCACGAAG TTGATTTCTC TTGTGTGCAG AGTGACTGAT | 120 |
| TTTAAAGGAC ATGGAGCTTG TCACAATGTC ACAATGTCAC AGTGTGAAGG GCACACTCAC | 180 |
| TCCCGCGTGA TTCACATTTA GCAACCAACA ATAGCTCATG AGTCCATACT TGTAAATACT | 240 |
| TTTGGCAGAA TACTTNTTGA AACTTGCAGA TGATAACTAA GATCCAAGAT ATTTCCCAAA | 300 |
| GTAAATAGAA GTGGGTCATA ATATTAATTA CCTGTTCACA TCAGCTTCCA TTTACAAGTC | 360 |
| ATGAGCCCAG ACACTGACAT CAAACTAAGC CCACTTAGAC TCCTCACCAC CAGTCTGTCC | 420 |
| TGTCATCAGA CAGGAGGCTG TCACCTTGAC CAAATTCTCA CCAGTCAATC ATCTATCCAA | 480 |
| AAACCATTAC CTGATCCACT TCCGGTAATG CACCACCTTG GTGA | 524 |

(2) INFORMATION FOR SEQ ID NO: 209:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 209:

| | |
|---|---|
| GGGTGAGGAA ATCCAGAGTT GCCATGGAGA AAATTCCAGT GTCAGCATTC TTGCTCCTTG | 60 |
| TGGCCCTCTC CTACACTCTG GCCAGAGATA CCACAGTCAA ACCTGGAGCC AAAAAGGACA | 120 |
| CAAAGGACTC TCGACCCAAA CTGCCCCAGA CCCTCTCCA | 159 |

(2) INFORMATION FOR SEQ ID NO: 210:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 210:

| | |
|---|---|
| ACTCCCTGGC AGACAAAGGC AGAGGAGAGA GCTCTGTTAG TTCTGTGTTG TTGAACTGCC | 60 |
| ACTGAATTTC TTTCCACTTG GACTATTACA TGCCANTTGA GGGACTAATG GAAAAACGTA | 120 |
| TGGGGAGATT TTANCCAATT TANGTNTGTA AATGGGGAGA CTGGGGCAGG CGGGAGAGAT | 180 |
| TTGCAGGGTG NAAATGGGAN GGCTGGTTTG TTANATGAAC AGGGACATAG GAGGTAGGCA | 240 |
| CCAGGATGCT AAATCA | 256 |

(2) INFORMATION FOR SEQ ID NO: 211:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 211:

| | |
|---|---|
| ACATTGTTTT TTTGAGATAA AGCATTGAGA GAGCTCTCCT TAACGTGACA CAATGGAAGG | 60 |
| ACTGGAACAC ATACCCACAT CTTTGTTCTG AGGGATAATT TTCTGATAAA GTCTTGCTGT | 120 |
| ATATTCAAGC ACATATGTTA TATATTATTC AGTTCCATGT TTATAGCCTA GTTAAGGAGA | 180 |
| GGGGAGATAC ATTCNGAAAG AGGACTGAAA GAAATACTCA AGTNGGAAAA CAGAAAAAGA | 240 |
| AAAAAAGGAG CAAATGAGAA GCCT | 264 |

(2) INFORMATION FOR SEQ ID NO: 212:

(i) SEQUENCE CHARACTERISTICS:
        (A) LENGTH: 328 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 212:

| | |
|---|---|
| ACCCAAAAAT CCAATGCTGA ATATTTGGCT TCATTATTCC CANATTCTTT GATTGTCAAA | 60 |
| GGATTTAATG TTGTCTCAGC TTGGGCACTT CAGTTAGGAC CTAAGGATGC CAGCCGGCAG | 120 |
| GTTTATATAT GCAGCAACAA TATTCAAGCG CGACAACAGG TTATTGAACT TGCCCGCCAG | 180 |
| TTNAATTTCA TTCCCATTGA CTTGGGATCC TTATCATCAG CCAGAGAGAT TGAAAATTTA | 240 |
| CCCCTACNAC TCTTTACTCT CTGGANAGGG CCAGTGGTGG TAGCTATAAG CTTGGCCACA | 300 |

```
TTTTTTTTTC CTTTATTCCT TTGTCAGA                                          328

(2) INFORMATION FOR SEQ ID NO: 213:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 213:

ACTTATGAGC AGAGCGACAT ATCCNAGTGT AGACTGAATA AAACTGAATT CTCTCCAGTT        60

TAAAGCATTG CTCACTGAAG GGATAGAAGT GACTGCCAGG AGGGAAAGTA AGCCAAGGCT       120

CATTATGCCA AAGGANATAT ACATTTCAAT TCTCCAAACT TCTTCCTCAT TCCAAGAGTT       180

TTCAATATTT GCATGAACCT GCTGATAANC CATGTTAANA AACAAATATC TCTCTNACCT       240

TCTCATCGGT                                                             250

(2) INFORMATION FOR SEQ ID NO: 214:

(i) SEQUENCE CHARACTERISTICS:
        (A) LENGTH: 444 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 214:

ACCCAGAATC CAATGCTGAA TATTTGGCTT CATTATTCCC AGATTCTTTG ATTGTCAAAG        60

GATTTAATGT TGTCTCAGCT TGGGCACTTC AGTTAGGACC TAAGGATGCC AGCCGGCAGG       120

TTTATATATG CAGCAACAAT ATTCAAGCGC GACAACAGGT TATTGAACTT GCCCGCCAGT       180

TGAATTTCAT TCCCATTGAC TTGGGATCCT TATCATCAGC CANAGAGATT GAAAATTTAC       240

CCCTACGACT CTTTACTCTC TGGAGAGGGC CAGTGGTGGT AGCTATAAGC TTGGCCACAT       300

TTTTTTTTCC TTTATTCCTT TGTCAGAGAT GCGATTCATC CATATGCTAN AAACCAACAG       360

AGTGACTTTT ACAAAATTCC TATAGANATT GTGAATAAAA CCTTACCTAT AGTTGCCATT       420

ACTTTGCTCT CCCTAATATA CCTC                                             444

(2) INFORMATION FOR SEQ ID NO: 215:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 215:

ACTTATGAGC AGAGCGACAT ATCCAAGTGT ANACTGAATA AAACTGAATT CTCTCCAGTT        60

TAAAGCATTG CTCACTGAAG GGATAGAAGT GACTGCCAGG AGGGAAAGTA AGCCAAGGCT       120

CATTATGCCA AAGGANATAT ACATTTCAAT TCTCCAAACT TCTTCCTCAT TCCAAGAGTT       180

TTCAATATTT GCATGAACCT GCTGATAAGC CATGTTGAGA AACAAATATC TCTCTGACCT       240

TCTCATCGGT AAGCAGAGGC TGTAGGCAAC ATGGACCATA GCGAANAAAA AACTTAGTAA       300

TCCAAGCTGT TTTCTACACT GTAACCAGGT TTCCAACCAA GGTGGAAATC TCCTATACTT       360
```

```
GGTGCC                                                                    366

(2) INFORMATION FOR SEQ ID NO: 216:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 216:

CTGTATAAAC AGAACTCCAC TGCANGAGGG AGGGCCGGGC CAGGAGAATC TCCGCTTGTC    60

CAAGACAGGG GCCTAAGGAG GGTCTCCACA CTGCTNNTAA GGGCTNTTNC ATTTTTTAT    120

TAATAAAAAG TNNAAAAGGC CTCTTCTCAA CTTTTTTCCC TTNGGCTGGA AAATTTAAAA   180

ATCAAAAATT TCCTNAAGTT NTCAAGCTAT CATATATACT NTATCCTGAA AAAGCAACAT   240

AATTCTTCCT TCCCTCCTTT                                                260

(2) INFORMATION FOR SEQ ID NO: 217:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 217:

ACCTACGTGG GTAAGTTTAN AAATGTTATA ATTTCAGGAA NAGGAACGCA TATAATTGTA    60

TCTTGCCTAT AATTTTCTAT TTTAATAAGG AAATAGCAAA TTGGGGTGGG GGGAATGTAG   120

GGCATTCTAC AGTTTGAGCA AAATGCAATT AAATGTGGAA GGACAGCACT GAAAAATTTT   180

ATGAATAATC TGTATGATTA TATGTCTCTA GAGTAGATTT ATAATTAGCC ACTTACCCTA   240

ATATCCTTCA TGCTTGTAAA GT                                             262

(2) INFORMATION FOR SEQ ID NO: 218:

(i) SEQUENCE CHARACTERISTICS:
        (A) LENGTH: 205 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 218:

ACCAAGGTGG TGCATTACCG GAANTGGATC AANGACACCA TCGTGGCCAA CCCCTGAGCA    60

CCCCTATCAA CTCCCTTTTG TAGTAAACTT GGAACCTTGG AAATGACCAG GCCAAGACTC   120

AGGCCTCCCC AGTTCTACTG ACCTTTGTCC TTANGTNTNA NGTCCAGGGT TGCTAGGAAA   180

ANAAATCAGC AGACACAGGT GTAAA                                          205

(2) INFORMATION FOR SEQ ID NO: 219:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO: 219:

TACTGTTTTG TCTCAGTAAC AATAAATACA AAAAGACTGG TTGTGTTCCG GCCCCATCCA    60

ACCACGAAGT TGATTTCTCT TGTGTGCAGA GTGACTGATT TTAAAGGACA TGGA    114

(2) INFORMATION FOR SEQ ID NO: 220:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 220:

ACTAGCCAGC ACAAAAGGCA GGGTAGCCTG AATTGCTTTC TGCTCTTTAC ATTTCTTTTA    60

AAATAAGCAT TTAGTGCTCA GTCCCTACTG AGT    93

(2) INFORMATION FOR SEQ ID NO: 221:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 221:

ACTANGTGCA GGTGCGCACA AATATTTGTC GATATTCCCT TCATCTTGGA TTCCATGAGG    60

TCTTTTGCCC AGCCTGTGGC TCTACTGTAG TAAGTTTCTG CTGATGAGGA GCCAGNATGC    120

CCCCCACTAC CTTCCCTGAC GCTCCCCANA AATCACCCAA CCTCTGT    167

(2) INFORMATION FOR SEQ ID NO: 222:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 222:

AGGGCGTGGT GCGGAGGGCG GTACTGACCT CATTAGTAGG AGGATGCATT CTGGCACCCC    60

GTTCTTCACC TGTCCCCCAA TCCTTAAAAG GCCATACTGC ATAAAGTCAA CAACAGATAA    120

ATGTTTGCTG AATTAAAGGA TGGATGAAAA AAATTAATAA TGAATTTTTG CATAATCCAA    180

TTTTCTCTTT TATATTTCTA GAAGAAGTTT CTTTGAGCCT ATTAGATCCC GGGAATCTTT    240

TAGGTGAGCA TGATTAGAGA GCTTGTAGGT TGCTTTTACA TATATCTGGC ATATTTGAGT    300

CTCGTATCAA AACAATAGAT TGGTAAAGGT GGTATTATTG TATTGATAAG T    351

(2) INFORMATION FOR SEQ ID NO: 223:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (xi) SEQUENCE DESCRIPTION: SEQ ID NO: 223:

-continued

```
AAAACAAACA AACAAAAAAA ACAATTCTTC ATTCAGAAAA ATTATCTTAG GGACTGATAT        60

TGGTAATTAT GGTCAATTTA ATWRTRTTKT GGGGCATTTC CTTACATTGT CTTGACAAGA       120

TTAAAATGTC TGTGCCAAAA TTTTGTATTT TATTTGGAGA CTTCTTATCA AAAGTAATGC       180

TGCCAAAGGA AGTCTAAGGA ATTAGTAGTG TTCCCMTCAC TTGTTTGGAG TGTGCTATTC       240

TAAAAGATTT TGATTTCCTG GAATGACAAT TATATTTTAA CTTTGGTGGG GGAAANAGTT       300

ATAGGACCAC AGTCTTCACT TCTGATACTT GTAAATTAAT CTTTTATTGC ACTTGTTTTG       360

ACCATTAAGC TATATGTTTA AAA                                               383

(2) INFORMATION FOR SEQ ID NO: 224:

(i) SEQUENCE CHARACTERISTICS:
        (A) LENGTH: 320 base pairs
        (B) TYPE: nucleic acid
        (C) STRANDEDNESS: single
        (D) TOPOLOGY: linear (xi) SEQUENCE DESCRIPTION: SEQ ID NO: 224:

CCCCTGAAGG CTTCTTGTTA GAAAATAGTA CAGTTACAAC CAATAGGAAC AACAAAAAGA        60

AAAAGTTTGT GACATTGTAG TAGGGAGTGT GTACCCCTTA CTCCCCATCA AAAAAAAAAT       120

GGATACATGG TTAAAGGATA RAAGGGCAAT ATTTTATCAT ATGTTCTAAA AGAGAAGGAA       180

GAGAAAATAC TACTTTCTCR AAATGGAAGC CCTTAAAGGT GCTTTGATAC TGAAGGACAC       240

AAATGTGGCC GTCCATCCTC CTTTARAGTT GCATGACTTG GACACGGTAA CTGTTGCAGT       300

TTTARACTCM GCATTGTGAC                                                   320
```

COMPOUNDS FOR IMMUNOTHERAPY OF PROSTATE CANCER AND METHODS FOR THEIR USE

REFERENCE TO RELATED APPLICATIONS

This application is a continuation-in-part of U.S. patent application Ser. No. 09/020,956, filed Feb. 9, 1998, which is a continuation-in-part of U.S. patent application Ser. No. 08/904,804, now abandoned filed Aug. 1, 1997, which is a continuation-in-part of U.S. patent application Ser. No. 08/806,099, now abandoned filed Feb. 25, 1997.

TECHNICAL FIELD

The present invention relates generally to compositions and methods for the treatment of prostate cancer. The invention is more particularly related to polypeptides comprising at least a portion of a prostate protein and to DNA molecules encoding such polypeptides. Such polypeptides may be used in vaccines and pharmaceutical compositions for treatment of prostate cancer.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

Accordingly, there remains a need in the art for improved vaccines and treatment methods for prostate cancer.

SUMMARY OF THE INVENTION

The present invention provides compounds and methods for immunotherapy of prostate cancer. In one aspect, polypeptides are provided comprising at least an immunogenic portion of a prostate tumor protein or a variant of said protein that differs only in conservative substitutions and/or modifications, wherein the prostate tumor protein comprises an amino acid sequence encoded by a DNA molecule having a sequence selected from the group consisting of nucleotide sequences recited in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209–211, 220, 222–224, the complements of said nucleotide sequences and variants thereof.

In related aspects, DNA molecules encoding the above polypeptides are provided. In specific embodiments, such DNA molecules include sequences provided in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209–211, 220 and 222–224. The present invention further provides expression vectors comprising the above DNA molecules and host cells transformed or transfected with such expression vectors. In preferred embodiments, the host cells are selected from the group consisting of *E. coli,* yeast and mammalian cells.

In another aspect, the present invention provides fusion proteins comprising a first and a second inventive polypeptide or, alternatively, an inventive polypeptide and a known prostate antigen.

The present invention also provides pharmaceutical compositions comprising one or more of the above polypeptides, or a DNA molecule encoding such polypeptides, and a physiologically acceptable carrier, together with vaccines comprising one or more of such polypeptide or DNA molecules in combination with a non-specific immune response enhancer.

In related aspects, pharmaceutical compositions for the treatment of prostate cancer comprising one or more polypeptides and a physiologically acceptable carrier are provided, wherein the polypeptide comprises an immunogenic portion of a prostate tumor protein or of a variant of said protein that differs only in conservative substitutions and/or modifications, the prostate tumor protein being encoded by a DNA molecule having a sequence selected from the group consisting of nucleotide sequences recited in SEQ ID NO: 5–7, 30–40, 46, 53, 66–69, 71, 72, 75–78, 80, 82–86, 88, 89, 91, 94–96, 98–102, 105, 106 and 161–170, 179, 180, 182–187, 189, 190, 192, 195–197, 199–202, 205, 206, 208, 212–219, 221, the complements of said nucleotide sequences and variants thereof. The invention also provides vaccines for the treatment of prostate cancer comprising such polypeptides in combination with a non-specific immune response enhancer, together with pharmaceutical compositions and vaccines comprising one or more DNA molecules having a sequence provided in SEQ ID NO: 5–7, 30–40, 46, 53, 66–69, 71, 72, 75–78, 80, 82–86, 88, 89, 91, 94–96, 98–102, 105, 106 and 161–170, 179, 180, 182–187, 189, 190, 192, 195–197, 199–202, 205, 206, 208, 212–219 and 221. Pharmaceutical compositions and vaccines comprising one or more of the above fusion proteins are also provided.

In yet another aspect, methods are provided for inhibiting the development of prostate cancer in a patient, comprising administering an effective amount of at least one of the above pharmaceutical compositions and/or vaccines.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

As noted above, the present invention is generally directed to compositions and methods for the immunotherapy of prostate cancer. The inventive compositions are generally polypeptides that comprise at least a portion of a prostate tumor protein. Also included within the present invention are molecules (such as an antibody or fragment thereof) that bind to the inventive polypeptides. Such molecules are referred to herein as "binding agents."

In particular, the subject invention discloses polypeptides comprising at least a portion of a human prostate tumor protein, or a variant of such a protein that differs only in conservative substitutions and/or modifications, wherein the prostate tumor protein includes an amino acid sequence encoded by a DNA molecule having a sequence selected from the group consisting of nucleotide sequences recited in SEQ ID NO: 2, 3, 8–29, 41–45, 47–52, 54–65, 70, 73–74, 79, 81, 87, 90, 92, 93, 97, 103, 104, 107, 109–111, 115–160, 181, 188, 191, 193, 194, 198, 203, 204, and 207–224, the complements of said nucleotide sequences and variants thereof. As used herein, the term "polypeptide" encompasses amino acid chains of any length, including full length proteins, wherein the amino acid residues are linked by covalent peptide bonds. Thus, a polypeptide comprising a portion of one of the above prostate proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human prostate tumor protein is a portion that is capable of eliciting an immune response in a patient inflicted with prostate cancer and as such binds to antibodies present within sera from a prostate cancer patient. Immunogenic portions of the proteins described herein may thus be identified in antibody binding assays. Such assays may generally be performed using any of a variety of means known to those of ordinary skill in the art, as described, for example, in Harlow and Lane, *Antibodies: A Laboratory Manual,* Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of prostate cancer patients.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. For prostate tumor polypeptides with immunoreactive properties, variants may, alternatively, be identified by modifying the amino acid sequence of one of the above polypeptides, and evaluating the immunoreactivity of the modified polypeptide. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA,* 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. Such variant nucleotide sequences will generally hybridize to the recite nucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1 % SDS at 65° C.

"Polypeptides" as used herein also include combination, or fusion, polypeptides. A "combination polypeptide" is a polypeptide comprising at least one of the above immunogenic portions and one or more additional immunogenic prostate tumor-specific sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

The prostate tumor proteins of the present invention, and DNA molecules encoding such proteins, may be isolated from prostate tumor tissue using any of a variety of methods well known in the art. DNA sequences corresponding to a gene (of a portion thereof) encoding one of the inventive prostate tumor proteins may be isolated from a prostate tumor cDNA library using a subtraction technique as described in detail below. Examples of such DNA sequences are provided in SEQ ID NOS: 1–107, 109–111, 115–171, 173–175, 177 and 179–224. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol.,* 51:263, 1987; Erlich ed., *PCR Technology,* Stockton Press, N.Y., 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (*DNA,* 2:183, 1983).

The prostate tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, J. Am. Chem. Soc. 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known prostate antigen, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39–46, 1985; Murphy et al., Proc. Natl. Acad. Sci. USA 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Polypeptides of the present invention that comprise an immunogenic portion of a prostate tumor protein may generally be used for immunotherapy of prostate cancer, wherein the polypeptide stimulates the patient's own immune response to prostate tumor cells. In further aspects, the present invention provides methods for using one or more of the immunoreactive polypeptides encoded by a DNA molecule having a sequence provided in SEQ ID NOS: 1–107, 109–111, 115–171, 173–175, 177 and 179–224 (or fusion proteins comprising one or more such polypeptides and/or DNA encoding such polypeptides) for immunotherapy of prostate cancer in a patient. As used herein, a "patient" refers to any warm-blooded animal, preferably a human. A patient may be afflicted with a disease, or may be free of detectable disease. Accordingly, the above immunoreactive polypeptides (or fusion proteins or DNA molecules encoding such polypeptides) may be used to treat prostate cancer or to inhibit the development of prostate cancer. The polypeptides may be administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, such as an adjuvant, biodegradable microsphere (e.g., polylactic galactide) or a liposome (into which the polypeptide is incorporated). Pharmaceutical compositions and vaccines may also contain other epitopes of prostate tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against prostate tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of prostate cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides of the present invention may also, or alternatively, be used to generate binding agents, such as antibodies or fragments thereof, that are capable of detecting metastatic human prostate tumors. Binding agents of the present invention may generally be prepared using methods known to those of ordinary skill in the art, including the representative procedures described herein. Binding agents are capable of differentiating between patients with and without prostate cancer, using the representative assays described herein. In other words, antibodies or other binding agents raised against a prostate tumor protein, or a suitable portion thereof, will generate a signal indicating the presence of primary or metastatic prostate cancer in at least about 20% of patients afflicted with the disease, and will generate a negative signal indicating the absence of the disease in at least about 90% of individuals without primary or metastatic prostate cancer. Suitable portions of such prostate tumor proteins are portions that are able to generate a binding agent that indicates the presence of primary or metastatic prostate cancer in substantially all (i.e., at least about 80%, and preferably at least about 90%) of the patients for which prostate cancer would be indicated using the full length protein, and that indicate the absence of prostate cancer in substantially all of those samples that would be negative when tested with full length protein. The representative assays described below, such as the two-antibody sandwich assay, may generally be employed for evaluating the ability of a binding agent to detect metastatic human prostate tumors.

The ability of a polypeptide prepared as described herein to generate antibodies capable of detecting primary or metastatic human prostate tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic prostate cancer for the presence of a polypeptide that binds to the generated antibodies. Such test assays may be performed, for example, using a representative procedure described below. Polypeptides that generate antibodies capable of detecting at least 20% of primary or metastatic prostate tumors by such procedures are considered to be useful in assays for detecting primary or metastatic human prostate tumors. Polypeptide specific antibodies may be used alone or in combination to improve sensitivity.

Polypeptides capable of detecting primary or metastatic human prostate tumors may be used as markers for diagnosing prostate cancer or for monitoring disease progression in patients. In one embodiment, prostate cancer in a patient may be diagnosed by evaluating a biological sample obtained from the patient for the level of one or more of the above polypeptides, relative to a predetermined cut-off value. As used herein, suitable "biological samples" include blood, sera, urine and/or prostate secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual,* Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of prostate cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast, prostate cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual,* Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate prostate tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify prostate tumor-specific cDNA derived from a biological sample, wherein at least one of the oligonucleotide primers is specific for a DNA molecule encoding a prostate tumor protein of the present invention.

The presence of the amplified cDNA is then detected using techniques well known in the art, such as gel electrophoresis. Similarly, oligonucleotide probes specific for a DNA molecule encoding a prostate tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule having a sequence selected from SEQ ID NOS: 1–107, 109–111, 115–171, 173–175, 177 and 179–224. Preferably, oligonucleotide probes for use in the inventive diagnostic methods comprise at least about 15 contiguous oligonucleotides of a DNA molecule having a sequence provided in SEQ ID NOS: 1–107, 109–111, 115–171, 173–175, 177 and 179–224. Techniques for both PCR based assays and hybridization assays are well known in the art (see, for example, Mullis et al. Ibid; Ehrlich, Ibid). Primers or probes may thus be used to detect prostate tumor-specific sequences in biological samples, including blood, semen, prostate tissue and/or prostate tumor tissue.

The following Examples are offered by way of illustration and not by way of limitation.

EXAMPLES

Example 1

Isolation and Characterization of Prostate Tumor Polypeptides

This Example describes the isolation of prostate tumor polypeptides from a prostate tumor cDNA library.

A human prostate tumor cDNA expression library was constructed from prostate tumor poly A$^+$RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly A$^+$RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRi/BAXI adaptors (Invitrogen, San Diego, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen) and transformed into ElectroMax *E. coli* DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64 \times 10^7$ independent colonies, with 70% of clones having an insert and the average insert size being 1745 base pairs. The normal pancreas cDNA library contained $3.3 \times 10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood*, 84:189–199, 1994) with some modifications. Specifically, a prostate tumor-specific subtracted cDNA library was generated as follows. Normal pancreas cDNA library (70 μg) was digested with EcoRI, NotI, and SfuI, followed by a filling-in reaction with DNA polymerase Klenow fragment. After phenol-chloroform extraction and ethanol precipitation, the DNA was dissolved in 100 μl of H$_2$O, heat-denatured and mixed with 100 μl (100 μg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 μl) was added and the biotinylation reaction was repeated. After extraction with butanol five times, the DNA was ethanol-precipitated and dissolved in 23 μl H$_2$O to form the driver DNA.

To form the tracer DNA, 10 μg prostate tumor cDNA library was digested with BamHI and XhoI, phenol chloroform extracted and passed through Chroma spin-400 columns (Clontech). Following ethanol precipitation, the tracer DNA was dissolved in 5 μl H$_2$O. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl H$_2$O, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$(Stratagene, La Jolla, Calif. 92037) and transformed into ElectroMax *E. coli* DH10B cells by electroporation to generate a prostate tumor specific subtracted cDNA library (prostate subtraction 1).

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 μg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID NOS: 8–9, 10–11, 12–13, 14–15, 16–17, 18 19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID NOS: 30–40, respectively. Comparison of these sequences with those in the gene bank as described above, revealed no significant homologies to three of the five most abundant DNA species, (J1-17, L1-12 and N1-1 862; SEQ ID NOS: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to *R. norvegicus* mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114.

In a further experiment, four additional clones were identified by subtracting a prostate tumor cDNA library with normal prostate cDNA prepared from a pool of three normal prostate poly A+ RNA (prostate subtraction 2). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H-4781, 1H-4785, 1H-4787, 1H-4796, 1I-4810, 1I-4811, 1J-4876, 1K-4884 and 1K-4896. The 25 determined cDNA sequences for these clones are provided in SEQ ID NOS: 77–92, respectively. Comparison of these sequences with those in the gene bank as described above, revealed no significant homologies to 1G-4741, 1G-4734, 1I-4807, 1J-4876 and 1K-4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1J-4876, 1K-4884 and 1K-4896, provided in SEQ ID NOS: 179–188 and 191–193, respectively, and to the determination of additional partial cDNA sequences for 1I-4810 and 1I-4811, provided in SEQ ID NOS: 189 and 190, respectively.

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1-4278, 1D-4288, 1D-4283, 1D-4304, 1D-4296 and 1D-4280, provided in SEQ ID NOS: 200–206, respectively. cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two novel clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Example 2

Determination of Tissue Specificity of Prostate Tumor Polypeptides

Using gene specific primers, mRNA expression levels for the representative prostate tumor polypeptides F1-16, H1-1, J1-17, L1-12, F1-12 and N1-1862 were examined in a variety of normal and tumor tissues using RT-PCR.

Briefly, total RNA was extracted from a variety of normal and tumor tissues using Trizol reagent as described above. First strand synthesis was carried out using 1–2 µg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 and L1-12 appear to be specifically over-expressed in prostate, with both genes being expressed at high levels in prostate tumor and normal prostate but at low to undetectable levels in all the other tissues examined. N1-1862 was found to be over-expressed in 60% of prostate tumors and detectable in normal colon and kidney. The RT-PCR results thus indicate that F1-16, H1-1, J1-17, N1-1862 and L1-12 are either prostate specific or are expressed at significantly elevated levels in prostate.

Further RT-PCR studies showed that F1-12 is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 is over-expressed in prostate tumors and normal prostate, while being undetectable in other normal tissues tested. J1-17 was detected in two prostate tumors and not in the other tissues tested. N1-1862 was found to be over-expressed in three prostate tumors and to be expressed in normal prostate, colon and kidney, but not in other tissues tested. F1-12 was found to be highly expressed in two prostate tumors and to be undetectable in all other tissues tested.

The micro-array technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 was found to be over-expressed in normal prostate and prostate tumor, with some expression being detected in normal skeletal muscle. Both J1-12 and F1-12 were found to be over-expressed in prostate tumor, with expression being lower or undetectable in all other tissues tested. N1-1862 was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Example 3

Isolation and Characterization of Prostate Tumor Polypeptides by PCR-Based Subtraction A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' $E.$ $coli$ (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79 and P84. The determined cDNA sequences for these clones are provided in SEQ ID NO:41–45, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. An additional clone, referred to as P703, was found to have five splice variants. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCT as described above. Expression was examined in one sample of each tissue type unless otherwise indicated.

P9 was found to be highly expressed in normal prostate and prostate tumor compared to all normal tissues tested except for normal colon which showed comparable expression. P20 was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies using the above methodology resulted in the isolation of twelve additional clones, hereinafter referred to as 10-d8, 10-h10, 11-c8, 7-g6, 8-b5, 8-b6, 8-d4, 8-d9, 8-g3, 8-h11, g-f12 and g-f3. The determined DNA sequences for 10-d8, 10-h10, 11-c8, 8-d4, 8-d9, 8-h11, g-f12 and g-f3 are provided in SEQ ID NO: 207, 208, 209, 216, 217, 220, 221 and 222, respectively. The determined forward and reverse DNA sequences for 7-g6, 8-b5, 8-b6 and 8-g3 are provided in SEQ ID NO: 210 and 211; 212 and 213; 214 and 215; and 218 and 219, respectively. Comparison of these sequences with those in the gene bank revealed no significant homologies to the sequences of 7-g6 and g-f3. The clones 10-d8, 11-c8 and 8-h11 were found to show some homology to previously isolated ESTs, while 10-h10, 8-b5, 8-b6, 8-d4, 8-d9, 8-g3 and g-f12 were found to show some homology to previously identified genes.

Example 4

Synthesis of Polypeptides

Polypeptides may be synthesized on a Perkin Elmer/ Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated DNA molecule comprising a sequence of SEQ ID NO: 107.
2. An isolated DNA molecule comprising a sequence of SEQ ID NO: 109.
3. An isolated DNA molecule comprising a sequence of SEQ ID NO: 110.
4. An isolated DNA molecule comprising a sequence of SEQ ID NO: 111.
5. An isolated DNA molecule consisting of a sequence of SEQ ID NO:171.
6. An isolated DNA molecule consisting of a sequence of SEQ ID NO: 175.
7. An isolated DNA molecule consisting of a sequence of SEQ ID NO: 177.
8. An isolated DNA molecule consisting of a sequence of SEQ ID NO: 223.
9. An isolated DNA molecule consisting of a sequence of SEQ ID NO: 224.
10. An isolated DNA molecule that encodes a polypeptide encoded by a DNA molecule according to any one of claims 1–4 and 5–9.
11. An expression vector comprising the DNA molecule of any one of claims 1–4 and 5–9.
12. A host cell transformed with the expression vector of claim 11.
13. The host cell of claim 12 wherein the host cell is selected from the group consisting of E. coli, yeast and mammalian cell lines.

* * * * *